US007425328B2

(12) United States Patent
Wang

(10) Patent No.: US 7,425,328 B2
(45) Date of Patent: Sep. 16, 2008

(54) TISSUE FACTOR ANTIBODIES AND USES THEREOF

(75) Inventor: Baiyang Wang, Washington Crossing, PA (US)

(73) Assignee: Purdue Pharma L.P., Stamford, CT (US)

( * ) Notice: Subject to any disclaimer, the term of this patent is extended or adjusted under 35 U.S.C. 154(b) by 522 days.

(21) Appl. No.: 10/816,938

(22) Filed: Apr. 5, 2004

(65) Prior Publication Data

US 2004/0229301 A1 Nov. 18, 2004

Related U.S. Application Data

(60) Provisional application No. 60/482,498, filed on Jun. 26, 2003, provisional application No. 60/464,363, filed on Apr. 22, 2003.

(51) Int. Cl.
A61K 39/395 (2006.01)
(52) U.S. Cl. ............. 424/143.1; 424/133.1; 424/141.1; 424/152.1; 424/181.1; 424/183.1; 530/388.1; 530/388.22; 530/391.3; 530/391.7
(58) Field of Classification Search .................. None
See application file for complete search history.

(56) References Cited

U.S. PATENT DOCUMENTS

| 5,110,730 | A | 5/1992 | Edgington et al. |
| 5,223,427 | A | 6/1993 | Edgington et al. |
| 5,437,864 | A | 8/1995 | Edgington et al. |
| 5,506,134 | A | 4/1996 | Soule et al. |
| 5,534,254 | A * | 7/1996 | Huston et al. ............ 424/135.1 |
| 5,622,931 | A | 4/1997 | Edgington et al. |
| 5,877,289 | A | 3/1999 | Thorpe et al. |
| 5,986,065 | A | 11/1999 | Wong et al. |
| 6,001,978 | A | 12/1999 | Edgington et al. |
| 6,004,555 | A | 12/1999 | Thorpe et al. |
| 6,036,955 | A | 3/2000 | Thorpe et al. |
| 6,093,399 | A | 7/2000 | Thorpe et al. |
| 6,262,238 | B1 * | 7/2001 | Steipe et al. ............ 530/387.3 |
| 6,555,319 | B2 | 4/2003 | Wong et al. |
| 6,677,436 | B1 | 1/2004 | Sato et al. |
| 2003/0082636 | A1 | 5/2003 | Wong et al. |
| 2003/0109680 | A1 | 6/2003 | Wong et al. |
| 2003/0119075 | A1 | 6/2003 | Kirchhofer et al. |
| 2003/0124117 | A1 | 7/2003 | Refino et al. |
| 2003/0176664 | A1 | 9/2003 | Jiao et al. |
| 2004/0044187 | A1 | 3/2004 | Sato et al. |

FOREIGN PATENT DOCUMENTS

| JP | 05-244988 | 9/1993 |
| JP | 2001-213804 | 8/2001 |
| WO | WO 94/05328 | 3/1994 |
| WO | WO 96/01653 | 1/1996 |
| WO | WO 97/09063 | 3/1997 |
| WO | WO 98/40408 | 9/1998 |
| WO | WO 01/02439 A1 | 1/2001 |
| WO | WO 01/27079 A2 | 4/2001 |
| WO | WO 01/70984 A2 | 9/2001 |
| WO | WO 03/020111 A2 | 3/2003 |
| WO | WO 03/037911 A2 | 5/2003 |
| WO | WO 03/093422 A2 | 11/2003 |
| WO | WO 03/103711 A1 | 12/2003 |

OTHER PUBLICATIONS

Chen et al., Molecular Medicine., 1995, 1:153-160.*
Vrana et al., Cancer Research, 1996, 56:5063-5070.*
Kageshita et al., Pigment Cell Research, 2001, 14:195-200.*
Presta, LG, Current Pharmaceutical Biotechnology, 2002, 3:237-256.*
Ngo et al., Int. J. cancer, 2007 120:1261-1267.*
Greenberg et al., J. Immunol. 1979, 123:861-869.*
Janeway et al., Immunobiology, third edition, 1997, pp. 3:7-3:11.*
Kipriyanov et al., Molecular Biotechnology, 1999, 12:173-201.*
Caron et al., J Exp Med, 1992, 176:1191-1195.*
Bromberg, M.E., et al., "Tissue factor promotes melanoma metastasis by a pathway indepenent of blood coagulation," *Proc. Natl. Acad. Sci. USA* 92:8205-8209, National Academy of Sciences (1995).
Callander, N.S., et al., "Immunohistochemical Identification of Tissue Factor in Solid Tumors," *Cancer* 70:1194-1201, J.B. Lippincott Company (1992).
Carson, S.D., et al., "An Inhibitory Monoclonal Antibody Against Human Tissue Factor," *Blood* 70:490-493, American Society of Hematology (1987).
Carson, S.D, et al., "Monoclonal Antibodies Against Bovine Tissue Factor, Which Block Interaction With Factor VII$_a$," *Blood* 66:152-156, American Society of Hematology (1985).
Contrino, J., et al., "In situ detection of tissue factor in vascular endothelial cells: Correlation with the malignant phenotype of human breast disease," *Nat. Med.* 2:209-215, Nature Publishing Company (1996).
Drake, T.A., et al., "Selective Cellular Expression of Tissue Factor in Human Tissues," *Am. J. Pathol.* 134:1087-1097, American Association of Pathologists (1989).
Ewan, V., et al., "Production of a Monoclonal Antibody with Anticoagulant Activity for Human Tissue Factor," *Fed. Proc.* 42:521, Federation of American Societies For Experimental Biology (1983).
Ewan, V.A., and Rickles, F.R., "Production of a Monoclonal Antibody with Anticoagulant Activity for Human Tissue Factor," *J. Thromb. Haemost.* 50:406, Blackwell Pub (1983).
Fiore, M.M. et al., "An Unusual Antibody That Blocks Tissue Factor/Factor VIIa Function by Inhibiting Cleavage Only of Macromolecular Substrates," *Blood* 80:3127-3134, American Society of Hematology (1992).

(Continued)

*Primary Examiner*—Michael Szperka
(74) *Attorney, Agent, or Firm*—Sterne, Kessler, Goldstein & Fox P.L.L.C.

(57) ABSTRACT

The present invention provides antibodies capable of binding to human tissue factor, which do not inhibit tissue factor mediated blood coagulation compared to a normal plasma control. Further described are methods of making and methods of using the antibodies of the invention.

43 Claims, 16 Drawing Sheets

OTHER PUBLICATIONS

Hancock, W.W., et al., "Immunohistological Studies with a Monoclonal Antibody to Human Tissue Factor : Normal Distribution and Usefulness as a Marker for Activated Macrophages," *Pathology* 16:479-480, Abstracts of Annual Meeting (1984).

Hu, T., et al., "Procoagulant Activity in Cancer Cells in Dependent on Tissue Factor Expression," *Oncol. Res.* 6:321-327, Elsevier Science (1994).

Hu, Z., and Garen, A., "Targeting tissue factor on tumor vascular endothelial cells and tumor cells for immunotherapy in mouse models of prostatic cancer," *Proc. Natl. Acad. Sci. USA* 98:12180-12185, National Academy of Sciences (2001).

Hu, Z., et al., "Targeting tumor vasculature endothelial cells and tumor cells for immunotherapy of human melanoma in a mouse xenograft model," *Proc. Natl. Acad. Sci. USA* 96:8161-8166, National Academy of Sciences (1999).

Koomagi, R., and Volm, M., "Tissue-factor exprression in human non-small-cell lung carcinoma measured by immunohistochemistry: correlation between tissue factor and angiogenesis," *Int. J. Cancer* 79:19-22, Wiley-Liss (1998).

Morrissey, J.H., et al., "EC11 CD142(tissue factor) Workshop Panel Report," *Leucocyte Typing* 6:742-746, Garland Pub. (1998).

Morrissey, J.H., et al., "Monoclonal antibody analysis of purified and cell-associated tissue factor," *Thromb. Res.* 52:247-261, Pergamon Press (1988).

Ngo, C., et al., "CNTO 89, a Humanized Anti-Tissue Factor Monoclonal Antibody, Inhibits Lung Metastais and Tumor Growth In MDA-MB-231 Breast Cancer Xenograft Models," *Pathophysiol. Haemost. Thromb.* 33, supplement 1:71, Radnor (Sep. 2003).

Nishi, T., et al., "Tissue Factor Expressed in Pituitary Adenoma Cells Contributes to the Development of Vascular Events in Pituitary Adenomas," *Cancer* 86:1354-1361, Wiley (1999).

Rao, L.V., "Characterization of Anti-Tissue Factor Antibody and its Use in Immunoaffinity Purification of Human Tissue Factor," *Thromb. Res.* 51:373-384, Pergamon Press (1988).

Sawada, M., et al., "Expression of tissue factor in non-small-cell lung cancers and its relationship to metastasis," *Br. J. Cancer* 79:472-477, Harcourt Brace and Company Ltd (1999).

Seto, S., et al., "Tissue Factor Expression in Human Colorectal Carcinoma: Correlation with Hepatic Metastasis and Impact on Prognosis," *Cancer* 88:295-301, Wiley (2000).

Shen, B., et al., "Vasculr Endothelial Growth Factor KDR Receptor Signaling Potentiates Tumor Necrosis Factor-induced Tissue Factor Expression in Endothelial Cells," *J. Biol. Chem.* 276:5281-5286, American Society for Biochemistry and Molecular Biology (2001).

Shigemori, C., et al., "Tissue Factor Expression and Metastatic Potential of Colorectal Cancer," *J. Thromb. Haemost.* 80:894-898, Blackwell Pub. (1998).

Tanaka, H., et al., "Purification of Glycosylated Apoprotein of Tissue Factor from Human Brain and Inhibition of its Procoagulant Activity by a Specific Antibody," *Thromb. Res.* 40:745-756, Pergamon Press (1985).

Zacharski, L.R., et al., "Coagulation-Cancer Interaction In Situ in Renal Cell Carcinoma," *Blood* 68:394-399, American Society of Hematology (1986).

Zacharski, L.R., et al., "Occurrence of Fibrin and Tissue Factor Antigen in Human Small Cell Carcinoma of the Lung," *Cancer Res.* 43:3963-3968, American Association for Cancer Research (1983).

Zeldis, S.M., et. al., "Tissue factor (Thromboplastin): Localization to Plasma Membranes by Peroxidase-Conjugated Antibodies," *Science* 175:766-768, American Association for the Advancement of Science (1972).

Patent Abstracts of Japan, English Language Abstract of JP 05-244988 (Document AL1).

Patent Abstracts of Japan, English Language Abstract of JP 2001-213804 (Document AN2).

Abdulkadir, S.A., et. al., "Tissue factor expression and angiogenesis in human prostate carcinoma," *Hum. Pathol.* 31:403-405, W. B. Saunders (2000).

Ahern, S.M., et. al., "Regulation of Human Tissue Factor Expression by mRNA Turnover," *J. Biol. Chem.* 268:2154-2159, The American Society for Biochemistry and Molecular Biology, Inc. (1993).

Akashi, T., et. al., "Tissue factor expression and prognosis in patients with metastatic prostate cancer," *Urology* 62:1078-1082, Elsevier Science (Dec. 2003).

Belting, M., et. al., "Regulation of angiogenesis by tissue factor cytoplasmic domain signaling," *Nature Medicine* 10:502-509, Nature Publishing Group (May 2004).

Cao, Y., "Antiangiogenic cancer therapy," *Semin Cancer Biol.* 14:139-145, Academic Press (Apr. 2004).

Carmeliet, P., and Jain, R.K., "Angiogenesis in cancer and other diseases," *Nature* 407:249-257, Macmillan Magazines Ltd (2000).

Carmeliet, P., and Collen, D., "Molecules in focus: Tissue factor," *Int. J. Biochem. Cell Biol.* 30:661-667, Pergamon Press (1998).

Carmeliet, P., et. al., "Role of tissue factor in embryonic blood vessel development," *Nature* 383:73-75, Nature Publishing Group (1996).

Chiang, H.-S., et. al., "Tissue factor activity of SW-480 human colon adenocarcinoma cells is modulated by thrombin and protein kinase C activation," *Br. J. Cancer* 78:1121-1127, Cancer Research Campaign (1998).

Fleck, R.A., et. al., "Localization of human tissue factor antigen by immunostaining with monospecific, polyclonal anti-human tissue factor antibody," *Thromb Res.* 59:421-437 (1990).

Förster, Y., et. al., "Tissue specific expression and serum levels of human tissue factor in patients with urological cancer," *Cancer Lett.* 193:65-73, Elsevier Science Ireland (Apr. 2003).

Guan, M., et. al., "Quantitative Reverse Transcriptional-PCR Measurement of Tissue Factor mRNA in Glioma," *Mol. Biotechnol.* 20:123-129, Humana Press (Feb. 2002).

Hu, Z., and Garen, A., "Intratumoral injection of adenoviral vectors encoding tumor-targeted immunoconjugates for cancer immunotherapy," *Proc. Natl. Acad. Sci. U.S.A.* 97:9221-9225; National Academy of Sciences (2000).

Huang, X., et. al., "Tumor Infarction in Mice by Antibody-Directed Targeting of Tissue Factor to Tumor Vasculature," *Science* 275:547-550, American Association for the Advancement of Science (1997).

Ishibashi, H., et. al., "Sp1 Decoy Transfected to Carcinoma Cells Suppresses the Expression of Vascular Endothelial Growth Factor, Transforming Growth Factor $\beta_1$, and Tissue Factor and Also Cell Growth and Invasion Activities," *Cancer Res.* 60:6531-6536, American Association for Cancer Research (2000).

Keller, T.; et. al., "Tissue factor is the only activator of coagulation in cultured human lung cancer cells," *Lung Cancer* 31:171-179, Elsevier Scientific Publishers (2001).

Kirschmann, D.A., et. al., "Differentially expressed genes associated with the metastatic phenotype in breast cancer," *Breast Cancer Res. Treat.* 55:127-136, Kluwer Academic Publishers (1999).

Lee, A.Y., "Cancer and thromboembolic disease: pathogenic mechanisms," *Cancer Treat. Rev.* 28:137-140, Elsevier Science Ltd (Jun. 2002).

Lip, G.Y., et. al., "Cancer and the prothrombotic state," *Lancet Oncol.* 3:27-34, Lancet Pub. Group (Jan. 2002).

Lwaleed, B.A., et. al., "The biology and tumour-related properties of monocyte tissue factor," *J. Pathol.* 193:3-12, John Wiley & Sons (2000).

Lykke, J., and Nielson, H.J., "The role of tissue factor in colorectal cancer," *Eur. J. Surg. Oncol.* 29:417-422, Academic Press (Jun. 2003).

Minamiya, Y., et. al., "Expression of tissue factor mRNA and invasion of blood vessels by tumor cells in non-small lung cancer," *Surg. Today* 34:1-5, Springer International (Jan. 2004).

Mueller, B.M., et. al., "Expression of tissue factor by melanoma cells promotes efficient hematogenous metastasis," *Proc. Natl. Acad. Sci. U.S.A.* 89:11832-11836, National Academy of Sciences (1992).

Müller, M., et. al., "Cellular localization of tissue factor in human breast cancer cell lines," *Virchows Arch. B Cell Pathol.* 64:265-269, Springer-Verlag (1993).

Nilsson, F., et. al., "Targeted Delivery of Tissue Factor to the ED-B Domain of Fibronectin, a Marker of Angiogenesis, Mediates the Infarction of Solid Tumors in Mice," *Cancer Res.* 61:711-716, American Association for Cancer Research (2001).

Ohta, S., et. al., "Expression of tissue factor is associated with clinical features and angiogenesis in prostate cancer," *Anticancer Res.* 22:2991-2996, J.G. Delinassios, Anticancer Research (Sep.-Oct. 2002).

Ran, S., et. al., "Infarction of solid Hodgkin's tumors in mice by antibody-directed targeting of tissue factor to tumor vasculature," *Cancer Res.* 58:4646-4653, American Association for Cancer Research (1998).

Ruf, W., "Tissue Factor-Dependent Signaling in Tumor Biology," *Pathophysiol Haemost Thromb.* 33:28-30, Karger (Sep. 2003).

Ruf, W., and Mueller, B.M., "Tissue factor in cancer angiogensis and metastasis," *Curr. Opin. Hematol.* 3:379-384, Rapid Science Publishers (1996).

Semeraro, N., and Colucci, M., "Tissue factor in health and disease," *Thromb. Haemost.* 78:759-764, Schattauer (1997).

Shoji, M., et. al., "Activation of Coagulation and Angiogenesis in Cancer: *Immunohistochemical Localization* in Situ *of Clotting Proteins and Vascular Endothelial Growth Factor in Human Cancer,*" *Am. J. Pathol.* 152:399-411, American Society for Investigative Pathology (1998).

Ueno, T., et. al., "Tissue factor expression in breast cancer tissues: its correlation with prognosis and plasma concentration," *Br. J. Cancer* 83164-170, Cancer Research Campaign (2000).

Volm, M., et. al., "Protein expression profiles of non-small cell lung carcinomas: correlation with histological subtype," *Anticancer Res.* 22:2321-2324, J.G. Delinassios, Anticancer Research (Jul.-Aug. 2002).

Zhang, Y., et. al., "Tissue Factor Controls the Balance of Angiogenic and Antiangiogenic Properties of Tumor Cells in Mice," *J. Clin. Invest.* 94:1320-1327, American Society for Clinical Investigation (1994).

Zucker, S., et. al., "Vascular Endothelial Growth Factor Induces Tissue Factor and Matrix Metalloproteinase Production in Endothelial Cells: Conversion of Prothrombin to Thrombin Results in Progelatinase A Activation and Cell Proliferation," *Int. J. Cancer* 75:780-786, Wiley-Liss, Inc. (1998).

Schwirzke, M., et. al., "New Genes Potentially Involved in Breast Cancer Metastasis," *Anticancer Res.* 19:1801-1814, J.G. Delinassios, Anticancer Research (1999).

International Search Report for International Application No. PCT/US2004/012206, European Patent Office, Netherlands, mailed on Dec. 28, 2004.

The Investigational Drugs database, Drug Report for hATR-5, available online at http://www.iddb3.com/iddb3/iddb3_2/reports.display?id =42643&template=Drugs&i_query_id=3285868, last updated on Mar. 24, 2004, 1 page, Derwent Information Ltd.

The Investigational Drugs database, Drug Report for hOAT, available online at http://www.iddb3.com/iddb3/iddb3_2/reports.display?id=34222&template=Drugs&i_query_id=3285868, last updated on Dec. 23, 2003, accessed on May 4, 2004, 2 pages, Derwent Information Ltd.

The Investigational Drugs database, Drug Report for Sunol-cH36, available online at http://iddb3.com/iddb3/iddb3_2/reports.display?id=34201&template=Drugsi_query_id=3285868, last updated on Dec. 23, 2003, accessed on May 4, 2004, 2 pages, Derwent Information Ltd.

The Investigational Drugs database, Drug Report for anti-tissue factor antibodies (coronary artery disease), available online at http://iddb3.com/iddb3/iddb3_2/reports.display?id=36151&template=Drugs&i_query_id=3285868, last updated on Nov. 6, 2003, accessed on May 4, 2004, 2 pages, Derwent Information Ltd.

The Investigational Drugs database, Drug Report for CNTO-859, available online at http://iddb3.com/iddb3/iddb3_2/reports.display?id=46239&template=Drugs&i_query_id=3285911, last updated on Apr. 22, 2004, accessed on May 4, 2004, 2 pages, Derwent Information Ltd.

* cited by examiner

File: Data.001
Sample ID: CHO
Acquisition Date: 06-May-02

| Marker | % Total | Geo Mean |
|---|---|---|
| All | 100.00 | 5.90 |
| M1 | 92.96 | 5.01 |
| M2 | 6.63 | 56.16 |

File: Data.007
Sample ID: TF34
Acquisition Date: 06-May-02

| Marker | % Total | Geo Mean |
|---|---|---|
| All | 100.00 | 262.38 |
| M1 | 0.42 | 8.16 |
| M2 | 99.44 | 266.56 |

File: Data.004
Sample ID: TF48
Acquisition Date: 06-May-02

| Marker | % Total | Geo Mean |
|---|---|---|
| All | 100.00 | 167.64 |
| M1 | 0.99 | 7.54 |
| M2 | 98.87 | 173.51 |

FIG. 5

```
ATG GAG ACC CCT GCC TGG CCC CGG GTC CCG CGC CCC GAG
 M   E   T   P   A   W   P   R   V   P   R   P   E
ACC GCC GTC GCT CGG ACG CTC CTG CTC GGC TGG GTC TTC
 T   A   V   A   R   T   L   L   L   G   W   V   F
GCC CAG GTG GCC GGC GCT TCA GGC ACT ACA AAT ACT GTG
 A   Q   V   A   G   A   S   G   T   T   N   T   V
GCA GCA TAT AAT TTA ACT TGG AAA TCA ACT AAT TTC AAG
 A   A   Y   N   L   T   W   K   S   T   N   F   K
ACA ATT TTG GAG TGG GAA CCC AAA CCC GTC AAT CAA GTC
 T   I   L   E   W   E   P   K   P   V   N   Q   V
TAC ACT GTT CAA ATA AGC ACT AAG TCA GGA GAT TGG AAA
 Y   T   V   Q   I   S   T   K   S   G   D   W   K
AGC AAA TGC TTT TAC ACA ACA GAC ACA GAG TGT GAC CTC
 S   K   C   F   Y   T   T   D   T   E   C   D   L
ACC GAC GAG ATT GTG AAG GAT GTG AAG CAG ACG TAC TTG
 T   D   E   I   V   K   D   V   K   Q   T   Y   L
GCA CGG GTC TTC TCC TAC CCG GCA GGG AAT GTG GAG AGC
 A   R   V   F   S   Y   P   A   G   N   V   E   S
ACC GGT TCT GCT GGG GAG CCT CTG TAT GAG AAC TCC CCA
 T   G   S   A   G   E   P   L   Y   E   N   S   P
GAG TTC ACA CCT TAC CTG GAG ACA AAC CTC GGA CAG CCA
 E   F   T   P   Y   L   E   T   N   L   G   Q   P
ACA ATT CAG AGT TTT GAA CAG GTG GGA ACA AAA GTG AAT
 T   I   Q   S   F   E   Q   V   G   T   K   V   N
GTG ACC GTA GAA GAT GAA CGG ACT TTA GTC AGA AGG AAC
 V   T   V   E   D   E   R   T   L   V   R   R   N
AAC ACT TTC CTA AGC CTC CGG GAT GTT TTT GGC AAG GAC
 N   T   F   L   S   L   R   D   V   F   G   K   D
TTA ATT TAT ACA CTT TAT TAT TGG AAA TCT TCA AGT TCA
 L   I   Y   T   L   Y   Y   W   K   S   S   S   S
GGA AAG AAA ACA GCC AAA ACA AAC ACT AAT GAG TTT TTG
 G   K   K   T   A   K   T   N   T   N   E   F   L
ATT GAT GTG GAT AAA GGA GAA AAC TAC TGT TTC AGT GTT
 I   D   V   D   K   G   E   N   Y   C   F   S   V
CAA GCA GTG ATT CCC TCC CGA ACA GTT AAC CGG AAG AGT
 Q   A   V   I   P   S   R   T   V   N   R   K   S
ACA GAC AGC CCG GTA GAG TGT ATG GGC CAG GAG AAA GGG
 T   D   S   P   V   E   C   M   G   Q   E   K   G
GAA TTC AGA GAA ATA TTC TAC ATC ATT GGA GCT GTG GTA
 E   F   R   E   I   F   Y   I   I   G   A   V   V
TTT GTG GTC ATC ATC CTT GTC ATC ATC CTG GCT ATA TCT
 F   V   V   I   I   L   V   I   I   L   A   I   S
CTA CAC AAG TGT AGA AAG GCA GGA GTG GGG CAG AGC TGG
 L   H   K   C   R   K   A   G   V   G   Q   S   W
AAG GAG AAC TCC CCA CTG AAT GTT TCA AGA GGA TCC CAC
 K   E   N   S   P   L   N   V   S   R   G   S   H
CAT CAC CAT CAC CAT TAA
 H   H   H   H   H
```

FIG. 6

```
ATG GAG ACC CCT GCC TGG CCC CGG GTC CCG CGC CCC GAG
 M   E   T   P   A   W   P   R   V   P   R   P   E
ACC GCC GTC GCT CGG ACG CTC CTG CTC GGC TGG GTC TTC
 T   A   V   A   R   T   L   L   L   G   W   V   F
GCC CAG GTG GCC GGC GCT TCA GGC ACT ACA AAT ACT GTG
 A   Q   V   A   G   A   S   G   T   T   N   T   V
GCA GCA TAT AAT TTA ACT TGG AAA TCA ACT AAT TTC AAG
 A   A   Y   N   L   T   W   K   S   T   N   F   K
ACA ATT TTG GAG TGG GAA CCC AAA CCC GTC AAT CAA GTC
 T   I   L   E   W   E   P   K   P   V   N   Q   V
TAC ACT GTT CAA ATA AGC ACT AAG TCA GGA GAT TGG AAA
 Y   T   V   Q   I   S   T   K   S   G   D   W   K
AGC AAA TGC TTT TAC ACA ACA GAC ACA GAG TGT GAC CTC
 S   K   C   F   Y   T   T   D   T   E   C   D   L
ACC GAC GAG ATT GTG AAG GAT GTG AAG CAG ACG TAC TTG
 T   D   E   I   V   K   D   V   K   Q   T   Y   L
GCA CGG GTC TTC TCC TAC CCG GCA GGG AAT GTG GAG AGC
 A   R   V   F   S   Y   P   A   G   N   V   E   S
ACC GGT TCT GCT GGG GAG CCT CTG TAT GAG AAC TCC CCA
 T   G   S   A   G   E   P   L   Y   E   N   S   P
GAG TTC ACA CCT TAC CTG GAG ACA AAC CTC GGA CAG CCA
 E   F   T   P   Y   L   E   T   N   L   G   Q   P
ACA ATT CAG AGT TTT GAA CAG GTG GGA ACA AAA GTG AAT
 T   I   Q   S   F   E   Q   V   G   T   K   V   N
GTG ACC GTA GAA GAT GAA CGG ACT TTA GTC AGA AGG AAC
 V   T   V   E   D   E   R   T   L   V   R   R   N
AAC ACT TTC CTA AGC CTC CGG GAT GTT TTT GGC AAG GAC
 N   T   F   L   S   L   R   D   V   F   G   K   D
TTA ATT TAT ACA CTT TAT TAT TGG AAA TCT TCA AGT TCA
 L   I   Y   T   L   Y   Y   W   K   S   S   S   S
GGA AAG AAA ACA GCC AAA ACA AAC ACT AAT GAG TTT TTG
 G   K   K   T   A   K   T   N   T   N   E   F   L
ATT GAT GTG GAT AAA GGA GAA AAC TAC TGT TTC AGT GTT
 I   D   V   D   K   G   E   N   Y   C   F   S   V
CAA GCA GTG ATT CCC TCC CGA ACA GTT AAC CGG AAG AGT
 Q   A   V   I   P   S   R   T   V   N   R   K   S
ACA GAC AGC CCG GTA GAG TGT ATG GGC CAG GAG AAA GGG
 T   D   S   P   V   E   C   M   G   Q   E   K   G
GAA TTC AGA GAA AGA GGA TCC CAC CAT CAC CAT CAC CAT TAA
 E   F   R   E   R   G   S   H   H   H   H   H   H
```

FIG. 7A

CAG GTG CAG CTG AAG CAG TCT GGA GCT GAG CTG ATG AAG
 Q   V   Q   L   K   Q   S   G   A   E   L   M   K
CCT GGG GCC TCA GTG AAG ATA TCC TGC AAG GCT ACT GGC
 P   G   A   S   V   K   I   S   C   K   A   T   G
TAC ACA TTC AGT AGC TAC TGG ATA GAG TGG GTA AAG CAG
 Y   T   F   S   <u>S   Y   W   I   E</u>  W   V   K   Q
AGG CCT GGA CAT GGC CTT GAG TGG ATT GGA GAG ATT TTA
 R   P   G   H   G   L   E   W   I   G   <u>E   I   L
CCT GGA AGT GGT AGT ACT AAC TAC AAT GAG AAG TTC AAG
 P   G   S   G   S   T   N   Y   N   E   K   F   K
GGC AAG GCC ACA TTC ACT GCA GAT ACA TCC TCC AAC ACA
 G</u>  K   A   T   F   T   A   D   T   S   S   N   T
GCC TAC ATG CAA CTC AGC AGC CTG ACA TCT GAG GAC TCT
 A   Y   M   Q   L   S   S   L   T   S   E   D   S
GCC GTC TAT TAC TGT GCA AGA GAG GAT AGG TAC GAC GGT
 A   V   Y   Y   C   A   R   <u>E   D   R   Y   D   G
GAC TAC TGG GGC CAA GGC ACC ACT CTC ACA GTC TCG AG
 D   Y</u>  W   G   Q   G   T   T   L   T   V   S

FIG. 7B

CAG GCT GTT GTG ACT CAG GAA TCT GCA CTC ACC ACA TCA
 Q   A   V   V   T   Q   E   S   A   L   T   T   S
CCT GGT GAA ACA GTC ACA CTC ACT TGT CGC TCA AGT ACT
 P   G   E   T   V   T   L   T   C   <u>R   S   S   T</u>
GGG GCT GTT ACA ACT AGT AAC TAT GCC AAC TGG GTC CAA
 <u>G   A   V   T   T   S   N   Y   A   N</u>  W   V   Q
GAA AAA CCA GAT CAT TTA TTC ACT GGT CTA ATA GGT GGT
 E   K   P   D   H   L   F   T   G   L   I   G   <u>G</u>
ACC AAC AAC CGA GCT CCA GGT GTT CCT GCC AGA TTC TCA
 <u>T   N   N   R   A   P</u>  G   V   P   A   R   F   S
GGC TCC CTG ATT GGA GAC AAG GCT GCC CTC ACC ATC ACA
 G   S   L   I   G   D   K   A   A   L   T   I   T
GGG GCA CAG ACT GAG GAT GAG GCA ATA TAT TTC TGT GCT
 G   A   Q   T   E   D   E   A   I   Y   F   C   <u>A</u>
CTA TGG TAC AGC AAC CAC TGG GTG TTC GGT GGA GGA ACC
 <u>L   W   Y   S   N   H   W   V</u>  F   G   G   G   T
AAA CTG ACT GTC CTA GGT CAG CCC C
 K   L   T   V   L   G   Q   P

FIG. 8A

CAG GTG CAG CTG AAG CAG TCT GGA CCT GAG CTG GAG AAG
  Q   V   Q   L   K   Q   S   G   P   E   L   E   K
CCT GGC GCT TCA GTG AAG ATA TCC TGC AAG GCT TCT GGT
  P   G   A   S   V   K   I   S   C   K   A   S   G
TAC TCA TTC ACT GGC TAC AAC ATG AAC TGG GTG AAG CAG
  Y   S   F   T   <u>G   Y   N   M   N</u>   W   V   K   Q
AGC AAT GGA AAG AGC CTT GAG TGG ATT GGA AAT ATT GAT
  S   N   G   K   S   L   E   W   I   G   <u>N   I   D</u>
CCT TAC TAT GGT GGT ACT AGC TAC AAC CAG AAG TTC AAG
  <u>P   Y   Y   G   G   T   S   Y   N   Q   K   F   K</u>
GGC AAG GCC ACA TTG ACT GTA GAC AAA TCC TCC AAC ACA
  <u>G</u>   K   A   T   L   T   V   D   K   S   S   N   T
GCC TAC ATG CAC CTC AAG AGC CTG ACA TCT GAG GAC TCT
  A   Y   M   H   L   K   S   L   T   S   E   D   S
GCA GTC TAT TAC TGT GCA AGA GAT AGT AGC TCC TGG TTT
  A   V   Y   Y   C   A   R   <u>D   S   S   S   W   F</u>
GCT TAC TGG GGC CAA GGG ACT CTG GTC ACT GTC TCT GCA
  <u>A   Y</u>   W   G   Q   G   T   L   V   T   V   S   A

FIG. 8B

```
GAC ATC CAG CTG ACT CAG TCT CCA GCC TCC CTA TCT GCA
 D   I   Q   L   T   Q   S   P   A   S   L   S   A
TCT GTG GGA GAA ACT GTC ACC ATC ACA TGT CGA GCA AGT
 S   V   G   E   T   V   T   I   T   C   R   A   S
GGG AAT ATT CAC AAT TAT TTA GCA TGG TAT CAG CAG AAA
 G   N   I   H   N   Y   L   A   W   Y   Q   Q   K
CAG GGA AAA TCT CCT CAG CTC CTG GTC TAT AAT GCA AAA
 Q   G   K   S   P   Q   L   L   V   Y   N   A   K
ACC TTA GCA GAT GGT GTG CCA TCA AGG TTC AGT GGC AGT
 T   L   A   D   G   V   P   S   R   F   S   G   S
GGA TCA GGA ACA CAA TAT TCT CTC AAG ATC AAC AGC CTG
 G   S   G   T   Q   Y   S   L   K   I   N   S   L
CAG CCT GAA GAT TTT GGG AGT TAT TAC TGT CAA CAT TTT
 Q   P   E   D   F   G   S   Y   Y   C   Q   H   F
TGG ATT ACT CCG TGG ACG TTC GGT GGA GGC ACC AAG CTG
 W   I   T   P   W   T   F   G   G   G   T   K   L
GAG ATC TAA CGG A
 E   I   K   R
```

FIG. 9A

GAG GTC CAG CTG CAG CAA TCT GGA GCT GAG CTG ATG AAG
 E   V   L   Q   Q   S   G   A   E   L   M   K
CCT GGG GCC TCA GTG AAG ATA TCC TGC AAG GCT ACT GGC
 P   G   A   S   V   K   I   S   C   K   A   T   G
TAC ACA TTC AGT AGC TAC TGG ATA GAG TGG GTA AAG CAG
 Y   T   F   S   <u>S   Y   W   I   E</u>   W   V   K   Q
AGG CCT GGA CAT GGC CTT GAG TGG ATT GGA GAG ATT TTA
 R   P   G   H   G   L   E   W   I   G   <u>E   I   L</u>
CCT GGA AGT GCT AGT ACT AAG TAC AAT GAG AAG TTC AAG
 <u>P   G   S   A   S   T   K   Y   N   E   K   F   K</u>
GGC AAG GCC ACA TTC ACT GCA GAT ACA TCC TCC AAC ACA
 <u>G</u>   K   A   T   F   T   A   D   T   S   S   N   T
GCC TAC ATG CAA CTC AGC AGC CTG ACA TCT GAG GAC TCT
 A   Y   M   Q   L   S   S   L   T   S   E   D   S
GCC GTC TAT TAC TGT GCA AGA GAT TAT TAC TAC GGT AGT
 A   V   Y   Y   C   A   R   <u>D   Y   Y   Y   G   S</u>
AGC TAC GGG TTT GCT TAC TGG GGC CAA GGG ACT CTG GTC
 <u>S   Y   G   F   A   Y</u>   W   G   Q   G   T   L   V
ACT GTC TCG AGT
 T   V   S   S

FIG. 9B

CAG GCT GTT GTG ACT CAG GAA TCT GCA CTC ACC ACA TCA
  Q   A   V   V   T   Q   E   S   A   L   T   T   S

CCT GGT GAA ACA GTC ACA CTC ACT TGT CGC TCA AGT ACT
  P   G   E   T   V   T   L   T   C   <u>R   S   S   T</u>

GGG GCT GTT ACA ACT AGT AAC TAT GCC AAC TGG GTC CAA
  <u>G   A   V   T   T   S   N   Y   A   N</u>   W   V   Q

GAA AAA CCA GAT CAT TTA TTC ACT GGC CTA ATA GGT GGT
  E   K   P   D   H   L   F   T   G   L   I   G   <u>G</u>

ACC AAC AAC CGA GGT CCA GGT GTT CCT GCC AGA TTC TCA
  <u>T   N   N   R   G   P</u>   G   V   P   A   R   F   S

GGC TCC CTG ATT GGA GAC AAG GCT GCC CTC ACC ATC ACA
  G   S   L   I   G   D   K   A   A   L   T   I   T

GGG GCA CAG ACT GAG GAT GAG GCA GTA TAT TTC TGT GCT
  G   A   Q   T   E   D   E   A   V   Y   F   C   <u>A</u>

CTA TGG TAC AGC AAC CAT TGG GTG TTC GGT GGA GGA ACC
  <u>L   W   Y   S   N   H   W   V</u>   F   G   G   T

AAA CTG ACT GTC CTA GGT
  K   L   T   V   L   G

FIG. 10A

CAG GTC CAA CTG CAG CAG CCT GGG GCT GAG CTT GTG AAG
 Q   V   Q   L   Q   Q   P   G   A   E   L   V   K

CCT GGG GCT TCA GTG AAG CTG TCC TGC AAG ACT TCT GGC
 P   G   A   S   V   K   L   S   C   K   T   S   G

TAC ACC TTC ACC AGC TAC TGG ATG CAC TGG GTG AAG CAG
 Y   T   F   T   <u>S   Y   W   M   H</u>   W   V   K   Q

AGG CCT GGA CAA GGC CTT GAG TGG ATC GGA GAG ATT GAT
 R   P   G   Q   G   L   E   W   I   G   <u>E   I   D</u>

CCT TCT GAT AGT TAT ACT AAC TAC AAT CAA AAG TTC AAG
 <u>P   S   D   S   Y   T   N   Y   N   Q   K   F   K</u>

GGC AAG GCC ACA TTG ACT GTA GAC AAA TCC TCC AGC ACA
 <u>G</u>   K   A   T   L   T   V   D   K   S   S   S   T

GCC TAC ATG CAG CTC AGC AGC CTG ACA TCT GAG GAC TCT
 A   Y   M   Q   L   S   S   L   T   S   E   D   S

GCG GTC TAT TAC TGT ACC TAC TAT GTT AAC TAC TAT GCT
 A   V   Y   Y   C   T   Y   <u>Y   V   N   Y   Y   A</u>

ATG GAC TAC TGG GGT CAA GGA ACC TCA GTC ACC GTC TCC
 <u>M   D   Y</u>   W   G   Q   G   T   S   V   T   V   S

TCA
 S

FIG. 10B

```
CAA ATT GTT CTC ACC CAG TCT CCA GCA ATC ATG TCT GCA
 Q   I   V   L   T   Q   S   P   A   I   M   S   A
TCT CTA GGG GAG GAG ATC ACC CTA ACC TGC AGT GCC AGC
 S   L   G   E   E   I   T   L   T   C   S   A   S
TCG AGT GTA AGT TAC ATG CAC TGG TAC CAG CAG AAG TCA
 S   S   V   S   Y   M   H   W   Y   Q   Q   K   S
GGC ACT TCT CCC AAA CTC TTG ATT TAT AGC ACA TCC AAC
 G   T   S   P   K   L   L   I   Y   S   T   S   N
CTG GCT TCT GGA GTC CCT TCT CGC TTC AGT GGC AGT GGG
 L   A   S   G   V   P   S   R   F   S   G   S   G
TCT GGG ACC TTT TAT TCT CTC ACA ATC AGC AGT GTG GAG
 S   G   T   F   Y   S   L   T   I   S   S   V   E
GCT GAA GAT GCT GCC GAT TAT TAC TGC CAT CAG TGG AGT
 A   E   D   A   A   D   Y   Y   C   H   Q   W   S
AGT TAT CCA TAC ACG TTC GGA GGG GGG ACC AAG CTG GAA
 S   Y   P   Y   T   F   G   G   G   T   K   L   E
ATA AAA
 I   K
```

FIG. 11

| | | | | | | | | | | | |
|---|---|---|---|---|---|---|---|---|---|---|---|
| CAG | GTG | CAG | CTG | AAG | GAG | TCT | GGA | GCT | GAG | CTG | ATG | AAG |
| Q | V | Q | L | K | E | S | G | A | E | L | M | K |

| | | | | | | | | | | | |
|---|---|---|---|---|---|---|---|---|---|---|---|
| CCT | GGG | GCC | TCA | GTG | AAG | ATA | TCC | TGC | AAG | GCT | ACT | GGC |
| P | G | A | S | V | K | I | S | C | K | A | T | G |

| | | | | | | | | | | | |
|---|---|---|---|---|---|---|---|---|---|---|---|
| TAC | ACA | TTC | AGT | AGC | TAC | TGG | ATA | GAG | TGG | GTA | AAG | CAG |
| Y | T | F | S | <u>S</u> | <u>Y</u> | <u>W</u> | <u>I</u> | <u>E</u> | W | V | K | Q |

| | | | | | | | | | | | |
|---|---|---|---|---|---|---|---|---|---|---|---|
| AGG | CCT | GGA | CAT | GGC | CTT | GAG | TGG | ATT | GGA | GAG | ATT | TTA |
| R | P | G | H | G | L | E | W | I | G | <u>E</u> | <u>I</u> | <u>L</u> |

| | | | | | | | | | | | |
|---|---|---|---|---|---|---|---|---|---|---|---|
| CCT | GGA | AGT | GGT | AGT | ACT | AAC | TAC | AAT | GAG | AAG | TTC | AAG |
| <u>P</u> | <u>G</u> | <u>S</u> | <u>G</u> | <u>S</u> | <u>T</u> | <u>N</u> | <u>Y</u> | <u>N</u> | <u>E</u> | <u>K</u> | <u>F</u> | <u>K</u> |

| | | | | | | | | | | | |
|---|---|---|---|---|---|---|---|---|---|---|---|
| GGC | AAG | GCC | ACA | TTC | ACT | GCA | GAT | ACA | TCC | TCC | AAC | ACA |
| <u>G</u> | K | A | T | F | T | A | D | T | S | S | N | T |

| | | | | | | | | | | | |
|---|---|---|---|---|---|---|---|---|---|---|---|
| GCC | TAC | ATG | CAA | CTC | AGC | AGC | CTG | ACA | TCT | GAG | GAC | TCT |
| A | Y | M | Q | L | S | S | L | T | S | E | D | S |

| | | | | | | | | | | | |
|---|---|---|---|---|---|---|---|---|---|---|---|
| GCC | GTC | TAT | TAC | TGT | GCA | AGA | GAC | AGG | AAC | GGC | TAC | GTG |
| A | V | Y | Y | C | A | R | <u>D</u> | <u>R</u> | <u>N</u> | <u>G</u> | <u>Y</u> | <u>V</u> |

| | | | | | | | | | | | |
|---|---|---|---|---|---|---|---|---|---|---|---|
| AAC | TAC | TTT | GAC | TCC | TGG | GGC | CAA | GGC | ACC | ACT | CTC | ACA |
| <u>N</u> | <u>Y</u> | <u>F</u> | <u>D</u> | <u>S</u> | W | G | Q | G | T | T | L | T |

| | | |
|---|---|---|
| GTC | TCC | TCA |
| V | S | S |

FIG. 12A

| GAT | GTG | AAG | CTT | CAG | GAG | TCA | GGA | CCT | GAC | CTG | GTG | AAA |
|---|---|---|---|---|---|---|---|---|---|---|---|---|
| D | V | K | L | Q | E | S | G | P | D | L | V | K |

| CCT | TCT | CAG | TCA | CTT | TCA | CTC | ACC | TGC | ACT | GTC | ACT | GGC |
|---|---|---|---|---|---|---|---|---|---|---|---|---|
| P | S | Q | S | L | S | L | T | C | T | V | T | G |

| TAC | TCC | ATC | ACC | AGT | GGT | TAT | AGC | TGG | CAC | TGG | ATC | CGG |
|---|---|---|---|---|---|---|---|---|---|---|---|---|
| Y | S | I | T | <u>S</u> | <u>G</u> | <u>Y</u> | <u>S</u> | <u>W</u> | <u>H</u> | W | I | R |

| CAG | TTT | CCA | GGA | AAC | AAA | CTG | GAA | TGG | ATG | GGC | TAC | ATA |
|---|---|---|---|---|---|---|---|---|---|---|---|---|
| Q | F | P | G | N | K | L | E | W | M | G | <u>Y</u> | <u>I</u> |

| CAC | TAC | AGT | GGT | AGC | ACT | AAG | TAC | AAC | CCA | TCT | CTC | AAA |
|---|---|---|---|---|---|---|---|---|---|---|---|---|
| <u>H</u> | <u>Y</u> | <u>S</u> | <u>G</u> | <u>S</u> | <u>T</u> | <u>K</u> | <u>Y</u> | <u>N</u> | <u>P</u> | <u>S</u> | <u>L</u> | <u>K</u> |

| AGT | CGA | ATC | TCT | ATC | ACT | CGA | GAC | ACA | TCC | AAG | AAC | CAG |
|---|---|---|---|---|---|---|---|---|---|---|---|---|
| <u>S</u> | R | I | S | I | T | R | D | T | S | K | N | Q |

| TTC | TTC | CTG | CAG | TTG | AAT | TCT | GTG | ACT | ACT | GAG | GAC | ACA |
|---|---|---|---|---|---|---|---|---|---|---|---|---|
| F | F | L | Q | L | N | S | V | T | T | E | D | T |

| GCC | ACA | TAT | TAC | TGT | GCA | AGA | CTC | TGG | AGT | TGG | TAC | TTC |
|---|---|---|---|---|---|---|---|---|---|---|---|---|
| A | T | Y | Y | C | A | R | <u>L</u> | <u>W</u> | <u>S</u> | <u>W</u> | <u>Y</u> | <u>F</u> |

| GAT | GTC | TGG | GGC | GCA | GGG | ACC | ACG | GTC | ACC | GTC | TCC | TCA |
|---|---|---|---|---|---|---|---|---|---|---|---|---|
| <u>D</u> | <u>V</u> | W | G | A | G | T | T | V | T | V | S | S |

FIG. 12B

| AAC | ATT | ATG | ATG | ACA | CAG | TCG | CCA | TCA | TCT | CTG | GCT | GTG |
|---|---|---|---|---|---|---|---|---|---|---|---|---|
| N | I | M | M | T | Q | S | P | S | S | L | A | V |

| TCT | GCA | GGA | GAA | AAG | GTC | ACT | ATG | AGC | TGT | AAG | TCC | AGT |
|---|---|---|---|---|---|---|---|---|---|---|---|---|
| S | A | G | E | K | V | T | M | S | C | <u>K</u> | <u>S</u> | <u>S</u> |

| CAA | AGT | GTT | TTA | TAC | AGT | TCA | AAT | CAG | AAG | AAC | TAC | TTG |
|---|---|---|---|---|---|---|---|---|---|---|---|---|
| <u>Q</u> | <u>S</u> | <u>V</u> | <u>L</u> | <u>Y</u> | <u>S</u> | <u>S</u> | <u>N</u> | <u>Q</u> | <u>K</u> | <u>N</u> | <u>Y</u> | <u>L</u> |

| GCC | TGG | TAC | CAG | CAG | AAA | CCA | GGG | CAG | TCT | CCT | AAA | CTG |
|---|---|---|---|---|---|---|---|---|---|---|---|---|
| <u>A</u> | W | Y | Q | Q | K | P | G | Q | S | P | K | L |

| CTG | ATC | TAC | TGG | GCA | TCC | ACT | AGG | GAA | TCT | GGT | GTC | CCT |
|---|---|---|---|---|---|---|---|---|---|---|---|---|
| L | I | Y | <u>W</u> | <u>A</u> | <u>S</u> | <u>T</u> | <u>R</u> | <u>E</u> | <u>S</u> | G | V | P |

| GAT | CGC | TTC | ACA | GGC | AGT | GGA | TCT | GGG | ACA | GAT | TTT | ACT |
|---|---|---|---|---|---|---|---|---|---|---|---|---|
| D | R | F | T | G | S | G | S | G | T | D | F | T |

| CTT | ACC | ATC | AGC | AGT | GTA | CAA | GCT | GAA | GAC | CTG | GCA | GTT |
|---|---|---|---|---|---|---|---|---|---|---|---|---|
| L | T | I | S | S | V | Q | A | E | D | L | A | V |

| TAT | TAC | TGT | CAT | CAA | TAC | CTC | TCC | TCG | TAC | ACG | TTC | GGA |
|---|---|---|---|---|---|---|---|---|---|---|---|---|
| Y | Y | C | <u>H</u> | <u>Q</u> | <u>Y</u> | <u>L</u> | <u>S</u> | <u>S</u> | <u>Y</u> | <u>T</u> | F | G |

| GGG | GGG | ACC | AAG | CTG | GAA | ATA | AAA |
|---|---|---|---|---|---|---|---|
| G | G | T | K | L | E | I | K | ic region. The extracellular region of TF has two fibronectin
TISSUE FACTOR ANTIBODIES AND USES THEREOF

BACKGROUND OF THE INVENTION

1. Field of the Invention

The invention relates to antibodies capable of binding to tissue factor, without inhibiting normal tissue factor mediated blood coagulation, and methods of making and methods of use thereof, including in the treatment of cancer.

2. Related Art

Tissue factor (TF) is a cell-anchored component that, together with factor VIIa, initiates blood coagulation in vivo. TF is a transmembrane glycoprotein with a 219 amino acid residue extracellular region, a 23 amino acid residue transmembrane region and a 21 amino acid residue cytoplasmic region. The extracellular region of TF has two fibronectin III-like domains and a distribution of disulfide bridges characteristic of class-II cytokine and interferon receptors. The cytoplasmic region of TF is short but contains at least one serine residue that can be phosphorylated.

Tissue factor forms a tight complex ($K_d$~pmol) with its native ligand—factor VIIa. In the complex, VIIa wraps around tissue factor (Banner, D. W., et al., *Nature* 380:41-46 (1996)) and forms an extensive region of contact with the tissue factor surface.

Patients with cancer exhibit a much higher than expected incidence of thromboembolic disorders, commonly referred to as Trousseau syndrome. Many tumor types commonly associated with Trousseau syndrome, such as lung, pancreatic, breast, colon, and gastric carcinomas, stain positively for TF (Hu, T., et al., *Oncol. Res.* 6:321-327 (1994); Callander, N. S., et al., *Cancer* 70:1194-201 (1992)). Abnormally high expression of TF has been shown clinically to be associated with poor differentiation of many tumors, including colorectal carcinoma (Shigemori, C., et al., *Thromb. Haemost.* 80:894-898 (1998); Seto, S., et al., *Cancer* 88:295-301 (2000)); and non-small cell lung cancer (Sawada, M., et al., *Br. J. Cancer* 79:472-477 (1999)). Molecular analysis of gene expression shows that TF is differentially expressed in breast cancer cells (Kirschmann, D. A., et al., *Breast Cancer Res. Treat.* 55:127-136 (1999); Schwirzke, M., et al., *Anticancer Res.* 19:1801-1814 (1999)).

In tumor tissues, TF is not only expressed on the surface of tumor cells but also on tumor associated vascular endothelial cells. TF has been shown to play an essential role in embryonic blood vessel development (Carmeliet, P., et al., *Nature* 383:73-75 (1996)). TF normally is not expressed in the endothelium. However, tumor associated vascular endothelial cells in breast cancer (Contrino, J., et al., *Nat. Med.* 2:209-215 (1996); Shoji, M., et al., *Am. J. Pathol.* 152:399-411 (1998)), pituitary adenoma (Nishi, T., et al., *Cancer* 86:1354-1361 (1999)) and lung cancer (Shoji, M., et al., *Am. J. Pathol.* 152:399-411 (1998); Koomagi, R. and Vohm, M., *Int. J. Cancer* 79:19-22 (1998)) have been shown to express TF. The expression of TF by tumor cells and tumor associated vascular endothelial cells was shown to be induced by tumor secreted VEGF and TNF (Bierhaus, A., et al., *J. Biol. Chem.* 270:26419-26432 (1995); Zucker, S., et al., *Int. J. Cancer* 75:780-786 (1998); Shen, B. Q., et al., *J. Biol. Chem.* 276: 5281-5286 (2001)).

In normal tissue, TF is only expressed in cells separated from blood proteins by tight endothelium and tissue barriers such as skin, and TF is normally not readily accessible to blood proteins and antibodies. However, in tumor tissues, TF of tumor associated vascular endothelial cells is exposed to blood proteins. At the same time, tumor TF is also accessible because of the leaky tumor vasculature. Tumor cells secrete matrix metalloproteases that most likely play a role in the invasion process, and may be a cause of the leakiness.

Antibodies that bind to the TF-VIIa interaction site can inhibit TF-VIIa interaction, thus inhibiting or blocking blood coagulation. However, when large quantities of those antibodies are used for tumor therapy, effective bleeding control in patients may be compromised.

SUMMARY OF THE INVENTION

The present invention is directed to an isolated antibody capable of binding to human tissue factor (hTF), wherein the antibody does not inhibit tissue factor (TF) mediated blood coagulation when compared to a normal plasma control. The present invention is also directed to an isolated antibody capable of binding to hTF, wherein the antibody does not inhibit TF mediated blood coagulation when compared to a normal plasma control, and wherein the antibody can initiate an Fc-mediated mechanism. The antibody can be a monoclonal antibody, a chimeric antibody, a single chain antibody, a humanized antibody, a modified antibody, a heavy or light chain variable region thereof, or an antibody product of a Fab expression library. The present invention is further directed to hybridomas producing such an antibody, as well as nucleic acid molecules encoding such an antibody.

The present invention is further directed to an immunoglobulin molecule comprising the heavy or light chain variable region of the antibody.

The present invention is further directed to an anti-antibody capable of interfering with the binding of the antibody to hTF.

The present invention is further directed to a method of producing a monoclonal antibody of the invention, the method comprising: (a) immunizing a mammal with a polypeptide comprising a purified extracellular domain of hTF; (b) preparing a cell suspension from lymph nodes of the immunized mammal; (c) fusing cells from the cell suspension of step (b) with myeloma cells; and (d) identifying a clone from a hybridoma generated from the fusion in (c), wherein the clone produces an antibody capable of binding to hTF but does not inhibit TF mediated blood coagulation compared to a normal plasma control, and optionally wherein the antibody can initiate an Fc-mediated mechanism.

The invention is further directed to a pharmaceutical composition comprising a therapeutically effective amount of the antibody of the invention and a pharmaceutically acceptable carrier.

The present invention is also directed to a method of treating cancer in a patient, the method comprising administering to the patient a therapeutically effective amount of the antibody of the invention. The antibody can be conjugated to a cytotoxic agent or a radionuclide.

The invention is further directed to an isolated polynucleotide having a nucleotide sequence encoding an antibody of the invention. The invention is further directed to an isolated polynucleotide having a nucleotide sequence encoding a polypeptide that is at least 70%, at least 80%, at least 85%, at least 90%, at least 95%, at least 96%, at least 97%, at least 98%, or at least 99% identical in amino acid sequence to an antibody, or antibody fragment thereof, of the invention. In some embodiments, such a polypeptide has the immunospecificity of an antibody of the present invention. The invention is also directed to a vector comprising the isolated polynucleotide, and a host cell comprising the vector.

The invention is further directed to a kit comprising a pharmaceutical composition comprising a therapeutically effective amount of the antibody of the invention. In some embodiments, the kit further comprises printed matter which provides information on the use of the pharmaceutical composition to treat cancer or a pre-recorded media device which provides information on the use of the pharmaceutical composition to treat cancer or a planner.

The present invention is also directed to a method of delivering a pharmaceutical composition comprising a therapeutically effective amount of the antibody of the present invention to a patient in need thereof, the method comprising (a) registering in a computer readable medium the identity of a physician permitted to prescribe the pharmaceutical composition; (b) providing the patient with counseling information concerning the risks attendant to the pharmaceutical composition; (c) obtaining informed consent from the patient to receive the pharmaceutical composition despite the attendant risks; (d) registering the patient in a computer readable medium after obtaining their informed consent; and (e) permitting the patient access to the pharmaceutical composition.

The present invention is also directed to a method of educating consumers about the use of a pharmaceutical composition, the method comprising distributing the pharmaceutical composition with consumer information at a point of sale.

The present invention is also directed to a method of detecting cancer, the method comprising providing the antibody of the invention, conjugated to a detectable agent, to a sample or subject and detecting the detectable agent bound to cancer cells.

The present invention is further directed to a method of identifying a pharmaceutical composition comprising a therapeutically effective amount of the antibody of the invention, and commercializing the same as a drug, the method comprising (a) isolating an antibody capable of binding to human tissue factor, wherein the antibody does not inhibit tissue factor mediated blood coagulation compared to normal plasma controls and can initiate an Fc-mediated mechanism; (b) repeating (a) to obtain a plurality of candidate antibodies that may prove therapeutically effective; (c) demonstrating that one such candidate antibody is non-toxic when administered to a non-human animal; (d) conducting a supervised clinical trial to demonstrate the non-toxic and effective character of one such candidate antibody; (e) securing approval of a regulatory agency to distribute one such candidate antibody to treat cancer; and (f) making a pharmaceutical composition comprising the candidate antibody as the active agent.

BRIEF DESCRIPTION OF THE FIGURES

FIG. 3A. Untransfected CHO cells. FIG. 3B. Representative stable clone #TF34. FIG. 3C. Representative stable clone #TF48.

FIG. 5. Nucleotide (SEQ ID NO:1) and amino acid (SEQ ID NO:2) sequences of full length human tissue factor with a 32 amino acid N-terminal leader sequence and a 9 amino acid C-terminal RGS-His$_6$ tag sequence.

FIG. 6. Nucleotide (SEQ ID NO:3) and amino acid (SEQ ID NO:4) sequences of the extracellular domain of human tissue factor with a 32 amino acid N-terminal leader sequence and a 9 amino acid C-terminal RGS-His$_6$ tag sequence.

FIGS. 7A-7B. Antibody TF260. FIG. 7A. Nucleotide (SEQ ID NO:5) and amino acid (SEQ ID NO:6) sequences of TF260 VH (TF260VH/PUC18). FIG. 7B. Nucleotide (SEQ ID NO:7) and amino acid (SEQ ID NO:8) sequences of TF260 VL (TF260VL/PUC18).

FIGS. 8A-8B. Antibody TF196. FIG. 8A. Nucleotide (SEQ ID NO:9) and amino acid (SEQ ID NO:10) sequences of TF196 VH (TF196VH/PUC18). FIG. 8B. Nucleotide (SEQ ID NO:11) and amino acid (SEQ ID NO:12) sequences of TF196 VL (TF196VH/PUC18).

FIGS. 9A-9B. Antibody TF278. FIG. 9A. Nucleotide (SEQ ID NO:18) and amino acid (SEQ ID NO:19) sequences of TF278 VH (TF278VHs-PUC18). FIG. 9B. Nucleotide (SEQ ID NO:20) and amino acid (SEQ ID NO:21) sequences of TF278 VL (TF278VLs-PUC18).

FIGS. 10A-10B. Antibody TF277. FIG. 10A. Nucleotide (SEQ ID NO:22) and amino acid (SEQ ID NO:23) sequences of TF277 VH. FIG. 10B. Nucleotide (SEQ ID NO:24) and amino acid (SEQ ID NO:25) sequences of TF277 VL.

FIG. 11. Antibody TF392. Nucleotide (SEQ ID NO:26) and amino acid (SEQ ID NO:27) sequences of TF392 VH (TF392VHs-PUC18). The nucleotide and amino acid sequences of TF392 VL are the same as the nucleotide (SEQ ID NO:7) and amino acid (SEQ ID NO:8) sequences of TF260 VL.

FIGS. 12A-12B. Antibody TF9. FIG. 12A. Nucleotide (SEQ ID NO:28) and amino acid (SEQ ID NO:29) sequences of TF9VH (TF9VHs-PUC18). FIG. 12B. Nucleotide (SEQ ID NO:30) and amino acid (SEQ ID NO:31) sequences of TF9 VL (TF9VL-PUC18).

Note: In FIGS. 7A-12B, the underlined amino acid residues specify the CDR regions of the VH or VL region of antibodies TF260, TF196, TF278, TF277, TF392 and TF9, respectively.

Figure 1:
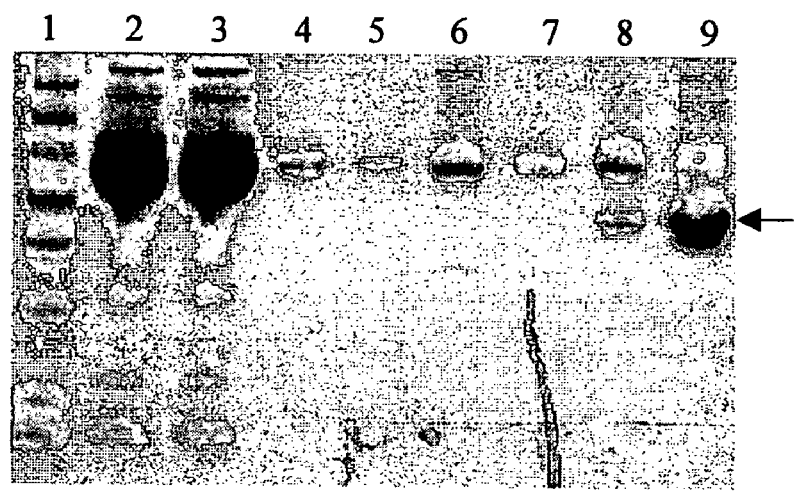
FIG. 1. Purification of soluble human tissue factor (hTF) using Ni-agarose column. Lane 1 contains molecular weight markers. Lane 2 is pre-purification and lanes 3-4 are flow-through and wash samples. Lanes 5-9 are fractions eluted with an imidazole gradient. The arrow indicates soluble hTF. Fractions 11-14 that contained protein bands as in lane 8 were pooled and further purified using gel-filtration chromatography. Fractions 15-26 that contained protein bands as in lane 9 were pooled and used for immunization.

Note: A 57 nucleotide (a 19 amino acid) sequence signal peptide:

ATG GCT TGG GTG TGG ACC TTG CTA TTC CTG ATG GCA GCT GCC CAA AGT GCC CAA GCA (SEQ ID NO:32)

M   A   W   V   W   T   L   L   F   L   M   A   A   A   Q   S   A   Q   A (SEQ ID NO:33)

was used in constructing a vector containing VH and VL of TF260, TF196, TF278, TF277, TF392, or VH of TF9. A 60 nucleotide (a 20 amino acid) sequence signal peptide:

ATG GAA TCA CAG ACT CAG GTC TTC CTC TCC CTG CTG CTC TGG ATA TCT GGT ACC TGT GGG (SEQ ID NO:34)

M   E   S   Q   T   Q   V   F   L   S   L   L   L   W   I   S   G   T   C   G (SEQ ID NO:35)

was used in constructing a vector containing VL of TF 9.

DETAILED DESCRIPTION OF THE PREFERRED EMBODIMENTS

In normal tissue, TF is only expressed in cells separated from blood proteins by tight endothelium and tissue barriers such as skin. TF is normally not accessible to blood proteins including antibodies, since TF is not usually expressed on the surface of cells that are in direct contact with blood such as the endothelium lining vessels. However, TF is expressed by many types of tumor cells including tumor associated vascular endothelial cells, where TF is exposed to blood proteins. TF is involved in embryonic blood vessel development and has been associated with tumor metastasis. Thus, TF is considered to be a potential tumor therapeutic target.

Antibodies

The invention is directed to an isolated antibody capable of binding to human TF (hTF), wherein the antibody does not inhibit TF mediated blood coagulation compared to a normal plasma control. The invention is also directed to an isolated antibody capable of binding to hTF, wherein the antibody does not inhibit TF mediated blood coagulation compared to a normal plasma control and wherein the antibody can initiate one or more Fc-mediated mechanisms. Because the antibodies of the invention do not inhibit normal TF mediated blood coagulation, normal plasma clotting is not affected in patients treated with antibodies of the invention.

As used herein, "isolated" refers to material removed from its original environment (e.g., the natural environment if it is naturally occurring), and thus is altered "by the hand of man" from its natural state.

The basic antibody structural unit is known to comprise a tetramer composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxyl-terminal portion of each chain defines a constant region primarily responsible for Fc-mediated mechanisms. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, *Fundamental Immunology*, Ch. 7 (Paul, W., ed., 2nd ed. Raven Press, N.Y. (1989)). The variable regions of each light/heavy chain pair form the antigen binding site.

Thus, an intact IgG antibody has two binding sites. Except in bifunctional or bispecific antibodies, the two binding sites are the same.

The variable regions all exhibit the same general structure of relatively conserved framework regions (FR) joined together by three hypervariable regions, also called complementarity determining regions or CDRs. The CDRs from the heavy and the light chains of each pair are aligned by the framework regions, enabling binding to a specific epitope. From N-terminal to C-terminal, both variable region light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. (1987 and 1991)); Chothia & Lesk, *J. Mol. Biol.* 196:901-917 (1987); or Chothia et al., *Nature* 342:878-883 (1989).

As used herein, the term "antibody" is intended to refer to intact immunoglobulin molecules and immunologically active portions or fragments of immunoglobulin molecules, i.e., molecules that contain an antigen binding site that immunospecifically binds an antigen. The antibody of the invention is capable of specifically binding to hTF, without inhibiting TF mediated blood coagulation compared to a normal plasma control. In certain embodiments, the antibody of the invention is capable of specifically binding to hTF, without inhibiting TF mediated blood coagulation compared to a normal plasma control, and wherein the antibody can initiate one or more Fc-mediated mechanisms Antibodies of the invention include, but are not limited to, intact monoclonal, multispecific, human, humanized and chimeric antibodies, modified antibodies, single chain antibodies, single-chain Fvs (scFv), disulfide-linked Fvs (sdFv), Fab fragments, F(ab') fragments, F(ab')$_2$ fragments, Fv fragments, fragments produced by a Fab expression library, fragments comprising either a VL or VH domain, anti-idiotypic (anti-Id) antibodies (including, e.g., anti-Id antibodies to antibodies of the invention), intracellularly-made antibodies (i.e., intrabodies), and antigen-binding antibody fragments. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In some embodiments, the immunoglobulin is an IgG1 isotype. In other embodiments, the immunoglobulin is an IgG2 isotype. In yet other embodiments, the immunoglobulin is an IgG4 isotype. Immunoglobulins can have both heavy and light chains. An array of IgG, IgE, IgM, IgD, IgA, and IgY heavy chains can be paired with a light chain of the kappa or lambda form.

Antibodies of the invention can also comprise the variable region(s) alone or in combination with the entirety or a portion of the following: hinge region, CH1, CH2, CH3 and/or Fc domain(s). The antibodies of the invention can be from any animal origin, including birds and mammals. In some embodiments, the antibodies are human, murine, rat, donkey, sheep, rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins. Thus, it should be understood that antibodies of the invention from an animal are capable of binding to human tissue factor and do not inhibit TF mediated blood coagulation when compared to a normal plasma control. Such antibodies can initiate one or more Fc-mediated mechanisms.

The term "monoclonal antibody" as used herein refers to an antibody obtained from a population of substantially homogeneous antibodies, i.e., the individual antibodies comprising the population are identical except for possible naturally occurring mutations that can be present in minor amounts. In contrast to conventional (polyclonal) antibody preparations that typically include different antibodies directed against different determinants (epitopes), each monoclonal antibody is directed against a single determinant on the antigen and is therefore highly specific. In addition to their specificity, monoclonal antibodies are advantageous since they are synthesized by hybridoma cultures, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler & Milstein, Nature 256:495 (1975), or alternatively can be made by recombinant DNA methods (see e.g., U.S. Pat. No. 4,816,567 (Cabilly et al.)).

"Chimeric" antibodies (immunoglobulins) refer to those antibodies having a portion of the heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567 (Cabilly et al.); Morrison et al., Proc. Nat. Acad. Sci. USA 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding sub-sequences of antibodies) which contain minimal sequence derived from a non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity and affinity. In some instances, Fv framework residues of the human immunoglobulin are replaced by corresponding non-human residues. Furthermore, a humanized antibody can comprise residues that are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin sequence. The humanized antibody optionally will also comprise at least a portion of an immunoglobulin constant region (Fc), typically that of a human immunoglobulin. For further details, see, Jones et al., Nature 321:522-525 (1986); Reichmann et al., Nature 332:323-329 (1988); and Presta, Curr. Op. Struct. Biol. 2:593-596 (1992).

The term "modified antibody" refers to an antibody that has been modified with respect to effector function, so as to enhance the effectiveness of the antibody at mediating antibody-dependent cellular cytotoxicity (ADCC) and/or complement-dependent cytotoxicity (CDC) (also known as complement-mediated cell killing). For example, cysteine residue(s) can be introduced in the Fc region, thereby allowing interchain disulfide bond formation in this region. The homodimeric antibody thus generated can have improved internalization capability and/or increased ADCC and CDC. See Caron et al., J. Exp. Med. 176:1191-1195 (1992) and Shopes, B., J. Immunol. 148: 2918-2922 (1992). Homodimeric antibodies with enhanced anti-tumor activity can also be prepared using heterobifunctional cross-linkers as described in Wolff et al., Cancer Research 53: 2560-2565 (1993). Alternatively, an antibody can be modified such that it has dual Fc regions and can thereby have enhanced complement-mediated lysis and ADCC capabilities. See Stevenson et al., Anti-Cancer Drug Design 3:219-230 (1989). Additionally, an antibody can be engineered to produce glycoforms which have altered glycosylation patterns that result in enhanced ADCC activity. See U.S. Pat. No. 6,602,684.

A bispecific or bifunctional antibody is an artificial hybrid antibody having two different heavy/light chain pairs and two different binding sites. Bispecific antibodies can be produced by a variety of methods including fusion of hybridomas or linking of F(ab') fragments. See, e.g., Songsivilai & Lachmann, Clin. Exp. Immunol. 79:315-321 (1990), Kostelny et al., J. Immunol. 148:1547 1553 (1992). In addition, bispecific antibodies can be formed as "diabodies" (Holliger et al., PNAS USA 90:6444-6448 (1993)) or "Janusins" (Traunecker et al., EMBO J. 10:3655-3659 (1991) and Traunecker et al., Int. J. Cancer Suppl. 7:51-52 (1992)).

The invention is also directed to an immunoglobulin molecule comprising the heavy or light chain variable region of the antibody of the invention. The invention is further directed to an isolated anti-antibody capable of interfering with the binding of the antibody of the invention to hTF, wherein said anti-antibody does not inhibit TF mediated blood coagulation compared to a normal plasma control.

Antibodies of the present invention can also be described or specified in terms of their cross-reactivity. In some embodiments, antibodies of the invention bind polypeptides having at least about 95%, at least about 90%, at least about 85%, at least about 80%, at least about 75%, at least about 70%, at least about 65%, at least about 60%, at least about 55%, at least about 50%, at least about 45%, or at least about 40% amino acid sequence identity to a TF polypeptide (e.g., human TF (SEQ ID NO:2)), or a fragment of the TF polypeptide. In some embodiments, antibodies of the present invention cross-react with murine, monkey, rat and/or rabbit homologs of hTF and the corresponding epitopes thereof. In other embodiments, the above-described cross-reactivity is with respect to any single specific antigenic or immunogenic polypeptide, or combination(s) of 2, 3, 4, 5, or more of specific antigenic and/or immunogenic polypeptides.

As known in the art, "sequence identity" between two polypeptides is determined by comparing the amino acid sequence of one polypeptide to the sequence of a second polypeptide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, *Advances in Applied Mathematics* 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

The antibodies of the invention can bind immunospecifically to a hTF polypeptide or a polypeptide fragment of hTF. In some embodiments, the antibodies of the invention bind immunospecifically to hTF. In other embodiments, the antibodies of the invention bind immunospecifically to the extracellular domain of hTF. As used herein, "extracellular domain of hTF" is intended to refer to the 219 amino acid residue portion of hTF that is localized on the outside surface of the cell (see e.g., FIG. 6, providing the nucleotide (SEQ ID NO:3) and amino acid (SEQ ID NO:4) sequences of the extracellular domain of human tissue factor with a 32 amino acid N-terminal leader sequence and a 9 amino acid C-terminus RGS-His$_6$ tag sequence).

In some embodiments, the antibodies of the present invention preferentially bind to hTF. In other embodiments, the antibodies of the present invention immunospecifically bind to hTF and do not cross-react with any other antigens. The antibodies of the present invention do not inhibit TF mediated blood coagulation compared to a normal plasma control. In other embodiments, the antibodies of the invention initiate one or more Fc-mediated mechanisms.

The term "antigen-binding antibody fragment" is intended to refer to a molecule (e.g., a polypeptide) which is a portion or part of a polypeptide sequence as compared to a corresponding full length or native polypeptide sequence of an antibody of the invention. The portion or part of a polypeptide sequence can be at least about 10%, at least about 20%, at least about 30%, at least about 40%, at least about 50%, at least about 60%, at least about 70%, at least about 80%, at least about 90%, at least about 95%, or at least about 99% of the full length or native polypeptide sequence of a full size antibody of the invention, but which retains at least some degree of binding specificity of the full length antibody, and does not inhibit TF mediated blood coagulation compared to a normal plasma control, and optionally, initiate an Fc-mediated mechanism.

Antigen-binding antibody fragments (including derivatives) of the antibody molecules (e.g., the VH domains and/or VL domains) described herein include, but are not limited to, fragments (including derivatives) of at least 20, at least 40, at least 60, at least 80, at least 100, at least 120, at least 140, at least 160, or more than 160 amino acids of the full length antibody, including the VH domain, VHCDR1, VHCDR2, VHCDR3, VL domain, VLCDR1, VLCDR2, or VLCDR3.

The resultant antibody or antigen-binding antibody fragments can be screened for biological activity to identify fragments that retain the desired activity (e.g., the ability to bind hTF).

By way of a non-limiting example, an antibody can be considered to bind hTF preferentially if it binds the protein with a dissociation constant ($K_D$) or an off rate ($K_{off}$), that is less than the antibody's $K_D$ or $K_{off}$ for a second antigen. In other non-limiting embodiments, an antibody can be considered to bind hTF preferentially if it binds the protein with a $K_D$ or $K_{off}$ that is at least one order of magnitude less than the antibody's $K_D$ or $K_{off}$ for the second antigen. In other non-limiting embodiments, an antibody can be considered to bind hTF preferentially if it binds hTF with a $K_D$ or $K_{off}$ that is at least two orders of magnitude less than the antibody's $K_D$ or $K_{off}$ for the second antigen.

Antibodies of the present invention can also be described or specified in terms of their binding affinity to hTF. In some embodiments, binding affinities include those with a dissociation constant or $K_D$ less than or equal to $5 \times 10^{-2}$ M, $10^{-2}$ M, $5 \times 10^{-3}$ M, $10^{-3}$ M, $5 \times 10^{-4}$ M, or $10^{-4}$ M. In other embodiments, affinities include those with a dissociation constant or $K_D$ less than or equal to $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M or $10^{-8}$ M. In yet other embodiments, binding affinities include those with a dissociation constant or $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In some embodiments, antibodies of the invention can bind hTF polypeptides with an off rate ($K_{off}$) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. In other embodiments, antibodies of the invention can bind hTF polypeptides or fragments thereof with an off rate ($K_{off}$) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

In some embodiments of the present invention, antibodies that immunospecifically bind to hTF can comprise a polypeptide having the amino acid sequence of any one of the heavy chains expressed by an anti-TF antibody expressing cell line of the invention and/or any one of the light chains expressed by an anti-TF antibody expressing cell line of the invention. In other embodiments of the present invention, antibodies that immunospecifically bind to hTF can comprise a polypeptide having the amino acid sequence of any one of the VH domains of a heavy chain expressed by an anti-TF antibody expressing cell line of the invention and/or any one of the VL domains of a light chain expressed by an anti-TF antibody expressing cell line of the invention. In yet other embodiments, antibodies of the present invention can comprise the amino acid sequence of a VH domain and VL domain expressed by a single anti-TF antibody expressing cell line of the invention. In other embodiments, antibodies of the present invention can comprise the amino acid sequence of a VH domain and a VL domain expressed by two different anti-TF antibody expressing cell lines of the invention. Molecules comprising, or alternatively consisting of, antigen-binding antibody fragments of the VH and/or VL domains expressed by an anti-TF antibody expressing cell line of the invention that immunospecifically bind to hTF are also encompassed by the invention, as are nucleic acid molecules encoding these VH and VL domains, molecules, and/or fragments.

The present invention also provides polypeptides that comprise, or alternatively consist of, variants (including derivatives) of the antibody molecules (e.g., the VH domains and/or VL domains) described herein, which polypeptides immunospecifically bind to hTF or a fragment or variant thereof. The term "variant" refers to a molecule (e.g., a polypeptide or polynucleotide sequence) with at least one or more differences in its amino acid or nucleotide sequence as compared to a corresponding native polypeptide or DNA sequence. Amino acid sequence variants of the invention will possess at least about 70%, at least about 75%, at least about 85%, at least about 95%, or at least about 99% sequence identity with the amino acid sequence of an anti-TF antibody of the invention. Substitutional variants are those that have at least one amino acid residue in a native sequence removed and a different amino acid inserted in its place at the same position. The substitutions can be single, where only one amino acid in the molecule has been substituted, or they can be multiple, where two or more amino acids have been substituted in the same molecule. Insertional variants are those with one or more amino acids inserted immediately adjacent to an amino acid at a particular position in a native amino acid sequence connected to either the α-carboxyl or α-amino functional group of the amino acid. Deletional variants are those with one or more amino acids removed from the native amino acid sequence. Ordinarily, deletional variants will have one or two amino acids deleted in a particular region of the molecule. Standard techniques known to those of skill in the art can be used to introduce mutations into an antibody of the invention, including, for example, by site-directed mutagenesis or PCR-mediated mutagenesis of the encoding nucleic acid molecule which results in amino acid substitutions. In some embodiments, the variant (including derivatives) has less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference polypeptide. In some embodiments, the variant polypeptide has the same immunospecificity, or binds the same epitope, as a polypeptide of the present invention.

It is well known in the art that polypeptides, or fragments or variants thereof, with similar amino acid sequences can have similar structure and many of the same biological activities. Thus, the invention is further directed to an isolated first antibody, or antigen-binding fragment thereof, having an amino acid sequence at least 70%, at least 80%, at least 85%, at least 90%, at least 95%, at least 96%, at least 97%, at least 98%, or at least 99% identical to a second antibody comprising an amino acid sequence selected from the group consisting of: (a) at least one CDR region of a VH domain of the antibody expressed by hybridoma cell line TF196 (deposited May 15, 2003, ATCC Deposit No. PTA-5196); (b) at least one CDR region of a VH domain of the antibody expressed by hybridoma cell line TF260 (deposited May 15, 2003, ATCC Deposit No. PTA-5197); (c) at least one CDR region of a VH domain of the antibody expressed by hybridoma cell line TF278 (deposited Dec. 3, 2003, ATCC Deposit No. PTA-5676); (d) at least one CDR region of a VH domain of the antibody expressed by hybridoma cell line TF277 (deposited Dec. 3, 2003, ATCC Deposit No. PTA-5675); (e) at least one CDR region of a VH domain of the antibody expressed by hybridoma cell line TF392 (deposited Dec. 3, 2003, ATCC Deposit No. PTA-5677); (f) at least one CDR region of a VH domain of the antibody expressed by hybridoma cell line TF9 (deposited Dec. 3, 2003, ATCC Deposit No. PTA-5674); (g) at least two CDR regions of a VH domain of the antibody expressed by hybridoma cell line TF196; (h) at least two CDR regions of a VH domain of the antibody expressed by hybridoma cell line TF260; (i) at least two CDR regions of a VH domain of the antibody expressed by hybridoma cell line TF278: (j) at least two CDR regions of a VH domain of the antibody expressed by hybridoma cell line TF277; (k) at least two CDR regions of a VH domain of the antibody expressed by hybridoma cell line TF392; (l) at least two CDR regions of a VH domain of the antibody expressed by hybridoma cell line TF9; (m) at least three CDR regions of a VH domain of the antibody expressed by hybridoma cell line TF196; (n) at least three CDR regions of a VH domain of the antibody expressed by hybridoma cell line TF260; (o) at least three CDR regions of a VH domain of the antibody expressed by hybridoma cell line TF278: (p) at least three CDR regions of a VH domain of the antibody expressed by hybridoma cell line TF277; (q) at least three CDR regions of a VH domain of the antibody expressed by hybridoma cell line TF392; (r) at least three CDR regions of a VH domain of the antibody expressed by hybridoma cell line TF9; (s) at least one CDR region of a VL domain of the antibody expressed by hybridoma cell line TF196; (t) at least one CDR region of a VL domain of the antibody expressed by hybridoma cell line TF260; (u) at least one CDR region of a VL domain of the antibody expressed by hybridoma cell line TF278; (v) at least one CDR region of a VL domain of the antibody expressed by hybridoma cell line TF277; (w) at least one CDR region of a VL domain of the antibody expressed by hybridoma cell line TF392; (x) at least one CDR region of a VL domain of the antibody expressed by hybridoma cell line TF9; (y) at least two CDR regions of a VL domain of the antibody expressed by hybridoma cell line TF196; (z) at least two CDR regions of a VL domain of the antibody expressed by hybridoma cell line TF260; (aa) at least two CDR regions of a VL domain of the antibody expressed by hybridoma cell line TF278; (bb) at least two CDR regions of a VL domain of the antibody expressed by hybridoma cell line TF277; (cc) at least two CDR regions of a VL domain of the antibody expressed by hybridoma cell line TF392; (dd) at least two CDR regions of a VL domain of the antibody expressed by hybridoma cell line TF9; (ee) at least three CDR regions of a VL domain of the antibody expressed by hybridoma cell line TF196; (ff) at least three CDR regions of a VL domain of the antibody expressed by hybridoma cell line TF260; (gg) at least three CDR regions of a VL domain of the antibody expressed by hybridoma cell line TF278; (hh) at least three CDR regions of a VL domain of the antibody expressed by hybridoma cell line TF277; (ii) at least three CDR regions of a VL domain of the antibody expressed by hybridoma cell line TF392; and (jj) at least three CDR regions of a VL domain of the antibody expressed by hybridoma cell line TF9. In some embodiments, the first antibody, or antigen-binding fragment thereof, has the same immunospecificity, or binds the same epitope, as the second antibody.

The invention is directed to an isolated antibody, or antigen-binding fragment thereof, having an amino acid sequence at least 70%, at least 80%, at least 85%, at least 90%, or at least 95% identical to an amino acid sequence selected from the group consisting of: (a) a polypeptide of SEQ ID NO:6 or 8 or a polypeptide encoded by the cDNA sequence provided in ATCC Deposit No: PTA-5252 or PTA-5253, respectively (TF260VH/PUC18 or TF260VL/PUC18, respectively); (b) a polypeptide domain of SEQ ID NO:6 or 8 or the polypeptide encoded by the cDNA sequence provided in ATCC Deposit No: PTA-5252 or PTA-5253, respectively (TF260VH/PUC18 or TF260VL/PUC18, respectively); (c) a polypeptide epitope of SEQ ID NO:6 or 8 or the polypeptide encoded by the cDNA sequence provided in ATCC Deposit No: PTA-5252 or PTA-5253, respectively (TF260VH/

PUC18 or TF260VL/PUC18, respectively); (d) a polypeptide which is a variant of SEQ ID NO:6 or 8; (e) a polypeptide which is a species homologue of the SEQ ID NO:6 or 8; (f) a polypeptide of SEQ ID NO:10 or 12 or a polypeptide encoded by the cDNA sequence included in ATCC Deposit No: PTA-5250 or PTA-5251, respectively (TF196VH/PUC18 or TF196VL/PUC18, respectively); (g) a polypeptide domain of SEQ ID NO:10 or 12 or the polypeptide encoded by the cDNA sequence included in ATCC Deposit No: PTA-5250 or PTA-5251, respectively (TF196VH/PUC18 or TF196VL/PUC18, respectively); (h) a polypeptide epitope of SEQ ID NO:10 or 12 or the polypeptide encoded by the cDNA sequence included in ATCC Deposit No: PTA-5250 or PTA-5251, respectively (TF196VH/PUC18 or TF196VL/PUC18, respectively); (i) a polypeptide which is a variant of SEQ ID NO:10 or 12; (j) a polypeptide which is a species homologue of SEQ ID NO:10 or 12; (k) a polypeptide of SEQ ID NO:19 or 21 or a polypeptide encoded by the cDNA sequence provided in ATCC Deposit No: PTA-5694 or PTA-5695, respectively (TF278VHs/PUC18 OR TF278VLs/PUC18, respectively); (l) a polypeptide domain of SEQ ID NO:19 or 21 or the polypeptide encoded by the cDNA sequence provided in ATCC Deposit No: PTA-5694 or PTA-5695, respectively (TF278VHs/PUC18 OR TF278VLs/PUC18, respectively); (m) a polypeptide epitope of SEQ ID NO:19 or 21 or the polypeptide encoded by the cDNA sequence provided in ATCC Deposit No: PTA-5694 or PTA-5695, respectively (TF278VHs/PUC18 OR TF278VLs/PUC18, respectively); (n) a polypeptide which is a variant of SEQ ID NO:19 or 21; (o) a polypeptide which is a species homologue of the SEQ ID NO:19 or 21; (p) a polypeptide of SEQ ID NO:23 or 25; (q) a polypeptide domain of SEQ ID NO:23 or 25; (r) a polypeptide epitope of SEQ ID NO:23 or 25; (s) a polypeptide which is a variant of SEQ ID NO:23 or 25; (t) a polypeptide which is a species homologue of the SEQ ID NO:23 or 25; (u) a polypeptide of SEQ ID NO:27 or a polypeptide encoded by the cDNA sequence provided in ATCC Deposit No: PTA-5696 (TF392VHs/PUC18); (v) a polypeptide domain of SEQ ID NO:27 or the polypeptide encoded by the cDNA sequence provided in ATCC Deposit No: PTA-5696 (TF392VHs/PUC18); (w) a polypeptide epitope of SEQ ID NO:27 or the polypeptide encoded by the cDNA sequence provided in ATCC Deposit No: PTA-5696 (TF392VHs/PUC18); (x) a polypeptide which is a variant of SEQ ID NO:27; (y) a polypeptide which is a species homologue of the SEQ ID NO:27; (z) a polypeptide of SEQ ID NO:29 or 31 or a polypeptide encoded by the cDNA sequence provided in ATCC Deposit No: PTA-5692 or PTA-5693, respectively (TF9VHs/PUC18 or TF9VL/PUC18, respectively); (aa) a polypeptide domain of SEQ ID NO:29 or 31 or the polypeptide encoded by the cDNA sequence provided in ATCC Deposit No: PTA-5692 or PTA-5693, respectively (TF9VHs/PUC18 or TF9VL/PUC18, respectively); (bb) a polypeptide epitope of SEQ ID NO:29 or 31 or the polypeptide encoded by the cDNA sequence provided in ATCC Deposit No: PTA-5692 or PTA-5693, respectively (TF9VHs/PUC18 or TF9VL/PUC18, respectively); (cc) a polypeptide which is a variant of SEQ ID NO:29 or 31; and (dd) a polypeptide which is a species homologue of the SEQ ID NO:29 or 31. In some embodiments, the antibody, or antigen-binding fragment thereof, has the same immunospecificity, or binds the same epitope, as the polypeptide encoded by the amino acid sequence selected from the group consisting of SEQ ID NOs: 6, 8, 10, 12, 19, 21, 23, 25, 27, 29 and 31.

The invention also encompasses antibodies that have one or more of the same biological characteristics as one or more of the antibodies described herein. By "biological characteristics" is intended to mean the in vitro or in vivo activities or properties of the antibodies, such as, for example, the ability to bind to TF (e.g., hTF expressed on a cell surface, or membrane-embedded hTF), without inhibiting TF mediated blood coagulation compared to a normal plasma control. Optionally, the antibodies of the invention can bind to the same epitope as one of the antibodies specifically referred to herein. Such epitope binding can be routinely determined using assays known in the art.

The invention is also directed to a monoclonal antibody having the binding characteristics of, or that competes for binding to an epitope recognized by, a monoclonal antibody produced by hybridoma cell line TF260. The invention is also directed to a monoclonal antibody having the binding characteristics of, or that competes for binding to an epitope recognized by, a monoclonal antibody produced by hybridoma cell line TF196. The invention is also directed to a monoclonal antibody having the binding characteristics of, or that competes for binding to an epitope recognized by, a monoclonal antibody produced by hybridoma cell line TF278. The invention is also directed to a monoclonal antibody having the binding characteristics of, or that competes for binding to an epitope recognized by, a monoclonal antibody produced by hybridoma cell line TF277. The invention is also directed to a monoclonal antibody having the binding characteristics of, or that competes for binding to an epitope recognized by, a monoclonal antibody produced by hybridoma cell line TF392. The invention is also directed to a monoclonal antibody having the binding characteristics of, or that competes for binding to an epitope recognized by, a monoclonal antibody produced by hybridoma cell line TF9. The invention is also directed to an antibody obtainable from a hybridoma cell line TF260. The invention is also directed to an antibody obtainable from a hybridoma cell line TF196. The invention is also directed to an antibody obtainable from a hybridoma cell line TF278. The invention is also directed to an antibody obtainable from a hybridoma cell line TF277. The invention is also directed to an antibody obtainable from a hybridoma cell line TF392. The invention is also directed to an antibody obtainable from a hybridoma cell line TF9. The invention is also directed to a hybridoma cell line which produces antibodies which have the same immunospecificity, or bind the same epitope, as antibodies produced from hybridoma cell line TF260. The invention is also directed to a hybridoma cell line which produces antibodies which have the same immunospecificity, or bind the same epitope, as antibodies produced from hybridoma cell line TF196. The invention is also directed to a hybridoma cell line which produces antibodies which have the same immunospecificity, or bind the same epitope, as antibodies produced from hybridoma cell line TF278. The invention is also directed to a hybridoma cell line which produces antibodies which have the same immunospecificity, or bind the same epitope, as antibodies produced from hybridoma cell line TF277. The invention is also directed to a hybridoma cell line which produces antibodies-which have the same immunospecificity, or bind the same epitope, as antibodies produced from hybridoma cell line TF392. The invention is also directed to a hybridoma cell line which produces antibodies which have the same immunospecificity, or bind the same epitope, as antibodies produced from hybridoma cell line TF9. The invention is also directed to hybridoma cell line TF260. The invention is also directed to hybridoma cell line TF196. The invention is also directed to hybridoma cell line TF278. The invention is also directed to hybridoma cell line TF277. The invention is also directed to hybridoma cell line TF392. The invention is also directed to hybridoma cell line TF9. The invention is also directed to an antibody comprising an amino acid sequence of SEQ ID NO:6, 8, 10, 12, 19, 21, 23, 25, 27, 29, or 31. The American Type Culture Collection (ATCC) is located at 10801 University Boulevard, Manassas, Va. 20110-2209, USA.

Methods of Producing Antibodies

The antibodies of the invention can be produced by any method known in the art for the synthesis of antibodies, e.g., by chemical synthesis or by recombinant expression techniques. In other embodiments, rapid immunization of mice at multiple sites (RIMMS) can be used. See, e.g., Kilpatrick, K. E., et al., *Hybridoma* 16:381-389 (1997). In yet other embodiments, methods of producing antibodies include, but are not limited to, hybridoma technology, EBV transformation, XenoMouse™ technology (see Green et al., *Nature Genetics* 7:13-21 (1994) and other methods discussed herein as well as through the use of recombinant DNA technology, as discussed below.

The antibodies of the present invention can be generated by any suitable method known in the art. Polyclonal antibodies to an antigen of interest can be produced by various procedures well known in the art. For example, a polypeptide of interest can be administered to various host animals including, but not limited to, rabbits, mice, rats, etc. to induce the production of sera containing polyclonal antibodies specific for the antigen. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or combinations thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in *Monoclonal Antibodies and T-Cell Hybridomas*, Elsevier, New York (1981), pp. 563-681. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with a polypeptide of interest or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, e.g., mouse myeloma cells (P3X63/Ag8.653, ATCC No. CRL-1580, Manassas, Va.; SP2/0-Ag14, ATCC No. CRL-1581, Manassas, Va.; P3/NSI/1-Ag4-1 (NS-1), ATCC No. TIB-18, Manassas, Va.). Hybridomas are selected and cloned by limited dilution. The hybridoma clones are then assayed by methods known in the art for cells that secrete antibodies capable of binding a polypeptide of interest. Ascites fluid, which generally contains high levels of antibodies, can be generated by injecting mice with positive hybridoma clones.

Accordingly, the present invention provides methods of generating monoclonal antibodies as well as antibodies produced by the method comprising culturing a hybridoma cell secreting an antibody of the invention, wherein the hybridoma is generated by fusing splenocytes or lymph node cells isolated from a mammal immunized with an antigen of the invention with myeloma cells and then screening the hybridomas resulting from the fusion for hybridoma clones that secrete an antibody able to bind a polypeptide of interest.

Humanized antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654, WO 96/34096, WO 96/33735, and WO 91/10741. Additionally, antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska., et al., *PNAS* 91:969-973 (1994)), and chain shuffling (U.S. Pat. No. 5,565,332).

Human antibodies can be produced using transgenic mice that are incapable of expressing functional endogenous immunoglobulins, but which can express human immunoglobulin genes. For example, the human heavy chain and light chain immunoglobulin gene complexes can be introduced randomly or by homologous recombination into mouse embryonic stem cells. Alternatively, nucleic acids encoding the human variable region and constant region can be introduced into mouse embryonic stem cells in addition to the human heavy and light chain genes. The mouse heavy chain and light chain immunoglobulin genes can be rendered non-functional separately or simultaneously with the introduction of human immunoglobulin loci by homologous recombination. In some embodiments, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of interest. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598.

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., *Bio/technology* 12:899-903 (1988)).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). Single chain antibodies are formed by linking the heavy and light chain fragments of the Fv region via an amino acid bridge, resulting in a single chain polypeptide. Techniques for the assembly of functional Fv fragments in *E. coli* can also be used (Skerra et al., *Science* 242:1038-1041 (1988)).

In addition, methods for producing chimeric antibodies are known in the art. See e.g., Morrison, *Science* 229:1202 (1985); Oi et al., *BioTechniques* 4:214 (1986); Gillies et al., *J. Immunol. Methods* 125:191-202 (1989); Neuberger et al., *Nature* 312:604-608 (1984); Takeda et al., *Nature* 314:452-454 (1985); U.S. Pat. Nos. 5,807,715; 4,816,567; and 4,816,397.

Once an antibody molecule of the invention has been produced by an animal, chemically synthesized, or recombinantly expressed, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Nucleic Acid Molecules Encoding Antibodies and Polypeptides thereof

The present invention further provides an isolated polynucleotide molecule having a nucleotide sequence encoding an antibody of the invention. In some embodiments, the isolated polynucleotide molecule comprises a nucleotide sequence of SEQ ID NO:5, 7, 9, or 11 (as provided in TF260VH/PUC18, TF260VL/PUC18, TF196VH/PUC18, or TF196VL/PUC18, respectively, deposited Jun. 6, 2003 as ATCC Deposit Nos: PTA-5252, PTA-5253, PTA-5250, or PTA-5251, respectively, or a nucleotide sequence of SEQ ID NO:18, 20, 26, 28, or 30 (as provided in TF278VHs/PUC18, TF278VLs/PUC18, TF392VHs/PUC18, TF9VHs/PUC18 or TF9VL/PUC18, respectively, deposited Dec. 9, 2003 as ATCC Deposit Nos: PTA-5694, PTA-5695, PTA-5696, PTA-5692, or PTA-5693, respectively), or a nucleotide sequence of SEQ ID NO:22 or 24 or a nucleotide sequence encoding an amino acid sequence of SEQ ID NO:6, 8, 10, 12 (as encoded by TF260VH/PUC18, TF260VL/PUC18, TF196VH/PUC18, or TF196VL/PUC18, respectively, deposited Jun. 6, 2003 as ATCC Deposit No: PTA-5252, PTA-5253, PTA-5250, or PTA-5251, respectively), 19, 21, 27, 29, 31 (as encoded by TF278VHs-PUC18, TF278VLs-PUC18, TF392VHs-PUC18, TF9VHs-PUC18 or TF9VL-PUC18, respectively, deposited on Dec. 9, 2003, as ATCC Deposit No: PTA-5694, PTA-5695, PTA-5696, PTA-5692 or PTA-5693, respectively), 23 or 25 (including degenerate variants), or fragments or variants thereof.

The invention is further directed to an isolated polynucleotide having a nucleotide sequence encoding a first antibody, or antigen-binding fragment thereof, having an amino acid sequence that is at least 70%, at least 80%, at least 85%, at least 90%, at least 95%, at least 96%, at least 97%, at least 98%, or at least 99% identical to the amino acid sequence of a second antibody comprising an amino acid sequence selected from the group consisting of: (a) at least one CDR region of a VH domain of the antibody expressed by hybridoma cell line TF196; (b) at least one CDR region of a VH domain of the antibody expressed by hybridoma cell line TF260; (c) at least one CDR region of a VH domain of the antibody expressed by hybridoma cell line TF278; (d) at least one CDR region of a VH domain of the antibody expressed by hybridoma cell line TF277; (e) at least one CDR region of a VH domain of the antibody expressed by hybridoma cell line TF392; (f) at least one CDR region of a VH domain of the antibody expressed by hybridoma cell line TF9; (g) at least two CDR regions of a VH domain of the antibody expressed by hybridoma cell line TF196; (h) at least two CDR regions of a VH domain of the antibody expressed by hybridoma cell line TF260; (i) at least two CDR regions of a VH domain of the antibody expressed by hybridoma cell line TF278; (j) at least two CDR regions of a VH domain of the antibody expressed by hybridoma cell line TF277; (k) at least two CDR regions of a VH domain of the antibody expressed by hybridoma cell line TF392; (l) at least two CDR regions of a VH domain of the antibody expressed by hybridoma cell line TF9; (m) at least three CDR regions of a VH domain of the antibody expressed by hybridoma cell line TF196; (n) at least three CDR regions of a VH domain of the antibody expressed by hybridoma cell line TF260; (o) at least three CDR regions of a VH domain of the antibody expressed by hybridoma cell line TF278; (p) at least three CDR regions of a VH domain of the antibody expressed by hybridoma cell line TF277; (q) at least three CDR regions of a VH domain of the antibody expressed by hybridoma cell line TF392; (r) at least three CDR regions of a VH domain of the antibody expressed by hybridoma cell line TF9; (s) at least one CDR region of a VL domain of the antibody expressed by hybridoma cell line TF196; (t) at least one CDR region of a VL domain of the antibody expressed by hybridoma cell line TF260; (u) at least one CDR region of a VL domain of the antibody expressed by hybridoma cell line TF278; (v) at least one CDR region of a VL domain of the antibody expressed by hybridoma cell line TF277; (w) at least one CDR region of a VL domain of the antibody expressed by hybridoma cell line TF392; (x) at least one CDR region of a VL domain of the antibody expressed by hybridoma cell line TF9; (y) at least two CDR regions of a VL domain of the antibody expressed by hybridoma cell line TF196; (z) at least two CDR regions of a VL domain of the antibody expressed by hybridoma cell line TF260; (aa) at least two CDR regions of a VL domain of the antibody expressed by hybridoma cell line TF278; (bb) at least two CDR regions of a VL domain of the antibody expressed by hybridoma cell line TF277; (cc) at least two CDR regions of a VL domain of the antibody expressed by hybridoma cell line TF392; (dd) at least two CDR regions of a VL domain of the antibody expressed by hybridoma cell line TF9; (ee) at least three CDR regions of a VL domain of the antibody expressed by hybridoma cell line TF196; (ff) at least three CDR regions of a VL domain of the antibody expressed by hybridoma cell line TF260; (gg) at least three CDR regions of a VL domain of the antibody expressed by hybridoma cell line TF278; (hh) at least three CDR regions of a VL domain of the antibody expressed by hybridoma cell line TF277; (ii) at least three CDR regions of a VL domain of the antibody expressed by hybridoma cell line TF392; and (jj) at least three CDR regions of a VL domain of the antibody expressed by hybridoma cell line TF9. In some embodiments, the first antibody, or antigen-binding fragment thereof, has the same immunospecificity, or binds the same epitope, as the second antibody.

The invention is further directed to an isolated polynucleotide having a nucleotide sequence at least 70%, at least 80%, at least 85%, at least 90%, at least 95%, at least 96%, at least 97%, at least 98%, or at least 99% identical to a nucleotide sequence encoding the amino acid sequence selected from the group consisting of: (a) at least one CDR region of a VH domain of the antibody expressed by hybridoma cell line TF196; (b) at least one CDR region of a VH domain of the antibody expressed by hybridoma cell line TF260; (c) at least one CDR region of a VH domain of the antibody expressed by hybridoma cell line TF278; (d) at least one CDR region of a VH domain of the antibody expressed by hybridoma cell line TF277; (e) at least one CDR region of a VH domain of the antibody expressed by hybridoma cell line TF392; (f) at least one CDR region of a VH domain of the antibody expressed by hybridoma cell line TF9; (g) at least two CDR regions of a VH domain of the antibody expressed by hybridoma cell line TF196; (h) at least two CDR regions of a VH domain of the antibody expressed by hybridoma cell line TF260; (i) at least two CDR regions of a VH domain of the antibody expressed by hybridoma cell line TF278; (j) at least two CDR regions of a VH domain of the antibody expressed by hybridoma cell line TF277; (k) at least two CDR regions of a VH domain of the antibody expressed by hybridoma cell line TF392; (l) at least two CDR regions of a VH domain of the antibody expressed by hybridoma cell line TF9; (m) at least three CDR regions of a VH domain of the antibody expressed by hybridoma cell line TF196; (n) at least three CDR regions of a VH domain of the antibody expressed by hybridoma cell line TF260; (o) at least three CDR regions of a VH domain of the antibody expressed by hybridoma cell line TF278; (p) at least three CDR regions of a VH domain of the antibody expressed by hybridoma cell line TF277; (q) at least three CDR regions of a VH domain of the antibody expressed by hybridoma cell line TF392; (r) at least three CDR regions of a VH domain of the antibody expressed by hybridoma cell line TF9; (s) at least one CDR region of a VL domain of the antibody expressed by hybridoma cell line TF196; (t) at least one CDR region of a VL domain of the antibody expressed by hybridoma cell line TF260; (u) at least one CDR region of a VL domain of the antibody expressed by hybridoma cell line TF278; (v) at least one CDR region of a VL domain of the antibody expressed by hybridoma cell line TF277; (w) at least one CDR region of a VL domain of the antibody expressed by hybridoma cell line TF392; (x) at least one CDR region of a VL domain of the antibody expressed by hybridoma cell line TF9; (y) at least two CDR regions of a VL domain of the antibody expressed by hybridoma cell line TF196; (z) at least two CDR regions of a VL domain of the antibody expressed by hybridoma cell line TF260; (aa) at least two CDR regions of a VL domain of the antibody expressed by hybridoma cell line TF278; (bb) at least two CDR regions of a VL domain of the antibody expressed by hybridoma cell line TF277; (cc) at least two CDR regions of a VL domain of the antibody expressed by hybridoma cell line TF392; (dd) at least two CDR regions of a VL domain of the antibody expressed by hybridoma cell line TF9; (ee) at least three CDR regions of a VL domain of the antibody expressed by hybridoma cell line TF196; (ff) at least three CDR regions of a VL domain of the antibody expressed by hybridoma cell line TF260; (gg) at least three CDR regions of a VL domain of the antibody expressed by hybridoma cell line TF278; (hh) at least three CDR regions of a VL domain of the antibody expressed by hybridoma cell line TF277; (ii) at least three CDR regions of a VL domain of the antibody expressed by hybridoma cell line TF392; and (jj) at least three CDR regions of a VL domain of the antibody expressed by hybridoma cell line TF9. In some embodiments, the isolated polynucleotide encodes an amino acid sequence which further encodes an antibody, or antigen-binding fragment thereof, having a CDR region with the same immunospecificity, or binds the same epitope, as either a VH domain or VL domain of an antibody of the present invention.

The present invention is further directed to a polynucleotide molecule having a nucleotide sequence encoding an antigen-binding antibody fragment that binds to hTF without inhibiting normal TF mediated blood coagulation compared to a normal plasma control, and optionally, can initiate an Fc-mediated mechanism. The present invention is further directed to an isolated polynucleotide molecule having a nucleotide sequence that can hybridize under stringent conditions to the complement of the nucleotide sequence of SEQ ID NO:5, 7, 9, 11, 18, 20, 22, 24, 26, 28, or 30 and that encodes a polypeptide that can bind to hTF without inhibiting normal TF mediated blood coagulation compared to a normal plasma control, and optionally, can initiate an Fc-mediated mechanism. The present invention is further directed to an isolated polynucleotide molecule comprising a nucleotide sequence that has at least 95%, at least 96%, at least 97%, at least 98%, or at least 99% sequence identity to any of SEQ ID NO:5, 7, 9, 11, 18, 20, 22, 24, 26, 28, or 30 and encodes a polypeptide that can bind to hTF without inhibiting normal TF mediated blood coagulation compared to a normal plasma control, and optionally, can initiate an Fc-mediated mechanism.

As known in the art, "sequence identity" between two nucleotide sequences is determined by comparing the nucleotide sequence of one polynucleotide molecule to the sequence of a second polynucleotide molecule. When discussed herein, whether any particular nucleotide sequence is identical to another nucleotide sequence can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, *Advances in Applied Mathematics* 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of nucleic acids in the reference sequence are allowed.

As used herein "stringent conditions" refer to the ability of a first polynucleotide molecule to hybridize, and remain bound to, a second, filter-bound polynucleotide molecule in 0.5 M NaHPO$_4$, 7% sodium dodecyl sulfate (SDS), and 1 mM EDTA at 65° C., followed by washing in 0.2×SSC/0.1% SDS at 42° C. (see Ausubel et al. (eds.), *Current Protocols in Molecular Biology*, Vol. 1, Green Publishing Associates, Inc., and John Wiley & Sons, Inc., New York (1989), at p. 2.10.3).

The invention is also directed to a recombinant vector comprising an isolated polynucleotide of the present invention, and a host cell comprising the vector. Host cells are genetically engineered (transduced, transformed or transfected) with a vector of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, can be those previously used with the host cell selected for expression, and will be apparent to the ordinarily skilled artisan.

The invention is further directed to a method of making an antibody of the invention comprising: (a) expressing the antibody encoded by the isolated polynucleotide of the invention; and (b) recovering the antibody.

Fragments or portions of the polypeptides of the present invention can be employed for producing the corresponding full-length polypeptide by peptide synthesis; therefore, the fragments can be employed as intermediates for producing the full-length polypeptides. Fragments or portions of the polynucleotides of the present invention can be used to synthesize fill-length polynucleotides of the present invention.

The polynucleotide molecules of the present invention can be employed for producing polypeptides by recombinant techniques. Thus, for example, a polynucleotide molecule can be included in any one of a variety of expression vectors for expressing a polypeptide. Such vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector can be used as long as it is replicable and viable in the host.

The appropriate DNA sequence can be inserted into a vector by a variety of procedures. In general, the DNA sequence is inserted into an appropriate restriction endonuclease site(s) in a vector by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there can be mentioned: LTR or SV40 promoter, the $E.$ $coli$ lac or trp, the phage lambda $P_L$ promoter and other promoters known to control expression of genes in prokaryotic or eukaryotic cells or their viruses. The expression vector also should contain a ribosome binding site for translation initiation, and a transcription terminator. The vector can also include appropriate sequences for amplifying expression, as discussed infra.

In addition, the expression vectors can contain one or more selectable marker genes to provide a phenotypic trait for selection of transformed host cells such as dihydrofolate reductase or neomycin resistance for eukaryotic cell culture, or tetracycline or ampicillin resistance in $E.$ $coli$.

The vector containing the appropriate DNA sequence as hereinabove described, as well as an appropriate promoter or control sequence, can be employed to transform an appropriate host cell to permit the host cell to express the protein. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector can be used as long as they are replicable and stable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retroviruses, and mouse metallothionein-I. Selection of the appropriate vector and promoter is well within the level of ordinary skill in the art. Promoters can be derived from operons encoding glycolytic enzymes such as 3-phosphoglycerate kinase (PGK), α-factor, acid phosphatase, or heat shock proteins, among others. The heterologous structural sequence to be expressed is assembled in appropriate phase with translation initiation and termination sequences, and, if necessary, a leader sequence capable of directing secretion of translated protein into the periplasmic space or extracellular medium. Optionally, the heterologous sequence can encode a fusion protein including an N-terminal or C-terminal identification peptide imparting desired characteristics, e.g., stabilization or simplified purification of expressed recombinant product.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by any suitable techniques, such as, e.g., calcium phosphate transfection, DEAE-Dextran mediated transfection, or electroporation among others. (Davis, L., et al., *Basic Methods in Molecular Biology*, (1986)).

As representative examples of appropriate hosts, there can be mentioned: bacterial cells, such as *E. coli, Streptomyces, Salmonella typhimurium*; fungal cells, such as yeast; insect cells such as *Drosophila* and *Spodoptera* Sf9; animal cells such as CHO, COS or Bowes melanoma; plant cells, etc. The selection of an appropriate host is deemed to be within the scope of those skilled in the art from the teachings herein. Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites can be used to provide the required nontranscribed genetic elements.

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual, Second Edition*, Cold Spring Harbor, N.Y., (1989).

Transcription of the DNA encoding the polypeptides of the present invention by higher eukaryotes can be increased by inserting an enhancer sequence into the vector. Enhancers are cis-acting elements of DNA, usually about from 10 to 300 bp that act on a promoter to increase its transcription or amplifying expression. Examples include the SV40 enhancer on the late side of the replication origin bp 100 to 270, a cytomegalovirus early promoter enhancer, the polyoma enhancer on the late side of the replication origin, and adenovirus enhancers.

Following transformation of a suitable host strain and growth of the host strain to an appropriate cell density, the selected promoter can be induced by appropriate means (e.g., temperature shift or chemical induction) and the cells are cultured for an additional period.

Where the desired protein is retained intracellularly, cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or a combination thereof. Such methods are well known to those skilled in the art.

The polypeptides of the invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention can be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptide of the present invention can be glycosylated or can be non-glycosylated. Polypeptides of the invention can also include an initial methionine amino acid residue.

Antibody Conjugates

Antibodies of the present invention can be used to purify, detect, and/or target hTF, including in both in vitro and in vivo diagnostic and therapeutic methods. For example, the antibodies can be useful in immunoassays for qualitatively and quantitatively measuring levels of hTF in biological samples. See, e.g., Harlow et al., *Antibodies: A Laboratory Manual* (Cold Spring Harbor Laboratory Press, 2nd ed. 1988).

The antibodies of the invention include derivatives of antibodies that are modified or conjugated by the covalent attachment of any type of molecule to the antibody. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc. Additionally, the derivatives can contain one or more non-classical amino acids.

Antibodies of the present invention can be used for epitope mapping to identify the epitope(s) bound by the antibody. Epitopes identified in this way can, in turn, be used as vaccine candidates, i.e., to immunize an individual to elicit antibodies against the naturally occurring forms of hTF.

The antibodies of the present invention can be used either alone or in combination with other compositions. The antibodies can be recombinantly fused to a heterologous polypeptide at the N- or C-terminus or chemically conjugated (including covalent and non-covalent conjugations) to polypeptides or other compositions. For example, antibodies of the present invention can be recombinantly fused or conjugated to molecules useful as labels in detection assays, or as effector molecules such as heterologous polypeptides, drugs, radionuclides, or toxins. See, e.g., PCT publications WO 92/08495; WO 91/14438; WO 89/12624; U.S. Pat. No. 5,314, 995; and EP 0 396 387.

In some embodiments, the antibody of the invention is conjugated to cytotoxic agents. A "cytotoxic agent" is any agent toxic or otherwise detrimental to cells. Examples include, but are not limited to, a radionuclide, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Examples of radionuclides useful as cytotoxic agents include, but are not limited to, $^{131}I$, $^{177}Lu$, $^{90}Y$, and $^{186}Re$.

The present invention also encompasses antibodies of the invention conjugated to detectable agents, wherein the detectable agents can be used for diagnosis or therapeutic purposes. The antibodies can be used diagnostically to, for example, locate or monitor the development or progression of a tumor as part of a clinical testing procedure to, e.g., determine the efficacy of a given treatment regimen. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate (such as, for example, a linker known in the art) using techniques known in the art. See, for example, U.S. Pat. No. 4,741,900 for metal ions that can be conjugated to antibodies for use as diagnostics according to the present invention. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferase, luciferin, and aequorin; and examples of suitable radioactive material include iodine ($^{121}I$, $^{123}I$, $^{125}I$, $^{131}I$), carbon ($^{14}C$), sulfur ($^{35}S$), tritium ($^{3}H$), indium ($^{111}In$, $^{112}In$, $^{113m}In$, $^{115m}In$), technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, and $^{97}Ru$.

In other embodiments, the antibody of the invention can be conjugated to a therapeutic agent. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), and radionuclides. Examples of radionuclides useful as therapeutic agents include, but are not limited to, $^{131}$I, $^{177}$Lu, $^{90}$Y, and $^{186}$Re.

Techniques for conjugating such therapeutic moieties to antibodies are well-known, see, e.g., Arnon et al., "Monoclonal Antibodies For Immunotargeting Of Drugs In Cancer Therapy," in *Monoclonal Antibodies And Cancer Therapy*, Reisfeld et al., eds., Alan R. Liss, Inc. (1985), pp. 243-256; Hellstrom et al., "Antibodies For Drug Delivery," in *Controlled Drug Delivery*, 2nd Ed., Robinson et al., eds., Marcel Dekker, Inc. (1987), pp. 623-653; Thorpe, "Antibody Carriers Of Cytotoxic Agents In Cancer Therapy: A Review," in *Monoclonal Antibodies '84: Biological And Clinical Applications*, Pinchera et al., eds. (1985), pp. 475-506; "Analysis, Results, And Future Prospective Of The Therapeutic Use Of Radiolabeled Antibody In Cancer Therapy," in *Monoclonal Antibodies For Cancer Detection And Therapy*, Baldwin et al., eds., Academic Press (1985), pp. 303-316; and Thorpe et al., "The Preparation And Cytotoxic Properties of Antibody-Toxin Conjugates," *Immunol. Rev.* 62:119-158 (1982).

Figure 2:
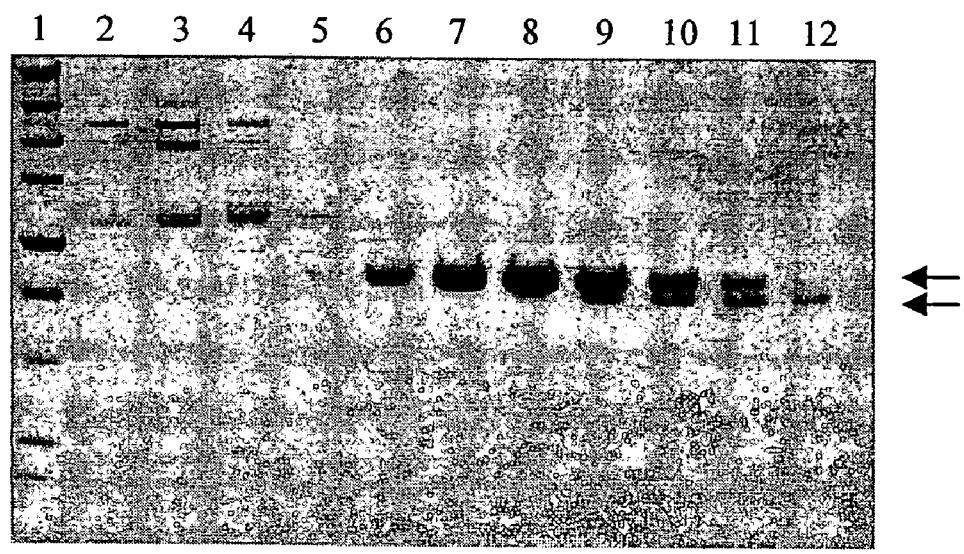
FIG. 2. Purification of hTF using gel-filtration chromatography. Lane 1 contains molecular weight markers. Lanes 2-12 are fractions eluted from the gel filtration column. Fractions with protein bands as in lanes 6 to 12 were pooled. Both bands (arrow indicated) are soluble hTF as demonstrated by Western-blot analysis.
Figure 3A:
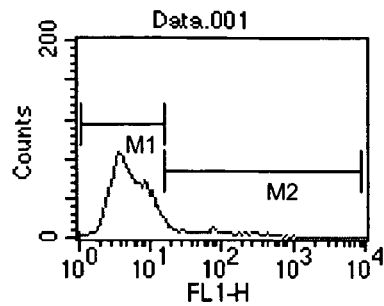
FIGS. 3A-3C. FACS analysis of selected hTF stable cell clones. FACS analysis was carried out with a commercial anti-TF antibody (10 μg/ml, Calbiochem, Calif., Cat. #612161) as the first antibody and a FITC-labeled goat anti-mouse IgG (1:50 dilution, Southern Biotechnology, AL) as the second antibody. The fluorescence intensities of the antibody stained cells were measured on a flow cytometer (FAC-Scan, Becton Dickinson, N.J.) and analyzed using Cell Quest software (Becton Dickinson, N.J.).
Figure 3B:
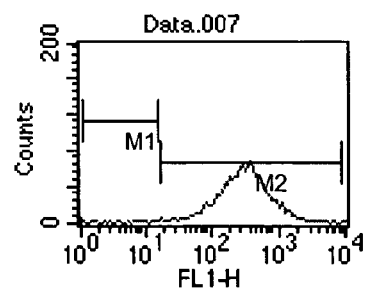
Figure 3C:
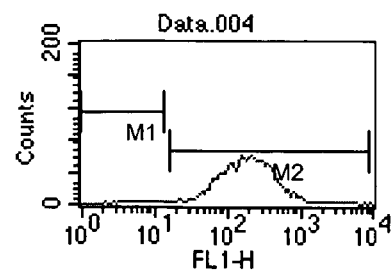

The present invention encompasses antibodies of the invention recombinantly fused or chemically conjugated (including both covalent and non-covalent conjugations) to a polypeptide of interest to generate fusion proteins. The fusion does not necessarily need to be direct, but can occur through linker sequences. The antibodies of the present invention can be fused to either the N- or C-terminus of the heterologous protein (e.g., immunoglobulin Fc polypeptide or human serum albumin polypeptide). For example, antibodies can be fused to albumin, such as recombinant human serum albumin (see, e.g., U.S. Pat. No. 5,876,969, EP 0 413 622, and U.S. Pat. No. 5,766,883)), resulting in a chimeric polypeptide. In other embodiments, antibodies can be fused to the mature form of human serum albumin (i.e., amino acids 1-585 of human serum albumin as shown in FIGS. 1 and 2 of EP Patent 0 322 094). In other embodiments, antibodies can be fused with polypeptide fragments comprising, or alternatively consisting of, amino acid residues 1-z of human serum albumin, where z is an integer from 369 to 419, as described in U.S. Pat. No. 5,766,883. Antibodies fused or conjugated to polypeptides or other molecules of interest can also be used in in vitro immunoassays and purification methods using methods known in the art. See e.g., Harbor et al., supra, and PCT publication WO 93/21232; EP 439,095; Naramura et al., *Immunol. Lett.* 39:91-99 (1994); U.S. Pat. No. 5,474,981; Gillies et al., *PNAS* 89:1428-1432 (1992); and Fell et al., *J. Immunol.* 146:2446-2452(1991).

The antibodies can be fused to marker sequences, such as a peptide to facilitate purification. In some embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)), and the "flag" tag (Stratagene, Calif.).

While the antibody conjugates of the invention can be used for modifying a given biological response, the therapeutic agent or drug moiety is not to be construed as being limited to classical chemical therapeutic agents. For example, the drug moiety can be a protein or polypeptide possessing a desired biological activity. Such proteins can include, for example, a toxin such as *abrin*, ricin A, *pseudomonas* exotoxin, or diphtheria toxin; a protein such as tumor necrosis factor, α-interferon, β-interferon, nerve growth factor, platelet derived growth factor, tissue plasminogen activator, an apoptotic agent, e.g., TNF-alpha, TNF-beta, AIM I (see, WO 97/33899), AIM II (see, WO 97/34911), Fas Ligand (Takahashi et al., *Int. Immunol.* 6:1567-1574 (1994)), VEGI (see, WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies of the invention can also be attached to solid supports, which are useful for immunoassays or purification of the target antigen. Such solid supports include, but are not limited to, glass, cellulose, polyacrylamide, nylon, polystyrene, polyvinyl chloride and polypropylene.

Alternatively, the antibody of the invention can be conjugated to a second antibody to form an antibody heteroconjugate as described, e.g., in U.S. Pat. No. 4,676,980.

Assays for Antibody Binding

The antibodies of the invention can be assayed for immunospecific binding by any suitable method known in the art. The immunoassays that can be used include but are not limited to competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see e.g., Ausubel et al, eds, *Current Protocols in Molecular Biology*, Vol. 1, John Wiley & Sons, Inc., New York (1994)). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols, see e.g., Ausubel et al., eds, Current Protocols in Molecular Biology, Vol. 1, John Wiley & Sons, Inc., New York (1994), at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylarnide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in incubating buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in incubating buffer, washing the membrane in wash buffer, and detecting the presence of the antigen. One of skill in the art would be knowledgeable as to the parameters that can be modified to increase the signal detected and to reduce the background noise. For further discussion regarding Western blot protocols, see e.g., Ausubel et al., eds, *Current Protocols in Molecular Biology*, Vol. 1, John Wiley & Sons, Inc., New York (1994) at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound can be added to the well. Further, instead of coating the well with the antigen, the antibody can be coated to the well. In this case, a second antibody conjugated to a detectable compound can be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, *Current Protocols in Molecular Biology*, Vol. 1, John Wiley & Sons, Inc., New York (1994) at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3H$ or $^{125}I$), or fragment or variant thereof, with the antibody of interest in the presence of increasing amounts of unlabeled antigen, and the detection of the antibody bound to the labeled antigen. The affinity of the antibody of interest for hTF and the binding off-rates can be determined from the data by Scatchard plot analysis. Competition with a second antibody can also be determined using radioimmunoassays. In this case, the hTF is incubated with the antibody of interest conjugated to a labeled compound (e.g., compound labeled with $^3H$ or $^{125}I$) in the presence of increasing amounts of an unlabeled second antibody. This kind of competitive assay between two antibodies can also be used to determine if two antibodies bind the same or different epitopes.

Blood Coagulation

Blood coagulation is a complex process involving three interacting components: blood vessels, blood coagulation factors, and blood platelets. Blood coagulation factors are proteins or glycoproteins present in the blood as inactive precursors. When bleeding occurs, the coagulation cascade is initiated and the inactive coagulation factors are converted to active proteases or enzymes.

Coagulation factors are activated in sequence in the coagulation cascade, with the aid of cofactors (such as calcium, TF, and phospholipids), resulting in the eventual formation of a fibrin clot. Fibrin is a sticky, thread-like protein that is insoluble in blood and provides the foundation for platelet adhesion and blood coagulation.

If bleeding results from an injury outside of the vasculature (such as an abrasion or cut of the skin), the extrinsic pathway is initiated. If injury occurs within the blood vessel itself, the intrinsic pathway is activated. Many bleeding episodes activate both pathways.

The extrinsic coagulation pathway is triggered on the extravascular cell surface when TF is exposed to blood following some physical injury. TF is a protein that can bind to both activated and inactivated forms of factor VII. In the extrinsic pathway, a small amount of circulating activated factor VII (factor VIIa) complexes with TF following its release. This TF/factor VIIa complex initiates coagulation by converting factors IX and X to active forms.

This reaction is amplified by a feedback mechanism in which factors VIIa, IXa and Xa activate additional factor VII bound to TF. Factor Xa, in complex with a cofactor, factor Va, and phospholipids, continues in the cascade activating prothrombin (also known as factor II) to thrombin (also known as factor IIa). Another feedback mechanism involving thrombin works to activate factors V, VIII and XI. Factor VIIIa complexes with factor IXa on platelet surfaces to activate factor X, resulting in more local thrombin generation. Thrombin is responsible for the eventual generation of fibrin.

In the intrinsic pathway, circulating activated factor XII, in complex with high molecular weight kininogen and prekallikrein, comes into contact with the exposed subendothelial membrane to initiate coagulation and activate factor XI. Factor XIa complexes with calcium to activate factor IX. Factor IXa, in conjunction with factor VIIIa, calcium and phospholipids, results in the activation of factor X to factor Xa and subsequent thrombin generation. After activation of factor X, the extrinsic and intrinsic pathways merge.

The final step of clot formation is the conversion of plasma soluble fibrinogen to insoluble fibrin as a result of the cleavage of peptide bonds. Cleavage occurs as the result of the proteolytic enzyme thrombin, which is produced from prothrombin. Conversion of prothrombin to thrombin requires a number of proteins called clotting factors, in addition to calcium. The fibrin clot is a crosslinked matrix, which entraps the formed elements of the blood thereby sealing off the site of bleeding. Formed elements consist of platelets, white blood cells, and red blood cells.

TF is a cell-anchored component that, together with factor VIIa, initiates blood coagulation in vivo. TF is a transmembrane glycoprotein with a 219 residue extracellular region, a 23 residue transmembrane region and a 21 residue cytoplasmic region. The extracellular region of TF has two fibronectin III-like domains and a distribution of disulfide bridges characteristic of class-II cytokine and interferon receptors. The cytoplasmic region of TF is short but contains at least one serine residue that can be phosphorylated. TF is also known as thromboplastin, factor III, and CD142.

TF forms a tight complex ($K_d$-pmol) with its native ligand, i.e., factor VIIa. In the complex, VIIa wraps around TF (Banner, D. W., et al., *Nature* 380:41-46 (1996)) and forms an extensive region of contact with the TF surface. TF binds and allosterically activates factor VIIa (fVIIa) and the complex TF/fVIIa is responsible for thrombin generation via activation of factors IX and X and is the major initiator of blood clotting under physiological conditions. Antibodies that bind to the TF-VIIa interaction site can inhibit TF-VIIa interaction, thus inhibiting or blocking blood coagulation. The antibodies of the present invention bind to TF, e.g., hTF, but do not inhibit TF mediated blood coagulation compared to a normal plasma control.

As used herein, the term "normal plasma control" means plasma pooled from normal human donors, such as that offered by George King Bio-Medical, Inc., Kansas (POOLED NORMAL PLASMA).

In some embodiments, the effect an antibody of the invention has on TF mediated blood coagulation can be determined using a blood clotting assay. For example, blood clotting assays known in the art, such as those described in, e.g., Morrissey, J. H., et al., *Thrombosis Research* 52:247-261 (1988), and Fang, C. H., et al., *Thrombosis and Haemostasis* 76:361-368 (1996), can be used to determine the effect of an anti-TF antibody on blood coagulation. Other blood clotting assays include, but are not limited to, one-stage prothrombin time assay (Miale J. B., *Laboratory Medicine, Hematology*, CN Mosbey Co., St. Louis (1977), and two-stage clotting assay (Bach et al., *Biochemistry* 15:4007-20 (1986)) can also be used.

An antibody of the invention "does not inhibit TF mediated blood coagulation compared to a normal plasma control" where, in an hTF coagulation assay conducted as described in the Example section below, the clotting time of a blood sample treated with the antibody is about 150% or less, about 140% or less, about 130% or less, about 120% or less, about 110% or less, or about 100% or less of the clotting time of a normal plasma control.

Fc-Mediated Mechanisms

In some embodiments, the antibodies of the invention which are capable of binding to hTF without inhibiting TF mediated blood coagulation compared to a normal plasma control, can initiate one or more Fc-mediated mechanisms.

When antibodies are exposed to proteolytic enzymes such as papain or pepsin, several major fragments are produced. The fragments that retain antigen-binding ability consist of the two "arms" of the antibody's Y configuration and are termed F(ab) (fragment-antigen binding) or F(ab')$_2$ which represent two Fab arms linked by disulfide bonds. The other major fragment produced constitutes the single "tail" or central axis of the Y and is termed Fc (fragment-crystalline) for its propensity to crystallize from solution. The Fc fragment of IgG, IgA, IgM, or IgD consists of dimers of the two carboxyl-terminal domains of each antibody (i.e., CH2 and CH3 in IgG, IgA and IgD, and CH3 and CH4 in IgM). The IgE Fc fragment, by contrast, consists of a dimer of its three-carboxyl-terminal heavy chain domains (C2, C3 and C4).

The Fc fragment contains the antibody's biologically "active site," which enables the antibody to "communicate" with other immune system molecules or cells and thereby activate and regulate immune system defensive functions or host-mediated mechanisms. Such communication occurs when active sites within the antibody Fc region binds to molecules termed Fc receptors. Fc receptors are molecules that bind with high affinity and specificity to active sites within immunoglobulin Fc regions. Fc receptors can exist as integral membrane proteins within a cell's outer plasma membrane or can exist as free, "soluble" molecules that freely circulate in blood plasma or other body fluids.

For each of the five antibody classes, there are several types of Fc receptors that specifically bind to the Fc region of that class and perform distinct functions. Thus, IgE Fc receptors bind with high affinity to only IgE Fc regions or to isolated IgE Fc fragments. It is known that different types of class-specific Fc receptors exist, which recognize and bind to different locations within the Fc region. For example, certain IgG Fc receptors bind exclusively to the second constant domain of IgG (CH2), while Fc receptors mediating other immune functions bind exclusively to IgG's third constant domain (CH3). Other IgG Fc receptors bind to active sites located in both CH2 and CH3 domains and are unable to bind to a single, isolated domain.

Many of the functions of antibodies are mediated through their interaction with Fc receptors. These receptors are found on a variety of cells including macrophages, other leukocytes, platelets and placental trophoblasts.

After antibodies bind to antigens or are otherwise caused to aggregate, active sites within the Fc region are able to bind to and activate Fc receptors, providing a critical link between antibodies and the rest of the immune system. Fc binding to Fc receptors can thus be characterized as the "final common pathway" by which antibody functions are mediated. If an antigen-bound antibody does not bind to an Fc receptor, the antibody is unable to activate the other portions of the immune system and is therefore rendered functionally inactive.

The Fc region of the immunoglobulin binds to the Fc receptor and the complex can trigger a variety of responses depending on cell type. In the case of macrophages, the response can include phagocytosis and antibody-dependent cell-mediated cytotoxicity (ADCC). Once activated by the binding of antibody Fc region active sites, Fc receptors mediate a variety of important immune killing and regulatory functions. For example, certain IgG Fc receptors mediate direct killing of cells to which the antibody has bound via its Fab arms (antibody-dependent cell-mediated cytotoxicity (ADCC)). Other IgG Fc receptors, when occupied by IgG, stimulate certain white blood cells to engulf and destroy bacteria, viruses, cancer cells or other entities by a process known as phagocytosis. Fc receptors on certain types of white blood cells known as B lymphocytes regulate their growth and development into antibody-secreting plasma cells.

Depending upon the particular type of Fc receptor to which an Fc portion of an antibody or active peptide fragment thereof binds, the peptide can either initiate or inhibit immune functions. Initiation can occur if the Fc receptor is of the type that becomes activated by the act of binding to an Fc region or, alternatively, if an Fc active site peptide stimulates the receptor. The type of initiation produced can include, but is not limited to, functions directly or indirectly mediated by antibody Fc region-Fc receptor binding.

The ability to initiate immune system functions, including those listed above, is known to be therapeutically useful in treating diseases such as infectious diseases caused by bacteria, viruses or fungi, conditions in which the immune system is deficient due either to congenital or acquired conditions, cancer and many other afflictions of human beings or animals. Such immunostimulation is also useful to boost the body's protective cellular and antibody response to certain injected or orally administered substances administered as vaccines. This list is not intended to be all-inclusive, but merely provides representative examples of diseases or conditions in which immune stimulation has a recognized therapeutic usefulness.

As used herein, the term "Fc-mediated mechanism" refers to the initiation of an immune response to foreign antigens, mediated through Fc receptor activation. Fc-mediated mechanisms include, but are not limited to, antibody-dependent cell-mediated cytotoxicity (ADCC) and complement-dependent cytotoxicity (CDC).

In some embodiments, where the antibody of the invention can initiate Fc-mediated mechanisms, that mechanism is antibody-dependent cell-mediated cytotoxicity (ADCC). In yet other embodiments, the antibody of the invention can initiate complement-dependent cytotoxicity (CDC).

Antibody-dependent cell-mediated cytotoxicity or antibody-dependent cellular cytotoxicity (ADCC) is a process by which natural killer cells, T lymphocytes, monocytes/macrophages and polymorphonuclear neutrophils (effector cells) are triggered to destroy foreign or infectious cells. IgG antibodies must first bind to antigens on the target cell, which sensitizes the cell for recognition by cells that mediate ADCC. Upon encounter with an IgG-sensitized target, IgG Fc receptors on cells that mediate ADCC bind to exposed Fc regions on the surface of the target cell. Such Fc receptor binding activates cells that mediate ADCC to directly lyse the target cell, causing its death. ADCC includes, but is not limited to, stimulation of phagocytosis by certain classes of white blood cells (polymorphonuclear neutrophils, monocytes and macrophages); macrophage activation; natural killer (NK) cell activity; growth and development of B and T lymphocytes and secretion by lymphocytes of lymphokines (molecules with killing or immunoregulatory activities).

Complement-dependent cytotoxicity (CDC) (or complement-mediated cytotoxicity, or complement-mediated cell lysis) is another process by which foreign or infectious agents can be destroyed. An antibody interaction with a foreign antigen, forming an antibody-antigen complex, can result in a conformational change in the Fc region of the antibody. This conformational change may activate complement factor C1, thereby initiating a complement activation cascade involving complement initiation factors C1, C2, C3, and C4. The complement activation cascade terminates in the sequential interaction of C5, C6, C7, C8 and C9 forming the membrane-attack complex (MAC). MAC mediates cell lysis by disrupting the phospholipid membrane of a cell to form large pores in the cell membrane. See, e.g., Reff, M. E. et al. *Blood* 83:435-445 (1994). In this way, the MAC complex is capable of stimulating cell death of a foreign or infectious agent containing an antigen recognized by an antibody of the invention. In addition, C3 and C4 can act as peptide mediators of inflammation, a process that results in localized vasodilation and migration of neutrophils, macrophages and other phagocytic cells. These phagocytic cells can bear Fc receptors, thereby increasing localized antibody-dependent cellular cytotoxicity.

In some embodiments, the antibody of the invention contains moderate to high Fc-mediated activity, including, but not limited to, moderate to high ADCC and/or moderate to high CDC activity. An antibody of the invention has "moderate to high" ADCC activity if at an antibody concentration of 10 μg/ml and effector cell to target cell ratio of 30, at least about 20%, at least about 30%, at least about 40%, at least about 50%, at least about 60%, at least about 70%, at least about 80%, or at least about 90% of target cells are lysed. An antibody of the invention has "moderate to high" CDC activity if at an antibody concentration of 10 μg/ml and in the presence of undiluted human serum or rabbit serum, at least about 20%, at least about 30%, at least about 40%, at least about 50%, at least about 60%, at least about 70%, at least about 80%, or at least about 90% of target cells are lysed.

Any of the known assays in the art can be used to monitor the Fc-mediated mechanisms of the antibodies of the invention. The ability of the antibodies of the present invention to initiate one or more Fc-mediated mechanisms can be monitored in vitro or in vivo. For example, CDC activity and ADCC activity of the antibodies can be measured by the methods of Ohta et al., *Cancer Immunol. Immunother.* 36:260 (1993). Other assays include but are not limited to a $^{51}$Cr release assay of antibody-dependent cell-mediated cytotoxicity, and complement-mediate lysis can also be used. See *Current Protocols in Immunology*, Coligan, A. M. et al. (Eds.), Wiley & Sons, Inc. (1991), e.g., Unit 7.27; Wang, B. et al., *Proc. Natl. Acad. Sci. USA* 96:1627-1632 (1999); Manches, O. et al., *Blood* 101:949-954 (2003).

Furthermore, Fc-mediated host responses can be monitored in vitro by conventional immunoassays, where the antitumor activity of the response can be determined by CDC and/or ADCC assays. The assay methodologies are well known, and are described in Handbook of Experimental Immunology, Vol. 2, Blackwell Scientific Publications, Oxford (1986). In addition, CDC activity and ADCC activity of humanized chimeric antibody to a cultured cancer cell line can be measured in accordance with the procedures disclosed in Menekigaku Jikken Nyumon, (Manual of Immunological Experiments) Matsuhashi et al., Gakkai Shuppan Center, Japan, 1981).

Fc-mediated mechanisms can be monitored in vivo by the development of delayed-type hypersensitivity reactions, or other in vivo or in vitro means known to those skilled in the art, including but not limited to the skin test reaction protocol, lymphocyte stimulation assays, measuring the toxicity of a subject's lymphocytes to tumor cells by using a standard radioactive release assay, by a limiting dilution assay, or by measuring plasma levels of IL-2 using standard ELISA assays.

Therapeutic Uses

The present invention is also directed to a method of treating cancer in a patient, the method comprising administering to a patient in need of such treatment a therapeutically effective amount of the antibody of the invention. In some embodiments, this antibody-based therapy involves administering antibodies of the invention to an animal, more particularly a mammal, and more particularly a human patient, for treating cancer.

A "therapeutically effective amount" is an amount of a compound that, when administered to a subject or patient for treating a condition, disorder or disease, is sufficient to elicit a cellular response that is clinically significant, without excessive levels of side effects. See, "Formulations and Therapeutic Administration" section, infra, for further details.

"Subject" refers to any animal classified as a mammal, including humans, domestic and farm animals, and zoo, sports, and companion animals such as a household pet and other domesticated animal such as, but not limited to, cattle, sheep, ferrets, swine, horses, poultry, rabbits, goats, dogs, cats and the like. In some embodiments, companion animals are dogs and cats. In other embodiments, the subject is human.

"Patient" refers to a subject, e.g., a human, in need of treatment of a condition, disorder or disease, e.g., cancer.

The terms "treat" and "treatment" refer to both therapeutic treatment and prophylactic or preventative measures, wherein the object is to prevent, inhibit, or slow down (lessen) an undesired physiological condition, disorder or disease or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset, or slowing, of condition, disorder or disease progression; amelioration of the condition, disorder or disease state, remission (whether partial or total); or enhancement or improvement of condition, disorder or disease. Treatment also includes, but is not limited to, eliciting a cellular response that is clinically significant, without excessive levels of side effects. Treatment also includes, but is not limited to, prolonging survival as compared to expected survival if not receiving treatment.

Therapeutic compounds of the invention include, but are not limited to, antibodies of the invention and nucleic acids encoding antibodies of the invention. The antibodies of the invention can be used to treat disorders or conditions associated with cancer including, but not limited to, any one or more of the diseases, disorders, or conditions described herein. Antibodies of the invention can be provided in pharmaceutically acceptable compositions as known in the art or as described herein.

The terms "tumor" and "cancer" are used interchangeably, and, along with their grammatical variants, refer to tumors of any cell type, including carcinomas, sarcomas, lymphomas and leukemias of any human and non-human animal species including swine, cats, dogs and higher primates. The methods and compositions of the present invention are suitable for the treatment of solid tumors, which can be characterized by extensive vasculature (microvascularized tumors), including carcinomas, sarcomas and lymphomas of various cell types. Solid tumors targeted by the treatment of the present invention include, but are not limited to: cancers of head and neck, including squamous cell and epidermoid carcinomas; adenocarcinomas, including prostatic, scirrhous, and mammary adenocarcinomas; lymphosarcoma; fibrosarcoma; leiomyosarcoma; chondroma; cancer of the prostate, lung, breast, ovary, stomach, pancreas, larynx, esophagus, testes, liver, parotid, biliary tract, colon, rectum, cervix, uterus, endometrium, kidney, bladder, or thyroid; primary tumors and metastases; melanomas; glioblastoma; Kaposi's sarcoma; non-small cell lung cancer; advanced malignancies; and blood born tumors such as, e.g., leukemias.

Malignant and metastatic conditions that can be treated with the antibodies of the invention include, but are not limited to, malignancies, solid tumors, and cancers described herein and otherwise known in the art (for a review of such disorders, see Fishman et al., *Medicine,* 2d Ed., J. B. Lippincott Co., Philadelphia (1985)). Thus, antibodies of the invention can be useful in treating other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

Treatment of metastases can be shown by the ability of the antibody of the invention to prevent tumor metastases in an animal model. For example, the spontaneous metastases model and the pulmonary metastases tumor model are metastases models known in the art. In the spontaneous metastases tumor model, an animal is subcutaneously injected with tumor cells which form a primary tumor mass. Subsequently, some of the cells of the tumor spontaneously migrate to other parts of the animal, including the lung. See Zisman, A. et al., *Cancer Research* 63:4952-59 (2003); Lev, D. C. et al., *Clin. Exp. Metas.* 20:515-23 (2003). In the pulmonary metastases tumor model, a suspension of tumor cells is injected into the tail vein a mouse and the formation of metastases in the lungs of the recipient animal is evaluated. See Tian F. et al, *Cancer Research* 63:8284-92 (2003); Ogawa, K. et al., *Int. J. Cancer* 91:797-802 (2001). In these models, an antibody that is effective in the treatment of metastases will, upon its administration to the recipient animal, either prevent metastases from occurring or reduce the number of metastases that form as compared to the number of metastases formed in a recipient animal given a negative control.

The antibody of the invention can be used to treat and/or diagnose hyperproliferative diseases, disorders, and/or conditions, including neoplasms. The antibody can inhibit proliferation of the disorder through direct or indirect interactions. For example, by increasing an immune response, particularly increasing antigenic qualities of the hyperproliferative disorder or by proliferating, differentiating, or mobilizing T-cells, hyperproliferative diseases, disorders, and/or conditions can be treated, and/or diagnosed. This immune response can be increased by either enhancing an existing immune response, or by initiating a new immune response.

Examples of hyperproliferative diseases, disorders, and/or conditions that can be treated, and/or diagnosed by the antibodies of the invention, include, but are not limited to, neoplasms located in the colon, lung, abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic, and urogenital systems.

Similarly, other hyperproliferative diseases, disorders, and/or conditions can be treated and/or diagnosed by antibodies of the invention. Examples of such hyperproliferative diseases, disorders, and/or conditions include, but are not limited to, hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

The present invention provides for treatment of diseases, disorders, and/or conditions associated with neovascularization by administration of the antibodies of the invention. The naturally occurring balance between endogenous stimulators and inhibitors of angiogenesis is one in which inhibitory influences predominate. Rastinejad et al., *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders and/or conditions, and psoriasis. See, e.g., reviews by Moses et al., *Biotech.* 9:630-634 (1991); Folkman et al., *N. Engl. J Med.,* 333:1757-1763 (1995); Auerbach et al., *J. Microvasc. Res.* 29:401-411 (1985); Folkman, Advances in Cancer Research, eds. Klein and Weinhouse, Academic Press, New York (1985), pp. 175-203; Patz, *Am. J. Opthalmol.* 94:715-743 (1982); and Folkman et al., *Science* 221:719-725 (1983). In a number of pathological conditions, the process of angiogenesis contributes to the disease state. For example, significant data has been accumulated suggesting that the growth of solid tumors is dependent on angiogenesis. Folkman and Klagsbrun, *Science* 235:442-447 (1987).

Additional ways in which the antibodies of the present invention can be used therapeutically include, but are not limited to, directed cytotoxicity of the antibody, e.g., as mediated by complement (CDC) or by effector cells (ADCC), or indirect cytotoxicity of the antibody, e.g., as immunoconjugates.

The antibodies of this invention can be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies, or as conjugated to a cytotoxic agent such as a radioisotope or other cytotoxic agent as described above.

The antibodies of the invention can be administered alone or in combination with other types of treatments (e.g., radiation therapy, chemotherapy, hormonal therapy, immunotherapy, anti-tumor agents, and anti-retroviral agents). In some embodiments, antibodies of the invention can be administered alone or in combination with anti-retroviral agents.

Formulations, Therapeutic Administration, and Kits

The invention also provides methods of treatment by administration to a subject of an effective amount of a compound, e.g., an antibody of the invention, or a pharmaceutical composition of the invention. In some embodiments, the antibody is substantially purified (e.g., substantially free from substances that limit its effect or produce undesired side-effects). The antibody can be conjugated to a cytotoxic agent.

Formulations and methods of administration that can be employed when the compound comprises an immunoglobulin are described herein; additional appropriate formulations and routes of administration can be selected from among those described herein below.

Various delivery systems are known and can be used to administer the compound or pharmaceutical composition of the invention, e.g., encapsulation in liposomes, microparticles, microcapsules, recombinant cells capable of expressing the compound, receptor-mediated endocytosis (see e.g., Wu and Wu, *J. Biol. Chem.* 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions can be administered by any convenient route, for example, by infusion or bolus injection, by absorption through epithelial or mucocutaneous linings (e.g., oral mucosa, rectal and intestinal mucosa, etc.) and can be administered together with other biologically active agents. Administration can be systemic or local. In addition, it can be desirable to introduce the pharmaceutical compounds or compositions of the invention into the central nervous system by any suitable route, including intraventricular and intrathecal injection; intraventricular injection can be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In some embodiments, it can be desirable to administer the pharmaceutical compounds or compositions of the invention locally to the area in need of treatment; this can be achieved, for example, and not by way of limitation, by local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. When administering a protein, including an antibody, of the invention, care must be taken to use materials to which the protein does not adsorb.

In other embodiments, the compound or composition can be delivered in a vesicle, in particular a liposome (see, Langer, *Science* 249:1527-1533 (1990); Treat et al., in *Liposomes in the Therapy of Infectious Disease and Cancer,* Lopez-Berestein and Fidler, eds., Liss, New York (1989), pp. 353-365; Lopez-Berestein, *ibid.,* pp. 317-327; see generally *ibid.*)

In yet other embodiments, the compound or composition can be delivered in a controlled release system. In some embodiments, a pump can be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In other embodiments, polymeric materials can be used (see *Medical Applications of Controlled Release,* Langer and Wise, eds., CRC Pres., Boca Raton, Fla. (1974); *Controlled Drug Bioavailability, Drug Product Design and Performance,* Smolen and Ball, eds., Wiley, New York (1984); Ranger and Peppas, *J., Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet other embodiments, a controlled release system can be placed in proximity of the therapeutic target, i.e., the brain, thus requiring only a fraction of the systemic dose (see, e.g., Goodson, in *Medical Applications of Controlled Release,* supra, vol. 2, pp. 115-138 (1984)). Other controlled release systems are discussed in the review by Langer, *Science* 249:1527-1533 (1990).

The present invention also provides pharmaceutical compositions. Such compositions comprise a therapeutically effective amount of a compound of the invention, and a pharmaceutically acceptable carrier. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In some embodiments, water can be used as a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* by E. W. Martin. Such compositions will contain a therapeutically effective amount of the compound, preferably in purified form, together with a suitable amount of carrier so as to provide the form for proper administration to the patient. The formulation should suit the mode of administration.

In other embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The amount of the compound of the invention, which will be therapeutically effective in the treatment of the disease or disorder, e.g., cancer, can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses can be extrapolated from dose-response curves derived from in vitro or animal model test systems.

For antibodies, the dosage administered to a patient is typically 0.1 mg/kg to 100 mg/kg of the patient's body weight. However, for radiolabeled antibodies, the dosage administered can be lower, e.g., 0.01 mg/kg to 1 mg/kg of the patient's body weight, and for toxin-immunoconjugates, the dosage administered can be even lower, e.g., 0.001 mg/kg of the patient's body weight. In some embodiments, the dosage administered to a patient is between 0.001 mg/kg and 100 mg/kg of the patient's body weight. In other embodiments, the dosage administered to a patient is between 0.01 mg/kg and 50 mg/kg of the patient's body weight. In other embodiments, the dosage administered to a patient is between 0.1 mg/kg and 20 mg/kg of the patient's body weight. In yet other embodiments, the dosage administered to a patient is between 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention can be reduced by enhancing uptake and tissue penetration (e.g., into the brain) of the antibodies by modifications such as, for example, lipidation.

The invention also provides a kit comprising the pharmaceutical composition of the present invention. The kit can include one or more containers filled with one or more of the ingredients of the pharmaceutical compositions of the invention. Optionally associated with such container(s) can be a notice or printed instructions.

For example, such printed instructions can be in a form prescribed by a governmental agency regulating the manufacture, use or sale of pharmaceuticals or biological products, which notice reflects approval by the agency of the manufacture, use or sale for human administration to treat a condition such as cancer. In some embodiments, the kit further comprises printed matter, which, e.g., provides information on the use of the pharmaceutical composition to treat cancer or a pre-recorded media device which, e.g., provides information on the use of the pharmaceutical composition to treat cancer, or a planner.

"Printed matter" can be, for example, one of a book, booklet, brochure or leaflet. The printed matter can describe the use of the pharmaceutical composition of the present invention for the treatment of cancer. Possible formats included, but are not limited to, a bullet point list, a list of frequently asked questions (FAQ) or a chart. Additionally, the information to be imparted can be illustrated in non-textual terms using pictures, graphics or other symbols.

"Pre-recorded media device" can be, for example, a visual media device, such as a videotape cassette, a DVD (digital video disk), filmstrip, 35 mm movie or any other visual media device. Alternately, pre-recorded media device can be an interactive software application, such as a CD-ROM (compact disk-read only memory) or floppy disk. Alternately, pre-recorded media device can be, for example, an audio media device, such as a record, audiocassette or audio compact disk. The information contained on the pre-recorded media device can describe the use of the pharmaceutical composition of the present invention for the treatment of cancer.

A "planner" can be, for example, a weekly, a monthly, a multi-monthly, a yearly, or a multi-yearly planner. The planner can be used as a diary to monitor dosage amounts, to keep track of dosages administered, or to prepare for future events wherein taking a regularly administered pharmaceutical composition of the present invention may be difficult. Alternately, the planner can be a calendar which will provide a means to monitor when a dosage has been taken and when it has not been taken. This type of planner will be particularly useful for patients having unusual schedules for administering medication to themselves. Additionally, the planner can be useful for the elderly, children, or other patient group who may administer medication to themselves and may become forgetful. One skilled in the art will appreciate the variety of planning tools that would be appropriate for use with the present invention.

The kit can also include a container for storing the other components of the kit. The container can be, for example, a bag, box, envelope or any other container that would be suitable for use in the present invention. Preferably, the container is large enough to accommodate each component and/ or any administrative devices that may be necessary of the pharmaceutical composition of the present invention. However, in some cases, it may be desirable to have a smaller container which can be hidden in a patient's pocketbook, briefcase or pocket.

Methods of Delivering the Pharmaceutical Composition of the Present Invention to a Patient The present invention is also directed to a method of delivering a pharmaceutical composition comprising a therapeutically effective amount of the antibody of the present invention to a patient in need thereof, the method comprising (a) registering in a computer readable medium the identity of a physician permitted to prescribe the pharmaceutical composition; (b) providing the patient with counseling information concerning the risks attendant to the pharmaceutical composition; (c) obtaining informed consent from the patient to receive the pharmaceutical composition despite the attendant risks; (d) registering the patient in a computer readable medium after obtaining their informed consent; and (e) permitting the patient access to the pharmaceutical composition.

The drug delivery methods of the present invention involve, inter alia, registering in a computer readable storage medium physicians who are qualified to prescribe the pharmaceutical composition of the present invention. Once registered in the computer readable storage medium, the physician can be eligible to prescribe the pharmaceutical composition to a patient in need thereof. Generally speaking, in order to become registered in the computer readable storage medium, the physician may be required to comply with various aspects of, for example, providing patient education and counseling. The registration of the physician in the computer readable storage medium can be achieved by providing the physician, for example, by mail, facsimile transmission, or on-line transmission, with a registration card or form, preferably together with educational materials concerning the pharmaceutical composition of the present invention. The physician can complete the registration card or form by providing information requested therein, and the registration card or form can be returned to the manufacturer or distributor of the pharmaceutical composition of the present invention, or other authorized recipient of the registration materials, for example, by mail, facsimile transmission or on-line transmission. The physician's information in the registration card or form is then entered into the computer readable storage medium. Suitable computer readable storage media which can be employed for registration of the physicians (as well as patients, as discussed below) will be apparent to one of ordinary skill in the art, once in possession of the teaching of the present application.

In the course of examination of a patient, including a patient suffering from cancer, the physician may determine that the patient's condition can be improved by the administration of the pharmaceutical composition of the present invention. Prior to prescribing the pharmaceutical composition of the present invention, the physician can counsel the patient, for example, on the various risks and benefits associated with the pharmaceutical composition. The patient can be provided full disclosure of all the known and suspected risks associated with the pharmaceutical composition. Such counseling can be provided verbally, as well as in written form. In some embodiments, the physician can provide the patient with literature materials on the pharmaceutical composition, such as product information, educational materials, and the like.

In addition to receiving counseling on the risks attendant to the pharmaceutical composition of the present invention, the methods of the invention further require the patient to fill out an informed consent form which is signed by the patient. Upon the completion of the informed consent form, the patient can be registered in a computer readable storage medium. The computer readable storage medium in which the patient is registered can be the same as, or different from, the computer readable storage medium in which the physician is registered.

The registration into one or more computer readable storage media of the physician and patient, according to the methods describe herein, provides a means to monitor and authorize access to the pharmaceutical composition of the present invention. Thus, the computer readable storage medium can serve to deny access to patients who fail to abide by the methods of the present invention. In some embodiments, access to the pharmaceutical composition of the invention is in the form of a prescription, wherein the prescribing physician is registered in a computer readable storage medium, has provided counseling to the patient concerning the attendant risks of the pharmaceutical composition, and has obtained informed consent from the patient, prior to prescribing the pharmaceutical composition to the patient in need thereof.

Methods of Educating a Consumer Regarding the Pharmaceutical Composition of the Present Invention The present invention is also directed to methods of educating consumers about the use of a pharmaceutical composition of the invention, the method comprising distributing the pharmaceutical composition with consumer information at a point of sale. In some embodiments, the distribution will occur at a point of sale having a pharmacist or healthcare provider.

As used herein, the term "consumer information" can include, but is not limited to, an English language text, non-English language text, visual image, chart, telephone recording, website, and access to a live costumer service representative. In some embodiments of the present invention, consumer information will provide directions for use of the pharmaceutical composition of the present invention, appropriate age use, indications, contraindications, or warnings. In some embodiments, the method further comprises providing professional information to relevant persons in a position to answer consumer questions regarding the pharmaceutical composition.

As used herein, the term "professional information" includes, but is not limited to, information concerning the pharmaceutical composition of the present invention designed to enable a healthcare professional to answer costumer questions regarding the pharmaceutical composition.

A "relevant person," as used herein, includes, for example, a physician, physician assistant, nurse practitioner, pharmacist and customer service representative.

The present invention is further directed to a method of identifying a pharmaceutical composition comprising a therapeutically effective amount of the antibody of the invention, the method comprising (a) isolating an antibody capable of binding to human tissue factor, wherein the antibody does not inhibit tissue factor mediated blood coagulation compared to normal plasma controls and can initiate an Fc-mediated mechanism; (b) repeating (a) to obtain a plurality of candidate antibodies that may prove therapeutically effective; (c) demonstrating that one such candidate antibody is non-toxic when administered to a non-human animal; (d) conducting a supervised clinical trial to demonstrate the non-toxic and effective character of one such candidate antibody; (e) securing approval of a regulatory agency to distribute one such candidate antibody to treat cancer; and (f) making a pharmaceutical composition comprising the candidate antibody as the active agent.

The phrase "isolation of antibody," as used herein, includes the use of assays and protocols, as previously described herein, concerning the production and isolation of an antibody capable of binding to human TF (hTF), wherein the antibody does not inhibit TF mediated blood coagulation compared to a normal plasma control as determined by in vitro coagulation assays. Upon the isolation of a plurality of candidate antibodies, the method further comprises demonstrating for a candidate antibody its non-toxic nature when administered to a non-human animal.

Methods for demonstrating the non-toxic nature of a pharmaceutical are well known in the art and include, but are not limited to, administering to a non-human animal the pharmaceutical composition of the present invention and conducting standard medical tests to establish the non-toxic effects of the pharmaceutical composition on the non-human animal receiving the pharmaceutical composition. In some embodiments of the present invention, the methods further comprise in vivo experimentation on non-human animals establishing the ability of the candidate antibody to bind human tissue factor, wherein the candidate antibody does not inhibit tissue factor mediated blood coagulation compared to normal plasma controls and can initiate an Fc-mediated mechanism in the non-human animal model.

A "clinical trial," as used herein refers to testing of a candidate antibody to evaluate its safety, determine the proper dosage range, and identify potential side effects of its use in humans. Additionally, clinical trials include studies conducted to confirm the pharmaceutical composition's effectiveness in treating cancer, as well as to provide information used to optimize the safe administration of the pharmaceutical composition to a human. Upon the successful completion of the clinical trial, the method further comprises securing the approval of a regulatory agency, e.g., the Food & Drug Administration, to make and distribute the candidate antibody for the treatment of cancer.

All of the various embodiments or options described herein can be combined in any and all variations.

The following examples are further illustrative of the present invention, but are not to be construed to limit the scope of the present invention.

EXAMPLES

Materials

Cell culture reagents were purchased from Invitrogen Corp., CA. Titan one Tube RT-PCR system was from Roche (Basel, Switzerland, Cat. # 1 855 476). Ni—NTA agarose was obtained from Qiagen (CA, Cat. # 30210) and Bio-GelP60 was from Bio-Rad (CA, Cat. # 150-4161). HiTrap protein G HP columns were purchased from Amersham (Buckinghamshire, United Kingdom, Cat. # 17-0404-01). Mouse anti-human TF mAb was obtained from Calbiochem (CA, Cat. # 612161). Pooled normal human plasma was from George King Bio-Medical Inc. (KA, Cat. # 0010-1). Cell dissociation solution was from Sigma (MO, Cat. # C-5914).

Construction of hTF Expression Vectors

The human tissue factor (hTF) gene was cloned from the human breast cancer cell line SKBR3 by RT-PCR. Briefly, 1 µg of total RNA was isolated from SKBR3 cells using the Trizol reagent (Invitrogen Corp., CA, Cat. # 15596018) according to the manufacturer's instructions. The isolated RNA was reverse-transcribed and amplified with primer TF4 (5' UTR-ACGGAACCCGCTCGATCTCG (SEQ ID NO:13)) and TF5 (3' UTR-TGCAGTAGCTCCAACAGTGC (SEQ ID NO:14)) using the Titan one Tube RT-PCR system following the manufacturer's instructions. The first PCR product was further amplified using primers TF1 (5'-ATC TGC GGA TCC ACC ATG GAG ACC CCT GCC TGG CC-3' (SEQ ID NO:15)) and TF3 (5'-ATC TGC CTC GAG TTA ATG GTG ATG GTG ATG GTG GGA TCC TCT TTC TCT GAA TTC CCC TTT CTC CTG-3' (SEQ ID NO:16)) to generate a hTF DNA fragment encoding the extracellular domain of hTF with a 32 amino acid N-terminal leader sequence and a 9 amino acid C-terminus RGS-His$_6$ tag sequence (soluble hTF). The soluble hTF contained 5' BamHI and 3' XhoI sites for insertion into expression vectors including a His- tag at the 3' end for protein purification. The first PCR product was also used to generate a full-length hTF gene with primers TF1 and TF2 (5'-ATC TGC CTC GAG TTA ATG GTG ATG GTG ATG GTG GGA TCC TCT TGA AAC ATT CAG TGG GGA GTT CTC-3' (SEQ ID NO:17)). The amplified soluble hTF and full-length hTF were cloned into the pCR4-TOPO vector (Invitrogen Corp., CA) for sequence analysis. The soluble hTF (SEQ ID NO:3) and full-length hTF (SEQ ID NO:1) encoding DNA fragments were also cloned into pCEP4 and pcDNA3.1 expression vectors (Invitrogen Corp., CA).

Expression and Purification of Soluble hTF $3 \times 10^5$ cells/well of HEK293 cells were plated in a 6-well plate one day before transfection. Cells were transfected with 1 µg of soluble hTF/pCEP4 plasmid DNA using Lipofectamine plus reagent (Invitrogen Corp., CA) for 3 hours at 37° C. according to the manufacturer's instructions. Stably transfected cells were selected by culturing cells in DMEM medium containing G418 (750 µg/ml). Soluble hTF protein was then purified from 300 ml of culture medium using a 1 ml size Ni-agarose column and eluted with linear imidazole buffer gradient (between 5 mM and 100 mM imidazole in PBS buffer). The soluble hTF containing fractions were identified by SDS-polyacrylamide gel electrophoresis (SDS-PAGE) analysis. The soluble hTF was further purified by gel filtration chromatography to remove contaminants. Briefly, samples were concentrated to about 100 µl with a Centrifugal Filter (Millipore, Mass., Cat. # UFV4BGC25) and loaded onto a 0.7×50 cm Bio-Gel P60 column in PBS. The protein was then eluted in PBS and 0.5 ml fractions were collected and analyzed by SDS-PAGE. The soluble hTF band was verified by standard Western blotting using a mouse anti-hTF mAb (Calbiochem, Calif., Cat. # 612161). The fractions containing soluble hTF were combined.

Preparation of Stable Full-length hTF Expression Cell Line

CHO-K1 cells were transfected with the full-length hTF/pcDNA3.1 plasmid (pTF103) using Lipofectamine plus reagent following the manufacturer's instructions (Invitrogen Corp., Calif.). Clones stably expressing full-length hTF were selected in the presence of 750 µg/ml of G418 containing DMEM medium. After one week of selection, resistant cells were removed from plates with Trypsin-EDTA solution and diluted with DMEM/G418 medium to a concentration of 3 cells/ml. 100 µl aliquots of the dilution were added into each well of one 96-well plate. Single cell clones were expanded and screened by FACS using a commercial anti-TF antibody (Calbiochem, Calif., Cat. # 612161).

Immunization and Measurement of Polyclonal, Anti-hTF IgG Response in Mice

A protocol for the rapid immunization of mice at multiple sites (RIMMS) has been previously described by Kilpatrick, K. E., et al., *Hybridoma* 16:381-389 (1997), and was used to generate antibodies against hTF in mice. Briefly, each of three 8-week-old, female Balb/c mice received 4 rounds of subcutaneous injections of the purified soluble hTF (10 μg/ml) over a course of 11 days at intervals of 3-5 days. For each round of immunization, the mice were anesthetized and then injected subcutaneously with the immunogen in complete Freund's adjuvant (CFA) at 2 sites in the nape of the neck and bilaterally at the calf and groin injecting 40-50 μl per site and in RIBI's adjuvant (Sigma, St. Louis, Mo.) at juxtaposed sites (lower and mid calf, thigh, and axilla), at a dose of 40-50 μl per site. Blood samples were taken prior to the priming injections and two days after the last boost and assayed in an ELISA for an antibody response to the immunogen. In the ELISA, a 96-well ELISA plate was coated with the immunogen (2 μg/ml) at 100 μl/well in PBS, pH 7.4 at 37° C. for 2 hrs. The plate was washed once with PBS containing 0.05% Tween-20 (PBS-T) and blocked with 1% BSA in PBS at 150 μl/well at 37° C. for 30 min. Following one wash with PBS-T, preimmune and immune sera diluted in PBS-T were added to the plate at 100 μl/well. The plate was incubated at 37° C. for 45 min and washed three times with PBS-T. Then, 100 μl of a 1:5000 dilution of goat anti-mouse IgG conjugated with horseradish peroxidase (Southern Biotech, Birmingham, Ala., Cat. # 1031-05) was added to each well. Following incubation at 37° C. for 30 min., the plate was washed with PBS-T three times. The antibody binding was visualized by adding 100 μl/well of TMB-$H_2O_2$ substrate buffer (Pierce, Rockford, Ill.). The reaction proceeded at room temperature for 10 min and was read using an ELISA plate reader at a wavelength of 650 nm. An antibody titer was defined as the reciprocal of serum dilution at which the O.D. reading was 2-fold higher than that of an internal negative control (wells with the secondary antibody only).

Antibodies TF278, TF277, TF392, and TF9 were generated using the same methods as described supra, except that each of the three Balb/c mice received 5 rounds of subcutaneous injections of the purified soluble hTF (10 μg/ml) over a course of 11 days at intervals of 2-4 days.

Generation of Hybridomas

Two days after the final boost, the immunized mice whose sera had ELISA titers greater than 1:10,000 were euthanized by asphyxiation with carbon dioxide. Bilateral popliteal, superficial inguinal, axillary and branchial lymph nodes were isolated and washed with fresh medium containing penicillin and streptomycin. Then, a single cell suspension was prepared from the lymph nodes in serum-free medium composed of 50% Excell-610 and 50% RPMI-1640 media. The lymph node cell suspension was washed twice with the aforementioned medium and collected by centrifugation at 400×g for 10 minutes at room temperature. In a 50-ml conical polypropylene tube, the lymph node cells were then fused with mouse myeloma cells (P3X63/Ag8.653, ATCC, Manassas, Va.) at a ratio of 2.5:1 by adding 1 ml of 50% polyethylene glycol 1500 (PEG, Roche Bioscience, Palo Alto, Calif.). The resulting PEG-cell preparation was washed once and then resuspended in hybridoma medium (HM) containing a mixture of 50:50 Excell-610 and RPMI-1640, 10% FBS, 10% Origen Cloning Factor (Igen, Rockville, Md.), 2 mM L-glutamine, 100 U/ml penicillin and streptomycin and 0.01 mM beta-mercaptoethanol, and distributed into flat-bottom, 96-well plates at $2×10^5$ cells/100 μl/well. After incubating for 18 hours at 37° C. with 7% $CO_2$, 100 μl of HM supplemented with 2×HAT (GIBCO-BRL, Grand Island, N.Y.) was added to each well. Media were changed 96 hr later to HM supplemented with 100 μM hypoxanthine and 16 μM thymidine. After 7 to 10 days of HAT selection, the plates were examined microscopically for hybridoma growth. Hybridomas from single colonies were further expanded individually in 24-well plates and the culture supernatants were screened by ELISA for mouse IgG antibodies specific for hTF (see below).

Primary Screening for Anti-hTF mAbs by ELISA

Briefly, a 96-well ELISA plate was coated with 100 μl/well of 2 μg/ml soluble hTF in PBS, pH 7.4 at 37° C. for 2 hrs. The plate was washed once with PBS-T and blocked with 150 μl/well of PBS containing 1% BSA at 37° C. for 30 min. Following washing once with PBS-T, hybridoma supernatants were added to the plate at 100 μl/well. The plate was incubated at 37° C. for 45 min and washed three times with PBS-T. Then, 100 μl of a 1:5000 dilution of goat anti-mouse IgG conjugated with horseradish peroxidase (Southern Biotechnology, Cat. # 1031-05) was added to each well. Following incubation at 37° C. for 30 min., the plate was washed with PBS-T three times. Antibody binding was visualized by adding 100 μl of TMB-$H_2O_2$ substrate buffer to each well. The reaction proceeded at room temperature for 10 min and was read using an ELISA plate reader at a wavelength of 650 nm. A positive reaction was defined as an O.D. reading, which was 2-fold higher than that of an internal negative control (secondary Ab alone). All ELISA positive clones were further expanded in HM and cryopreserved.

Secondary Screening for Anti-hTF mAbs by Flow Cytometry

Cells (CHO-K1) expressing full-length hTF were dissociated with 0.25% trypsin-EDTA solution, washed twice in cold PBS containing 2% FBS and 0.05% $NaN_3$ (FACS buffer) at 400×g for 10 min. and then distributed into U-bottom, 96-well microtiter plates at $0.5×10^6$ cell/well. The cells were centrifuiged at 200×g at 4° C. for 3 min. Following removal of supernatants by aspiration, the cells were resuspended in 70 μl of hybridoma supernatant. After incubation at 4° C. for 45 min., the cells were washed twice with cold FACS buffer, 220 μl/well, by centrifugation at 200×g for 3 min and resuspended in 50 μl of 1:25 FITC-labeled goat anti-mouse IgG (Southern Biotechnology). The cells were incubated at 4° C. for 30 min and then washed three times with cold FACS buffer, 220 μl/well. Finally, cells were resuspended in 0.4 ml of FACS buffer, and their fluorescence intensities were measured on a flow cytometer (FACScan, Becton Dickinson) and analyzed using Cell Quest software (Becton Dickinson). A positive clone was identified as a clone where the percent positive cells in the FACS profile was at least 3-fold higher than the profile obtained when the cells were stained only with the FITC-labeled goat anti-mouse IgG.

BIAcore Analysis of Anti-hTF mAbs

Binding properties of anti-hTF mAbs were evaluated using BIAcore X. Briefly, a CM5 BIAcore biosensor chip was docked into the instrument and activated with 55 μl of 1:1 NHS/EDC at room temperature. The recombinant soluble hTF and BSA (10 μg/ml in 0.05 M acetate buffer, pH 4.5) were immobilized on the activated chips in flow cells 1 and 2, respectively. The immobilization was carried out at a flow rate of 5 μl/min until a resonance response of 1000-2000 RU was achieved. The chip was then blocked by injection of 55 μl of ethanolamine-HCl, pH 8.5 followed by 5 washes with 50 mM NaOH, 1 M NaCl. To measure the binding of anti-hTF mAbs to the soluble hTF immobilized to the chip, 30 μl of anti-hTF mAbs at varying concentrations in BIAcore running buffer (HBS-EP, Biacore AB, Uppsala, Sweden, Cat. #1001-08) were injected over the sensor surface at a flow rate of 5 μl/min. Following completion of the injection phase, dissociation was monitored in BIAcore running buffer at the same flow rate for 360 seconds. The surface was regenerated between injections using 30 μl of 50 mM NaOH-1 M NaCl. Individual sensorgrams were analyzed using BIAsimulation software. Representative data are shown in Tables 3 and 4.

Preparation of TF Membrane Extract

CHO-K1 cells (5×10$^7$) expressing full-length hTF were harvested with cell dissociation solution and washed once with ice-cold 1×PBS. Cells were resuspended in 2 ml of membrane extraction buffer (10 mM Tris-HCl, pH=8.0, 1 mM MgCl2, 1 mM PMSF, 2 μg/ml aprotinin, 2 μg/ml leupeptin) and homogenized on ice with a Tissue Tearor tissue homogenizer (Biospec Products, Inc., Bartlesville, Okla.) three times for 30 seconds each. Cell debris was removed by centrifugation at 1500×g for 5 min. Cell membranes were collected by centrifugation at 12,000×g for 30 minutes at 4° C. The pellets were resuspended in 1×PBS, aliquoted and stored at −20° C.

Purification of Hybridoma IgG

ELISA and FACS positive hybridoma clones were cultured in low IgG hybridoma medium (40% RPMI1640, 40% EX-Cell Hybridoma medium, 10% low IgG FBS, 10% ORIGEN cloning factor, 2 mM L-glutamine, 10 mM HEPES, 1 mM Sodium Pyruvate) at 37° C., in a humidified atmosphere with 7% $CO_2$. 40 ml of culture medium containing the secreted antibody were loaded onto a 1 ml HiTrap protein G HP column and then washed with 10 ml of PBS. The bound IgG was eluted from the column with 3 ml of 0.1 M glycine, pH 3.7 and neutralized with 1 M Tris-HCl, pH 9.0. The fractions containing IgG were pooled and dialyzed in PBS.

htF Coagulation Assay

Anti-coagulation activity of the hTF antibodies was determined using an assay according to Morrissey, J. H., et al., *Thrombosis Research* 52:247-261 (1988) (also known as two stage prothrombin (2st-PT) assay), and Fang, C. H., et al., *Thrombosis and Haemostasis* 76: 361-368 (1996). Different dilutions of the hTF membrane extract were adjusted with PBS to 100 μl and pre-warmed in a 37° C. water bath for 30 minutes. 50 μl of human plasma and 50 μl of 50 mM $CaCl_2$ solution were then added to the mixture to initiate blood coagulation in a clear disposable plastic cuvette. Blood coagulation was monitored by measuring in 15 second intervals the absorbance at 405 nm ($A_{405}$). Blood coagulation was complete when the change in the $A_{405}$ reading reached less than 0.01 in 15 seconds. The hTF membrane dilution that resulted in a blood coagulation time of 180 seconds was used to test the inhibitory effect of the hTF mAbs. To test the inhibitory effect of hTF mAb on blood coagulation, hTF membrane extract was incubated with each mAb (final concentrations of 10 μg/ml to 100 μg/ml) at 37° C. for 30 min before the initiation of the blood coagulation reaction.

TABLE 1

Summary for Screening of Anti-hTF Hybridomas by ELISA and FACS

| | Number of Clones | Percentage |
|---|---|---|
| # of clones screened | 253 | N/A |
| # of ELISA-positive clones | 102 | 40.3 |
| # of FACS-positive clones | 31 | 12.3 |

TABLE 2

Summary for Individual FACS-positive Clones

| Clone ID | % Positive |
|---|---|
| 11 | 99.1 |
| 20 | 99.5 |
| 28 | 99.4 |
| 29 | 99.7 |
| 41 | 99.5 |
| 54 | 98.0 |
| 75 | 99.3 |
| 84 | 99.4 |
| 85 | 97.3 |
| 92 | 73.3 |
| 120 | 36.5 |
| 128 | 99.8 |
| 129 | 98.1 |
| 144 | 99.3 |
| 169 | 97.9 |
| 170 | 99.5 |
| 172 | 99.5 |
| 196 | 99.8 |
| 199 | 99.8 |
| 236 | 99.2 |
| 248 | 67.0 |
| 260 | 99.6 |
| 109 | 32.6 |
| 130 | 28.1 |
| 112 | 26.6 |
| 50 | 25.5 |
| 68 | 16.1 |
| 12 | 13.7 |
| 251 | 13.3 |
| 93 | 11.9 |
| 190 | 11.6 |

Note: The results were obtained by FACS screening of culture supernatants of individual hybridoma grown in 24-well plates. Percent positive indicates the population of TF34 cells that stably expressed TF and stained positive.

TABLE 3

Summary of Selected Monoclonal Anti-TF Antibodies

| Clone# | FACS | TF coagulation (s) | Ka (l/Ms) | Kd (l/s) | KD = kd/ka (M) |
|---|---|---|---|---|---|
| # 260 | + | 190 ± 9 | 9.91E+03 | 1.91E−04 | 1.93E−08 |
| # 196 | + | 195 ± 0 | 4.21E+04 | 2.79E−03 | 6.63E−08 |
| # 236 | + | 217 ± 11 | 2.62E+04 | 1.86E−02 | 7.10E−07 |
| # 54 | + | 225 ± 0 | 1.11E+05 | 3.84E−02 | 3.46E−07 |
| # 84 | + | 400 ± 28 | 8.18E+04 | 1.02E−03 | 1.25E−08 |
| Normal Control | | 191 ± 16 | | | |
| B-Fact (Borderline) | | 240 | | | |

Note: Normal plasma control and B-Fact control (pooled normal human plasma diluted to 30-50% of normal coagulation activity (George King Bio-medical, Inc., KS, Cat. #0040-0)) showed the blood coagulation time for normal human blood and borderline human blood samples in our assay format. All antibodies that had shorter coagulation times than the borderline control are listed. Only one representative inhibitory antibody (#84) with longer coagulation time is shown. Most of the antibodies inhibit coagulation.

TABLE 4

Summary of Selected Monoclonal Anti-TF Antibodies

| Clones | Isotype | Ab Con. (ug/ml) | Coagulation (seconds) | Kd (l/s) | KD (M) | FACS (H596) Bmax | EC50 (nM) |
|---|---|---|---|---|---|---|---|
| TF278 | IgG1λ | 10 | 190 ± 17.3 (3) | 1.38E−04 | 7.89E−10 | 16, 26 | 0.48, 1.14 |
| TF9 | IgG1k | 10 | 195 ± 15 (3) | 3.64E−04 | 1.84E−09 | | |
| TF392 | IgG1λ | 10 | 210 | 1.30E−04 | 2.46E−09 | 58 | 6.29 |
| TF277 | IgG1k | 10 | 202.5 ± 10.6 (2) | 3.12E−03 | 7.14E−09 | 19, 29 | 0.48, 0.71 |

Note: In Table 4, the same normal plasma control and B-Fact control (pooled normal human plasma diluted to 30-50% of normal coagulation activity (George King Bio-medical, Inc., KS, Cat. #0040-0)) as displayed in Table 3 were used. All antibodies listed in Table 4 had a shorter coagulation time than the borderline control (B-Fact control).

ADCC Activity

Figure 4A:
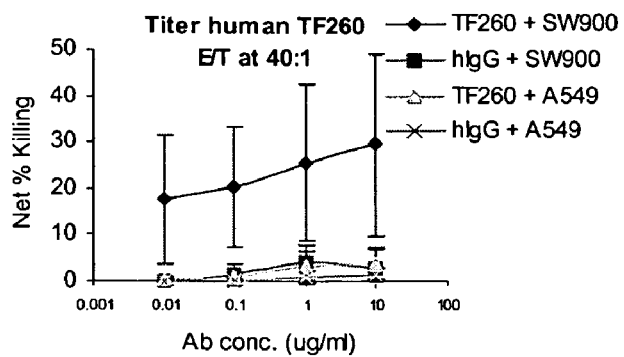
FIGS. 4A-4C. ADCC assays using human chimeric anti-TF antibodies TF260, TF278 and TF392. TF-positive SW900 and TF-negative A549 lung tumor cells were used as targets. An irrelevant human IgG1 was used as the negative control antibody.
Figure 4B:
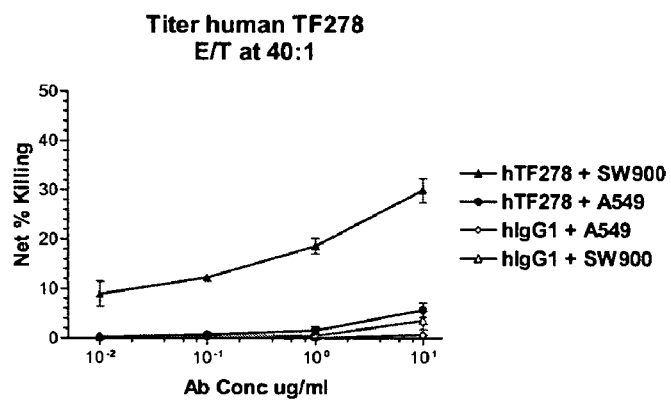
Figure 4C:
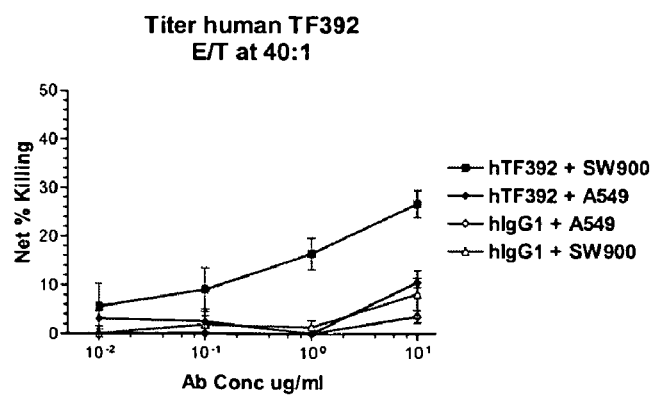

The ADCC activity of anti-TF antibodies TF260, TF278, and TF392 was determined using the following ADCC assay. Human leukocytes were isolated from peripheral blood of normal donors using a Histopaque-1077 gradient centrifugation procedure (Sigma Co., St. Louis, Mo.). The isolated leukocytes were then used as effector cells. In U-bottom, 96-well plates, tumor cells ($5 \times 10^3$/well) were mixed with the Histopaque-purified human leukocytes at effector-to-target (E/T) ratios of 0:1-40:1 in the absence or presence of varying concentrations of anti-human TF mAbs or a control antibody in a total volume of 120 µl of RPMI 1640 supplemented with 10% FBS. The plates were incubated at 37° C. in a humidified atmosphere containing 5% $CO_2$. Target cells mixed with effector cells without the testing antibody were used as negative controls. Following a 16-18 hr. incubation, 50 µl aliquots of culture supernatant were collected and assayed for lactate dehydrogenase activity in flat-bottom, 96-well plates using the Cytotox 96 Non-radioactive Cytotoxicity Assay Kit (Promega Co., Madison, Wis.) according to the manufacturer's instruction. The percentage lysis of tumor cells was calculated as follows: % Cytotoxicity=experimental release–effector spontaneous release–target spontaneous release)/(target maximum release–target spontaneous release)×100. The ADCC results for anti-TF antibodies TF260, TF278, and TF392 were expressed as mean percentage lysis±S.D. of triplicate samples from 6-7 donors and can be found in FIGS. 4A-4C. For the ADCC assays, TF-positive SW900 and TF-negative A549 lung tumor cells were used as targets. An irrelevant human IgG1 was used as the negative antibody control. FIGS. 4A-4C demonstrate that anti-TF antibodies TF260, TF278, and TF392 cause an increase in % cytotoxicity when incubated with TF-positive cells as compared to the negative antibody control (hIgG).

All documents, e.g., scientific publications, patents and patent publications, recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A method of treating cancer in a patient, said method comprising administering to said patient a pharmaceutical composition comprising an isolated antibody capable of binding to human tissue factor, wherein said antibody is obtained from a hybridoma cell line TF260 deposited under ATCC Accession No. PTA-5197 or a hybildoma cell line TF196 deposited under ATCC Accession No. PTA-5196 and does not inhibit tissue factor mediated blood coagulation compared to a normal plasma control, and wherein said cancer is selected from the group consisting of non-small cell lung cancer, breast cancer, colon cancer, and prostate cancer.

2. The method of claim 1, wherein said cancer is a solid tumor.

3. The method of claim 1, wherein said pharmaceutical composition comprises an antibody conjugated to a cytotoxic agent.

4. The method of claim 3, wherein said cytotoxic agent is selected from the group consisting of: a paclitaxol, cytochalasin B, gramicidin D, ethidium bromide, emetine, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, and a radioisotope.

5. The method of claim 1, wherein said antibody is conjugated to a detectable agent.

6. The method of claim 5, wherein said detectable agent is selected from the group consisting of: an enzyme, prosthetic group, fluorescent material, luminescent material, bioluminescent material, radioactive material, positron emitting metal using a positron emission tomography, and nonradioactive paramagnetic metal ion.

7. The method of claim 1, wherein said pharmaceutical composition comprises a therapeutically effective amount of said antibody and a pharmaceutically acceptable carrier.

8. The method of claim 1, wherein said antibody is obtained from a hybridoma cell line TF260 deposited under ATCC Accession No. PTA-5197.

9. The method of claim 1, wherein said antibody is obtained from a hybridoma cell line TF196 deposited under ATCC Accession No. PTA-5196.

10. A method of detecting cancer, said method comprising:
providing to a sample or subject a pharmaceutical composition comprising an isolated antibody conjugated to a detectable agent capable of binding to human tissue factor, wherein said antibody is obtained from a hybridoma cell line TF260 deposited under ATCC Accession No. PTA-5197 or a hybridoma cell line TF196 deposited under ATCC Accession No. PTA-5196 and does not inhibit tissue factor mediated blood coagulation compared to a normal plasma control; and
detecting the binding of said detectable agent to a cancer cell, wherein said cancer is selected from the group consisting of non-small cell lung cancer, breast cancer, colon cancer, and prostate cancer.

11. The method of claim 10, wherein said detectable agent is selected from the group consisting of: an enzyme, prosthetic group, fluorescent material, luminescent material, bioluminescent material, radioactive material, positron emitting metal using a positron emission tomography, and nonradioactive paramagnetic metal ion.

12. The method of claim 10, wherein said antibody is obtained from a hybridoma cell line TF260 deposited under ATCC Accession No. PTA-5197.

13. The method of claim 10, wherein said antibody is obtained from a hybridoma cell line TF196 deposited under ATCC Accession No. PTA-5196.

14. A method of treating cancer in a patient, said method comprising administering to said patient a pharmaceutical composition comprising an isolated antibody capable of binding to human tissue factor, wherein said antibody is obtained from a hybridoma cell line TF260 deposited under ATCC Accession No. PTA-5197 or a hybridoma cell line TF196 deposited under ATCC Accession No. PTA-5196 and does not inhibit tissue factor mediated blood coagulation compared to a normal plasma control, is conjugated to a cytotoxic agent or a detectable agent, and wherein said cancer is selected from the group consisting of non-small cell lung cancer, breast cancer, colon cancer, and prostate cancer.

15. The method of claim 14, wherein said cancer is a solid tumor.

16. The method of claim 14, wherein said detectable agent is selected from the group consisting of: an enzyme, prosthetic group, fluorescent material, luminescent material, bioluminescent material, radioactive material, positron emitting metal using a positron emission tomography, and nonradioactive paramagnetic metal ion.

17. The method of claim 14, wherein said cytotoxic agent is selected from the group consisting of: a paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, and a radioisotope.

18. The method of claim 14, wherein said pharmaceutical composition comprises a therapeutically effective amount of said antibody and a pharmaceutically acceptable carrier.

19. The method of claim 14, wherein said antibody is obtained from a hybridoma cell line TF260 deposited under ATCC Accession No. PTA-5197.

20. The method of claim 14, wherein said antibody is obtained from a hybridoma cell line TF196 deposited under ATCC Accession No. PTA-5196.

21. A method of treating cancer in a patient, said method comprising administering to said patient a pharmaceutical composition comprising an isolated antibody capable of binding to human tissue factor, wherein said antibody is obtained from a hybridoma cell line TF278 deposited under ATCC Accession No. PTA-5676, a hybridoma cell line TF392 deposited under ATCC Accession No. PTA-5677, or a hybridoma cell line TF9 deposited under ATCC Accession No. PTA-5674 and does not inhibit tissue factor mediated blood coagulation compared to a normal plasma control, and wherein said cancer is selected from the group consisting of non-small cell lung cancer, breast cancer, colon cancer, and prostate cancer.

22. The method of claim 21, wherein said antibody is obtained from a hybridoma cell line TF278 deposited under ATCC Accession No. PTA-5676.

23. The method of claim 21, wherein said antibody is obtained from a hybridoma cell line TF392 deposited under ATCC Accession No. PTA-5677.

24. The method of claim 21, wherein said antibody is obtained from a hybridoma cell line TF9 deposited under ATCC Accession No. PTA-5674.

25. The method of claim 21, wherein said cancer is a solid tumor.

26. The method of claim 21, wherein said pharmaceutical composition comprises an antibody conjugated to a cytotoxic agent.

27. The method of claim 26, wherein said cytotoxic agent is selected from the group consisting of: a paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mitbramycin, actinomycin D, 1-dehydrotestosterone, glucocorticoid, procaine, tetracaine, lidocaine, propranolol, puromycin, and a radioisotope.

28. The method of claim 21, wherein said antibody is conjugated to a detectable agent.

29. The method of claim 28, wherein said detectable agent is selected from the group consisting of: an enzyme, prosthetic group, fluorescent material, luminescent material, bioluminescent material, radioactive material, positron emitting metal using a positron emission tomography, and nonradioactive paramagnetic metal ion.

30. The method of claim 21, wherein said pharmaceutical composition comprises a therapeutically effective amount of said antibody and a pharmaceutically acceptable carrier.

31. A method of detecting cancer, said method comprising:
providing to a sample or subject a pharmaceutical composition comprising an isolated antibody conjugated to a detectable agent capable of binding to human tissue factor, wherein said antibody is obtained from a hybridoma cell line TF278 deposited under ATCC Accession No. PTA-5676, a hybridoma cell line TF392 deposited under ATCC Accession No. PTA-5677, or a hybridoma cell line TF9 deposited under ATCC Accession No. PTA-5674 and does not inhibit tissue factor mediated blood coagulation compared to a normal plasma control; and
detecting the binding of said detectable agent to a cancer cell, wherein said cancer is selected from the group consisting of non-small cell lung cancer, breast cancer, colon cancer, and prostate cancer.

32. The method of claim 31, wherein said antibody is obtained from a hybridoma cell line TF278 deposited under ATCC Accession No. PTA-5676.

33. The method of claim 31, wherein said antibody is obtained from a hybridoma cell line TF392 deposited under ATCC Accession No. PTA-5677.

34. The method of claim 31, wherein said antibody is obtained from a hybridoma cell line TF9 deposited under ATCC Accession No. PTA-5674.

35. The method of claim 31, wherein said detectable agent is selected from the group consisting of: an enzyme, prosthetic group, fluorescent material, luminescent material, bioluminescent material, radioactive material, positron emitting metal using a positron emission tomography, and nonradioactive paramagnetic metal ion.

36. A method of treating cancer in a patient, said method comprising administering to said patient a pharmaceutical composition comprising an isolated antibody capable of binding to human tissue factor, wherein said antibody is obtained from a hybridoma cell line TF278 deposited under ATCC Accession No. PTA-5676, hybridoma cell line TF392 deposited under ATCC Accession No. PTA-5677, or a hybridoma cell line TF9 deposited under ATCC Accession No. PTA-5674 and does not inhibit tissue factor mediated blood coagulation compared to a normal plasma control, wherein said antibody is conjugated to a cytotoxic agent or a detectable agent, and wherein said cancer is selected from the group consisting of non-small cell lung cancer, breast cancer, colon cancer, and prostate cancer.

37. The method of claim 36, wherein said antibody is obtained from a hybridoma cell line TF278 deposited under ATCC Accession No. PTA-5676.

38. The method of claim 36, wherein said antibody is obtained from a hybridoma cell line TF392 deposited under ATCC Accession No. PTA-5677.

39. The method of claim 36, wherein said antibody is obtained from a hybridoma cell line TF9 deposited under ATCC Accession No. PTA-5674.

40. The method of claim 36, wherein said cancer is a solid tumor.

41. The method of claim 36, wherein said detectable agent is selected from the group consisting of: an enzyme, prosthetic group, fluorescent material, luminescent material, bioluminescent material, radioactive material, positron emitting metal using a positron emission tomography, and nonradioactive paramagnetic metal ion.

42. The method of claim 36, wherein said cytotoxic agent is selected from the group consisting of: a paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mitbramycin, actinomycin D, 1-dehydrotestosterone, glucocorticoid, procaine, tetracaine, lidocaine, propranolol, puromycin, and a radioisotope.

43. The method of claim 36, wherein said pharmaceutical composition comprises a therapeutically effective amount of said antibody and a pharmaceutically acceptable carrier.

* * * * *

SEQUENCE LISTING

```
<160> NUMBER OF SEQ ID NOS: 35

<210> SEQ ID NO 1
<211> LENGTH: 915
<212> TYPE: DNA
<213> ORGANISM: Homo sapiens
<220> FEATURE:
<221> NAME/KEY: CDS
<222> LOCATION: (1)..(915)

<400> SEQUENCE: 1 atg gag acc cct gcc tgg ccc cgg gtc ccg cgc ccc gag acc gcc gtc        48
Met Glu Thr Pro Ala Trp Pro Arg Val Pro Arg Pro Glu Thr Ala Val
1               5                   10                  15 gct cgg acg ctc ctg ctc ggc tgg gtc ttc gcc cag gtg gcc ggc gct        96
Ala Arg Thr Leu Leu Leu Gly Trp Val Phe Ala Gln Val Ala Gly Ala
                20                  25                  30 tca ggc act aca aat act gtg gca gca tat aat tta act tgg aaa tca       144
Ser Gly Thr Thr Asn Thr Val Ala Ala Tyr Asn Leu Thr Trp Lys Ser
            35                  40                  45 act aat ttc aag aca att ttg gag tgg gaa ccc aaa ccc gtc aat caa       192
Thr Asn Phe Lys Thr Ile Leu Glu Trp Glu Pro Lys Pro Val Asn Gln
        50                  55                  60
```

```
gtc tac act gtt caa ata agc act aag tca gga gat tgg aaa agc aaa    240
Val Tyr Thr Val Gln Ile Ser Thr Lys Ser Gly Asp Trp Lys Ser Lys
 65                  70                  75                  80 tgc ttt tac aca aca gac aca gag tgt gac ctc acc gac gag att gtg    288
Cys Phe Tyr Thr Thr Asp Thr Glu Cys Asp Leu Thr Asp Glu Ile Val
                 85                  90                  95 aag gat gtg aag cag acg tac ttg gca cgg gtc ttc tcc tac ccg gca    336
Lys Asp Val Lys Gln Thr Tyr Leu Ala Arg Val Phe Ser Tyr Pro Ala
            100                 105                 110 ggg aat gtg gag agc acc ggt tct gct ggg gag cct ctg tat gag aac    384
Gly Asn Val Glu Ser Thr Gly Ser Ala Gly Glu Pro Leu Tyr Glu Asn
        115                 120                 125 tcc cca gag ttc aca cct tac ctg gag aca aac ctc gga cag cca aca    432
Ser Pro Glu Phe Thr Pro Tyr Leu Glu Thr Asn Leu Gly Gln Pro Thr
130                 135                 140 att cag agt ttt gaa cag gtg gga aca aaa gtg aat gtg acc gta gaa    480
Ile Gln Ser Phe Glu Gln Val Gly Thr Lys Val Asn Val Thr Val Glu
145                 150                 155                 160 gat gaa cgg act tta gtc aga agg aac aac act ttc cta agc ctc cgg    528
Asp Glu Arg Thr Leu Val Arg Arg Asn Asn Thr Phe Leu Ser Leu Arg
                165                 170                 175 gat gtt ttt ggc aag gac tta att tat aca ctt tat tat tgg aaa tct    576
Asp Val Phe Gly Lys Asp Leu Ile Tyr Thr Leu Tyr Tyr Trp Lys Ser
            180                 185                 190 tca agt tca gga aag aaa aca gcc aaa aca aac act aat gag ttt ttg    624
Ser Ser Ser Gly Lys Lys Thr Ala Lys Thr Asn Thr Asn Glu Phe Leu
        195                 200                 205 att gat gtg gat aaa gga gaa aac tac tgt ttc agt gtt caa gca gtg    672
Ile Asp Val Asp Lys Gly Glu Asn Tyr Cys Phe Ser Val Gln Ala Val
210                 215                 220 att ccc tcc cga aca gtt aac cgg aag agt aca gac agc ccg gta gag    720
Ile Pro Ser Arg Thr Val Asn Arg Lys Ser Thr Asp Ser Pro Val Glu
225                 230                 235                 240 tgt atg ggc cag gag aaa ggg gaa ttc aga gaa ata ttc tac atc att    768
Cys Met Gly Gln Glu Lys Gly Glu Phe Arg Glu Ile Phe Tyr Ile Ile
                245                 250                 255 gga gct gtg gta ttt gtg gtc atc atc ctt gtc atc atc ctg gct ata    816
Gly Ala Val Val Phe Val Val Ile Ile Leu Val Ile Ile Leu Ala Ile
            260                 265                 270 tct cta cac aag tgt aga aag gca gga gtg ggg cag agc tgg aag gag    864
Ser Leu His Lys Cys Arg Lys Ala Gly Val Gly Gln Ser Trp Lys Glu
        275                 280                 285 aac tcc cca ctg aat gtt tca aga gga tcc cac cat cac cat cac cat    912
Asn Ser Pro Leu Asn Val Ser Arg Gly Ser His His His His His His
290                 295                 300 taa                                                                 915
```

<210> SEQ ID NO 2
<211> LENGTH: 304
<212> TYPE: PRT
<213> ORGANISM: Homo sapiens

<400> SEQUENCE: 2

```
Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45
```

-continued

```
Thr Asn Phe Lys Thr Ile Leu Glu Trp Glu Pro Lys Pro Val Asn Gln
 50                  55                  60

Val Tyr Thr Val Gln Ile Ser Thr Lys Ser Gly Asp Trp Lys Ser Lys
 65                  70                  75                  80

Cys Phe Tyr Thr Thr Asp Thr Glu Cys Asp Leu Thr Asp Glu Ile Val
                 85                  90                  95

Lys Asp Val Lys Gln Thr Tyr Leu Ala Arg Val Phe Ser Tyr Pro Ala
                100                 105                 110

Gly Asn Val Glu Ser Thr Gly Ser Ala Gly Glu Pro Leu Tyr Glu Asn
                115                 120                 125

Ser Pro Glu Phe Thr Pro Tyr Leu Glu Thr Asn Leu Gly Gln Pro Thr
        130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
        275                 280                 285

Asn Ser Pro Leu Asn Val Ser Arg Gly Ser His His His His His His
        290                 295                 300
```

<210> SEQ ID NO 3
<211> LENGTH: 783
<212> TYPE: DNA
<213> ORGANISM: Homo sapiens
<220> FEATURE:
<221> NAME/KEY: CDS
<222> LOCATION: (1)..(783)

<400> SEQUENCE: 3

```
atg gag acc cct gcc tgg ccc cgg gtc ccg cgc ccc gag acc gcc gtc      48
Met Glu Thr Pro Ala Trp Pro Arg Val Pro Arg Pro Glu Thr Ala Val
  1               5                  10                  15 gct cgg acg ctc ctg ctc ggc tgg gtc ttc gcc cag gtg gcc ggc gct      96
Ala Arg Thr Leu Leu Leu Gly Trp Val Phe Ala Gln Val Ala Gly Ala
                 20                  25                  30 tca ggc act aca aat act gtg gca gca tat aat tta act tgg aaa tca     144
Ser Gly Thr Thr Asn Thr Val Ala Ala Tyr Asn Leu Thr Trp Lys Ser
             35                  40                  45 act aat ttc aag aca att ttg gag tgg gaa ccc aaa ccc gtc aat caa     192
Thr Asn Phe Lys Thr Ile Leu Glu Trp Glu Pro Lys Pro Val Asn Gln
 50                  55                  60 gtc tac act gtt caa ata agc act aag tca gga gat tgg aaa agc aaa     240
Val Tyr Thr Val Gln Ile Ser Thr Lys Ser Gly Asp Trp Lys Ser Lys
 65                  70                  75                  80
```

```
tgc ttt tac aca aca gac aca gag tgt gac ctc acc gac gag att gtg      288
Cys Phe Tyr Thr Thr Asp Thr Glu Cys Asp Leu Thr Asp Glu Ile Val
                85                  90                  95 aag gat gtg aag cag acg tac ttg gca cgg gtc ttc tcc tac ccg gca      336
Lys Asp Val Lys Gln Thr Tyr Leu Ala Arg Val Phe Ser Tyr Pro Ala
            100                 105                 110 ggg aat gtg gag agc acc ggt tct gct ggg gag cct ctg tat gag aac      384
Gly Asn Val Glu Ser Thr Gly Ser Ala Gly Glu Pro Leu Tyr Glu Asn
        115                 120                 125 tcc cca gag ttc aca cct tac ctg gag aca aac ctc gga cag cca aca      432
Ser Pro Glu Phe Thr Pro Tyr Leu Glu Thr Asn Leu Gly Gln Pro Thr
    130                 135                 140 att cag agt ttt gaa cag gtg gga aca aaa gtg aat gtg acc gta gaa      480
Ile Gln Ser Phe Glu Gln Val Gly Thr Lys Val Asn Val Thr Val Glu
145                 150                 155                 160 gat gaa cgg act tta gtc aga agg aac aac act ttc cta agc ctc cgg      528
Asp Glu Arg Thr Leu Val Arg Arg Asn Asn Thr Phe Leu Ser Leu Arg
                165                 170                 175 gat gtt ttt ggc aag gac tta att tat aca ctt tat tat tgg aaa tct      576
Asp Val Phe Gly Lys Asp Leu Ile Tyr Thr Leu Tyr Tyr Trp Lys Ser
            180                 185                 190 tca agt tca gga aag aaa aca gcc aaa aca aac act aat gag ttt ttg      624
Ser Ser Ser Gly Lys Lys Thr Ala Lys Thr Asn Thr Asn Glu Phe Leu
        195                 200                 205 att gat gtg gat aaa gga gaa aac tac tgt ttc agt gtt caa gca gtg      672
Ile Asp Val Asp Lys Gly Glu Asn Tyr Cys Phe Ser Val Gln Ala Val
    210                 215                 220 att ccc tcc cga aca gtt aac cgg aag agt aca gac agc ccg gta gag      720
Ile Pro Ser Arg Thr Val Asn Arg Lys Ser Thr Asp Ser Pro Val Glu
225                 230                 235                 240 tgt atg ggc cag gag aaa ggg gaa ttc aga gaa aga gga tcc cac cat      768
Cys Met Gly Gln Glu Lys Gly Glu Phe Arg Glu Arg Gly Ser His His
                245                 250                 255 cac cat cac cat taa                                                  783
His His His His
            260

<210> SEQ ID NO 4
<211> LENGTH: 260
<212> TYPE: PRT
<213> ORGANISM: Homo sapiens

<400> SEQUENCE: 4

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125
```

Ser Pro Glu Phe Thr Pro Tyr Leu Glu Thr Asn Leu Gly Gln Pro Thr
            130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Arg Gly Ser His His
                245                 250                 255

His His His His
        260

<210> SEQ ID NO 5
<211> LENGTH: 350
<212> TYPE: DNA
<213> ORGANISM: Mus sp.
<220> FEATURE:
<221> NAME/KEY: CDS
<222> LOCATION: (1)..(348)

<400> SEQUENCE: 5 cag gtg cag ctg aag cag tct gga gct gag ctg atg aag cct ggg gcc    48
Gln Val Gln Leu Lys Gln Ser Gly Ala Glu Leu Met Lys Pro Gly Ala
1               5                   10                  15 tca gtg aag ata tcc tgc aag gct act ggc tac aca ttc agt agc tac    96
Ser Val Lys Ile Ser Cys Lys Ala Thr Gly Tyr Thr Phe Ser Ser Tyr
            20                  25                  30 tgg ata gag tgg gta aag cag agg cct gga cat ggc ctt gag tgg att   144
Trp Ile Glu Trp Val Lys Gln Arg Pro Gly His Gly Leu Glu Trp Ile
        35                  40                  45 gga gag att tta cct gga agt ggt agt act aac tac aat gag aag ttc   192
Gly Glu Ile Leu Pro Gly Ser Gly Ser Thr Asn Tyr Asn Glu Lys Phe
    50                  55                  60 aag ggc aag gcc aca ttc act gca gat aca tcc tcc aac aca gcc tac   240
Lys Gly Lys Ala Thr Phe Thr Ala Asp Thr Ser Ser Asn Thr Ala Tyr
65                  70                  75                  80 atg caa ctc agc agc ctg aca tct gag gac tct gcc gtc tat tac tgt   288
Met Gln Leu Ser Ser Leu Thr Ser Glu Asp Ser Ala Val Tyr Tyr Cys
                85                  90                  95 gca aga gag gat agg tac gac ggt gac tac tgg ggc caa ggc acc act   336
Ala Arg Glu Asp Arg Tyr Asp Gly Asp Tyr Trp Gly Gln Gly Thr Thr
            100                 105                 110 ctc aca gtc tcg ag                                                 350
Leu Thr Val Ser
        115

<210> SEQ ID NO 6
<211> LENGTH: 116
<212> TYPE: PRT
<213> ORGANISM: Mus sp.

<400> SEQUENCE: 6

```
Gln Val Gln Leu Lys Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Asn Tyr Asn Glu Lys Phe
50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Asp Arg Tyr Asp Gly Asp Tyr Trp Gly Gln Gly Thr Thr
            100                 105                 110

Leu Thr Val Ser
            115
```

<210> SEQ ID NO 7
<211> LENGTH: 337
<212> TYPE: DNA
<213> ORGANISM: Mus sp.
<220> FEATURE:
<221> NAME/KEY: CDS
<222> LOCATION: (1)..(336)

<400> SEQUENCE: 7

```
cag gct gtt gtg act cag gaa tct gca ctc acc aca tca cct ggt gaa      48
Gln Ala Val Val Thr Gln Glu Ser Ala Leu Thr Thr Ser Pro Gly Glu
1               5                   10                  15 aca gtc aca ctc act tgt cgc tca agt act ggg gct gtt aca act agt      96
Thr Val Thr Leu Thr Cys Arg Ser Ser Thr Gly Ala Val Thr Thr Ser
                20                  25                  30 aac tat gcc aac tgg gtc caa gaa aaa cca gat cat tta ttc act ggt     144
Asn Tyr Ala Asn Trp Val Gln Glu Lys Pro Asp His Leu Phe Thr Gly
            35                  40                  45 cta ata ggt ggt acc aac aac cga gct cca ggt gtt cct gcc aga ttc     192
Leu Ile Gly Gly Thr Asn Asn Arg Ala Pro Gly Val Pro Ala Arg Phe
50                  55                  60 tca ggc tcc ctg att gga gac aag gct gcc ctc acc atc aca ggg gca     240
Ser Gly Ser Leu Ile Gly Asp Lys Ala Ala Leu Thr Ile Thr Gly Ala
65                  70                  75                  80 cag act gag gat gag gca ata tat ttc tgt gct cta tgg tac agc aac     288
Gln Thr Glu Asp Glu Ala Ile Tyr Phe Cys Ala Leu Trp Tyr Ser Asn
                85                  90                  95 cac tgg gtg ttc ggt gga gga acc aaa ctg act gtc cta ggt cag ccc c   337
His Trp Val Phe Gly Gly Gly Thr Lys Leu Thr Val Leu Gly Gln Pro
            100                 105                 110
```

<210> SEQ ID NO 8
<211> LENGTH: 112
<212> TYPE: PRT
<213> ORGANISM: Mus sp.

<400> SEQUENCE: 8

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45
```

```
Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly Gln Pro
            100                 105                 110
```

<210> SEQ ID NO 9
<211> LENGTH: 351
<212> TYPE: DNA
<213> ORGANISM: Mus sp.
<220> FEATURE:
<221> NAME/KEY: CDS
<222> LOCATION: (1)..(351)

<400> SEQUENCE: 9

```
cag gtg cag ctg aag cag tct gga cct gag ctg gag aag cct ggc gct      48
Gln Val Gln Leu Lys Gln Ser Gly Pro Glu Leu Glu Lys Pro Gly Ala
1               5                   10                  15 tca gtg aag ata tcc tgc aag gct tct ggt tac tca ttc act ggc tac      96
Ser Val Lys Ile Ser Cys Lys Ala Ser Gly Tyr Ser Phe Thr Gly Tyr
            20                  25                  30 aac atg aac tgg gtg aag cag agc aat gga aag agc ctt gag tgg att     144
Asn Met Asn Trp Val Lys Gln Ser Asn Gly Lys Ser Leu Glu Trp Ile
        35                  40                  45 gga aat att gat cct tac tat ggt ggt act agc tac aac cag aag ttc     192
Gly Asn Ile Asp Pro Tyr Tyr Gly Gly Thr Ser Tyr Asn Gln Lys Phe
    50                  55                  60 aag ggc aag gcc aca ttg act gta gac aaa tcc tcc aac aca gcc tac     240
Lys Gly Lys Ala Thr Leu Thr Val Asp Lys Ser Ser Asn Thr Ala Tyr
65                  70                  75                  80 atg cac ctc aag agc ctg aca tct gag gac tct gca gtc tat tac tgt     288
Met His Leu Lys Ser Leu Thr Ser Glu Asp Ser Ala Val Tyr Tyr Cys
                85                  90                  95 gca aga gat agt agc tcc tgg ttt gct tac tgg ggc caa ggg act ctg     336
Ala Arg Asp Ser Ser Ser Trp Phe Ala Tyr Trp Gly Gln Gly Thr Leu
            100                 105                 110 gtc act gtc tct gca                                                 351
Val Thr Val Ser Ala
        115
```

<210> SEQ ID NO 10
<211> LENGTH: 117
<212> TYPE: PRT
<213> ORGANISM: Mus sp.

<400> SEQUENCE: 10

```
Gln Val Gln Leu Lys Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Gly Thr Ser Tyr Asn Gln Lys Phe
    50                  55                  60

Lys Gly Lys Ala Thr Leu Thr Val Asp Lys Ser Ser Asn Thr Ala Tyr
65                  70                  75                  80
```

```
Met His Leu Lys Ser Leu Thr Ser Glu Asp Ser Ala Val Tyr Tyr Cys
                85                  90                  95

Ala Arg Asp Ser Ser Trp Phe Ala Tyr Trp Gly Gln Gly Thr Leu
            100                 105                 110

Val Thr Val Ser Ala
        115

<210> SEQ ID NO 11
<211> LENGTH: 325
<212> TYPE: DNA
<213> ORGANISM: Mus sp.
<220> FEATURE:
<221> NAME/KEY: CDS
<222> LOCATION: (1)..(324)

<400> SEQUENCE: 11 gac atc cag ctg act cag tct cca gcc tcc cta tct gca tct gtg gga      48
Asp Ile Gln Leu Thr Gln Ser Pro Ala Ser Leu Ser Ala Ser Val Gly
1               5                   10                  15 gaa act gtc acc atc aca tgt cga gca agt ggg aat att cac aat tat      96
Glu Thr Val Thr Ile Thr Cys Arg Ala Ser Gly Asn Ile His Asn Tyr
            20                  25                  30 tta gca tgg tat cag cag aaa cag gga aaa tct cct cag ctc ctg gtc     144
Leu Ala Trp Tyr Gln Gln Lys Gln Gly Lys Ser Pro Gln Leu Leu Val
        35                  40                  45 tat aat gca aaa acc tta gca gat ggt gtg cca tca agg ttc agt ggc     192
Tyr Asn Ala Lys Thr Leu Ala Asp Gly Val Pro Ser Arg Phe Ser Gly
    50                  55                  60 agt gga tca gga aca caa tat tct ctc aag atc aac agc ctg cag cct     240
Ser Gly Ser Gly Thr Gln Tyr Ser Leu Lys Ile Asn Ser Leu Gln Pro
65                  70                  75                  80 gaa gat ttt ggg agt tat tac tgt caa cat ttt tgg att act ccg tgg     288
Glu Asp Phe Gly Ser Tyr Tyr Cys Gln His Phe Trp Ile Thr Pro Trp
                85                  90                  95 acg ttc ggt gga ggc acc aag ctg gag atc taa cgg a                    325
Thr Phe Gly Gly Gly Thr Lys Leu Glu Ile     Arg
            100                 105

<210> SEQ ID NO 12
<211> LENGTH: 106
<212> TYPE: PRT
<213> ORGANISM: Mus sp.

<400> SEQUENCE: 12

Asp Ile Gln Leu Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ile Thr Pro Trp
                85                  90                  95

Thr Phe Gly Gly Gly Thr Lys Leu Glu Ile
            100                 105

<210> SEQ ID NO 13
```

```
<211> LENGTH: 20
<212> TYPE: DNA
<213> ORGANISM: Unknown
<220> FEATURE:
<223> OTHER INFORMATION: PCR primer TF4

<400> SEQUENCE: 13
acggaacccg ctcgatctcg                                              20

<210> SEQ ID NO 14
<211> LENGTH: 20
<212> TYPE: DNA
<213> ORGANISM: Unknown
<220> FEATURE:
<223> OTHER INFORMATION: PCR primer TF5

<400> SEQUENCE: 14
cgtgacaacc tcgatgacgt                                              20

<210> SEQ ID NO 15
<211> LENGTH: 35
<212> TYPE: DNA
<213> ORGANISM: Unknown
<220> FEATURE:
<223> OTHER INFORMATION: PCR primer TF1

<400> SEQUENCE: 15
atctgcggat ccaccatgga gacccctgcc tggcc                             35

<210> SEQ ID NO 16
<211> LENGTH: 66
<212> TYPE: DNA
<213> ORGANISM: Unknown
<220> FEATURE:
<223> OTHER INFORMATION: PCR primer TF3

<400> SEQUENCE: 16
atctgcctcg agttaatggt gatggtgatg gtgggatcct ctttctctga attccccttt  60
ctcctg                                                             66

<210> SEQ ID NO 17
<211> LENGTH: 66
<212> TYPE: DNA
<213> ORGANISM: Unknown
<220> FEATURE:
<223> OTHER INFORMATION: PCR primer TF1

<400> SEQUENCE: 17
atctgcctcg agttaatggt gatggtgatg gtgggatcct cttgaaacat tcagtgggga  60
gttctc                                                             66

<210> SEQ ID NO 18
<211> LENGTH: 363
<212> TYPE: DNA
<213> ORGANISM: Mus sp.
<220> FEATURE:
<221> NAME/KEY: CDS
<222> LOCATION: (1)..(363)

<400> SEQUENCE: 18 gag gtc cag ctg cag caa tct gga gct gag ctg atg aag cct ggg gcc   48
Glu Val Gln Leu Gln Gln Ser Gly Ala Glu Leu Met Lys Pro Gly Ala
1               5                   10                  15 tca gtg aag ata tcc tgc aag gct act ggc tac aca ttc agt agc tac   96
Ser Val Lys Ile Ser Cys Lys Ala Thr Gly Tyr Thr Phe Ser Ser Tyr
```

```
                    20                  25                  30
tgg ata gag tgg gta aag cag agg cct gga cat ggc ctt gag tgg att    144
Trp Ile Glu Trp Val Lys Gln Arg Pro Gly His Gly Leu Glu Trp Ile
         35                  40                  45 gga gag att tta cct gga agt gct agt act aag tac aat gag aag ttc    192
Gly Glu Ile Leu Pro Gly Ser Ala Ser Thr Lys Tyr Asn Glu Lys Phe
 50                  55                  60 aag ggc aag gcc aca ttc act gca gat aca tcc tcc aac aca gcc tac    240
Lys Gly Lys Ala Thr Phe Thr Ala Asp Thr Ser Ser Asn Thr Ala Tyr
 65                  70                  75                  80 atg caa ctc agc agc ctg aca tct gag gac tct gcc gtc tat tac tgt    288
Met Gln Leu Ser Ser Leu Thr Ser Glu Asp Ser Ala Val Tyr Tyr Cys
                 85                  90                  95 gca aga gat tat tac tac ggt agc agc tac ggg ttt gct tac tgg ggc    336
Ala Arg Asp Tyr Tyr Tyr Gly Ser Ser Tyr Gly Phe Ala Tyr Trp Gly
            100                 105                 110 caa ggg act ctg gtc act gtc tcg agt                                363
Gln Gly Thr Leu Val Thr Val Ser Ser
            115                 120
```

<210> SEQ ID NO 19
<211> LENGTH: 121
<212> TYPE: PRT
<213> ORGANISM: Mus sp.

<400> SEQUENCE: 19

```
Glu Val Gln Leu Gln Gln Ser Gly Ala Glu Leu Met Lys Pro Gly Ala
 1               5                  10                  15

Ser Val Lys Ile Ser Cys Lys Ala Thr Gly Tyr Thr Phe Ser Ser Tyr
                 20                  25                  30

Trp Ile Glu Trp Val Lys Gln Arg Pro Gly His Gly Leu Glu Trp Ile
         35                  40                  45

Gly Glu Ile Leu Pro Gly Ser Ala Ser Thr Lys Tyr Asn Glu Lys Phe
 50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Tyr Tyr Tyr Gly Ser Ser Tyr Gly Phe Ala Tyr Trp Gly
            100                 105                 110

Gln Gly Thr Leu Val Thr Val Ser Ser
            115                 120
```

<210> SEQ ID NO 20
<211> LENGTH: 330
<212> TYPE: DNA
<213> ORGANISM: Mus sp.
<220> FEATURE:
<221> NAME/KEY: CDS
<222> LOCATION: (1)..(330)

<400> SEQUENCE: 20

```
cag gct gtt gtg act cag gaa tct gca ctc acc aca tca cct ggt gaa     48
Gln Ala Val Val Thr Gln Glu Ser Ala Leu Thr Thr Ser Pro Gly Glu
 1               5                  10                  15 aca gtc aca ctc act tgt cgc tca agt act ggg gct gtt aca act agt     96
Thr Val Thr Leu Thr Cys Arg Ser Ser Thr Gly Ala Val Thr Thr Ser
                 20                  25                  30 aac tat gcc aac tgg gtc caa gaa aaa cca gat cat tta ttc act ggc    144
Asn Tyr Ala Asn Trp Val Gln Glu Lys Pro Asp His Leu Phe Thr Gly
```

```
              35                  40                  45
cta ata ggt ggt acc aac aac cga ggt cca ggt gtt cct gcc aga ttc      192
Leu Ile Gly Gly Thr Asn Asn Arg Gly Pro Gly Val Pro Ala Arg Phe
    50                  55                  60 tca ggc tcc ctg att gga gac aag gct gcc ctc acc atc aca ggg gca      240
Ser Gly Ser Leu Ile Gly Asp Lys Ala Ala Leu Thr Ile Thr Gly Ala
65                  70                  75                  80 cag act gag gat gag gca gta tat ttc tgt gct cta tgg tac agc aac      288
Gln Thr Glu Asp Glu Ala Val Tyr Phe Cys Ala Leu Trp Tyr Ser Asn
                85                  90                  95 cat tgg gtg ttc ggt gga gga acc aaa ctg act gtc cta ggt              330
His Trp Val Phe Gly Gly Gly Thr Lys Leu Thr Val Leu Gly
            100                 105                 110

<210> SEQ ID NO 21
<211> LENGTH: 110
<212> TYPE: PRT
<213> ORGANISM: Mus sp.

<400> SEQUENCE: 21

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Gly Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Val Tyr Phe Cys Ala Leu Trp Tyr Ser Asn
                85                  90                  95

His Trp Val Phe Gly Gly Gly Thr Lys Leu Thr Val Leu Gly
            100                 105                 110

<210> SEQ ID NO 22
<211> LENGTH: 354
<212> TYPE: DNA
<213> ORGANISM: Mus sp.
<220> FEATURE:
<221> NAME/KEY: CDS
<222> LOCATION: (1)..(354)

<400> SEQUENCE: 22 cag gtc caa ctg cag cag cct ggg gct gag ctt gtg aag cct ggg gct       48
Gln Val Gln Leu Gln Gln Pro Gly Ala Glu Leu Val Lys Pro Gly Ala
1               5                   10                  15 tca gtg aag ctg tcc tgc aag act tct ggc tac acc ttc acc agc tac       96
Ser Val Lys Leu Ser Cys Lys Thr Ser Gly Tyr Thr Phe Thr Ser Tyr
            20                  25                  30 tgg atg cac tgg gtg aag cag agg cct gga caa ggc ctt gag tgg atc      144
Trp Met His Trp Val Lys Gln Arg Pro Gly Gln Gly Leu Glu Trp Ile
        35                  40                  45 gga gag att gat cct tct gat agt tat act aac tac aat caa aag ttc      192
Gly Glu Ile Asp Pro Ser Asp Ser Tyr Thr Asn Tyr Asn Gln Lys Phe
    50                  55                  60 aag ggc aag gcc aca ttg act gta gac aaa tcc tcc agc aca gcc tac      240
Lys Gly Lys Ala Thr Leu Thr Val Asp Lys Ser Ser Ser Thr Ala Tyr
65                  70                  75                  80 atg cag ctc agc agc ctg aca tct gag gac tct gcg gtc tat tac tgt      288
```

```
Met Gln Leu Ser Ser Leu Thr Ser Glu Asp Ser Ala Val Tyr Tyr Cys
                85                  90                  95 acc tac tat gtt aac tac tat gct atg gac tac tgg ggt caa gga acc       336
Thr Tyr Tyr Val Asn Tyr Tyr Ala Met Asp Tyr Trp Gly Gln Gly Thr
                100                 105                 110 tca gtc acc gtc tcc tca                                                354
Ser Val Thr Val Ser Ser
        115

<210> SEQ ID NO 23
<211> LENGTH: 118
<212> TYPE: PRT
<213> ORGANISM: Mus sp.

<400> SEQUENCE: 23

Gln Val Gln Leu Gln Gln Pro Gly Ala Glu Leu Val Lys Pro Gly Ala
1               5                   10                  15

Ser Val Lys Leu Ser Cys Lys Thr Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asp Pro Ser Asp Ser Tyr Thr Asn Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Tyr Tyr Val Asn Tyr Tyr Ala Met Asp Tyr Trp Gly Gln Gly Thr
                100                 105                 110

Ser Val Thr Val Ser Ser
        115

<210> SEQ ID NO 24
<211> LENGTH: 318
<212> TYPE: DNA
<213> ORGANISM: Mus sp.
<220> FEATURE:
<221> NAME/KEY: CDS
<222> LOCATION: (1)..(318)

<400> SEQUENCE: 24 caa att gtt ctc acc cag tct cca gca atc atg tct gca tct cta ggg       48
Gln Ile Val Leu Thr Gln Ser Pro Ala Ile Met Ser Ala Ser Leu Gly
1               5                   10                  15 gag gag atc acc cta acc tgc agt gcc agc tcg agt gta agt tac atg       96
Glu Glu Ile Thr Leu Thr Cys Ser Ala Ser Ser Ser Val Ser Tyr Met
                20                  25                  30 cac tgg tac cag cag aag tca ggc act tct ccc aaa ctc ttg att tat       144
His Trp Tyr Gln Gln Lys Ser Gly Thr Ser Pro Lys Leu Leu Ile Tyr
            35                  40                  45 agc aca tcc aac ctg gct tct gga gtc cct tct cgc ttc agt ggc agt       192
Ser Thr Ser Asn Leu Ala Ser Gly Val Pro Ser Arg Phe Ser Gly Ser
        50                  55                  60 ggg tct ggg acc ttt tat tct ctc aca atc agc agt gtg gag gct gaa       240
Gly Ser Gly Thr Phe Tyr Ser Leu Thr Ile Ser Ser Val Glu Ala Glu
65                  70                  75                  80 gat gct gcc gat tat tac tgc cat cag tgg agt agt tat cca tac acg       288
Asp Ala Ala Asp Tyr Tyr Cys His Gln Trp Ser Ser Tyr Pro Tyr Thr
                85                  90                  95 ttc gga ggg ggg acc aag ctg gaa ata aaa                                318
```

Phe Gly Gly Gly Thr Lys Leu Glu Ile Lys
            100                 105

<210> SEQ ID NO 25
<211> LENGTH: 106
<212> TYPE: PRT
<213> ORGANISM: Mus sp.

<400> SEQUENCE: 25

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Val Ser Tyr Met
            20                  25                  30

His Trp Tyr Gln Gln Lys Ser Gly Thr Ser Pro Lys Leu Leu Ile Tyr
            35                  40                  45

Ser Thr Ser Asn Leu Ala Ser Gly Val Pro Ser Arg Phe Ser Gly Ser
        50                  55                  60

Gly Ser Gly Thr Phe Tyr Ser Leu Thr Ile Ser Val Glu Ala Glu
65                  70                  75                  80

Asp Ala Ala Asp Tyr Tyr Cys His Gln Trp Ser Ser Tyr Pro Tyr Thr
                85                  90                  95

Phe Gly Gly Gly Thr Lys Leu Glu Ile Lys
            100                 105

<210> SEQ ID NO 26
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 26 cag gtg cag ctg aag gag tct gga gct gag ctg atg aag cct ggg gcc         48
Gln Val Gln Leu Lys Glu Ser Gly Ala Glu Leu Met Lys Pro Gly Ala
1               5                   10                  15 tca gtg aag ata tcc tgc aag gct act ggc tac aca ttc agt agc tac         96
Ser Val Lys Ile Ser Cys Lys Ala Thr Gly Tyr Thr Phe Ser Ser Tyr
            20                  25                  30 tgg ata gag tgg gta aag cag agg cct gga cat ggc ctt gag tgg att        144
Trp Ile Glu Trp Val Lys Gln Arg Pro Gly His Gly Leu Glu Trp Ile
        35                  40                  45 gga gag att tta cct gga agt ggt agt act aac tac aat gag aag ttc        192
Gly Glu Ile Leu Pro Gly Ser Gly Ser Thr Asn Tyr Asn Glu Lys Phe
    50                  55                  60 aag ggc aag gcc aca ttc act gca gat aca tcc tcc aac aca gcc tac        240
Lys Gly Lys Ala Thr Phe Thr Ala Asp Thr Ser Ser Asn Thr Ala Tyr
65                  70                  75                  80 atg caa ctc agc agc ctg aca tct gag gac tct gcc gtc tat tac tgt        288
Met Gln Leu Ser Ser Leu Thr Ser Glu Asp Ser Ala Val Tyr Tyr Cys
                85                  90                  95 gca aga gac agg aac ggc tac gtg aac tac ttt gac tcc tgg ggc caa        336
Ala Arg Asp Arg Asn Gly Tyr Val Asn Tyr Phe Asp Ser Trp Gly Gln
            100                 105                 110 ggc acc act ctc aca gtc tcc tca                                         360
Gly Thr Thr Leu Thr Val Ser Ser
        115                 120

<210> SEQ ID NO 27
<211> LENGTH: 120
<212> TYPE: PRT

<213> ORGANISM: Mus sp.

<400> SEQUENCE: 27

```
Gln Val Gln Leu Lys Glu Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Asn Tyr Asn Glu Lys Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Arg Asn Gly Tyr Val Asn Tyr Phe Asp Ser Trp Gly Gln
            100                 105                 110

Gly Thr Thr Leu Thr Val Ser Ser
        115                 120
```

<210> SEQ ID NO 28
<211> LENGTH: 351
<212> TYPE: DNA
<213> ORGANISM: Mus sp.
<220> FEATURE:
<221> NAME/KEY: CDS
<222> LOCATION: (1)..(351)

<400> SEQUENCE: 28

```
gat gtg aag ctt cag gag tca gga cct gac ctg gtg aaa cct tct cag        48
Asp Val Lys Leu Gln Glu Ser Gly Pro Asp Leu Val Lys Pro Ser Gln
1               5                   10                  15 tca ctt tca ctc acc tgc act gtc act ggc tac tcc atc acc agt ggt        96
Ser Leu Ser Leu Thr Cys Thr Val Thr Gly Tyr Ser Ile Thr Ser Gly
                20                  25                  30 tat agc tgg cac tgg atc cgg cag ttt cca gga aac aaa ctg gaa tgg        144
Tyr Ser Trp His Trp Ile Arg Gln Phe Pro Gly Asn Lys Leu Glu Trp
            35                  40                  45 atg ggc tac ata cac tac agt ggt agc act aag tac aac cca tct ctc        192
Met Gly Tyr Ile His Tyr Ser Gly Ser Thr Lys Tyr Asn Pro Ser Leu
        50                  55                  60 aaa agt cga atc tct atc act cga gac aca tcc aag aac cag ttc ttc        240
Lys Ser Arg Ile Ser Ile Thr Arg Asp Thr Ser Lys Asn Gln Phe Phe
65                  70                  75                  80 ctg cag ttg aat tct gtg act act gag gac aca gcc aca tat tac tgt        288
Leu Gln Leu Asn Ser Val Thr Thr Glu Asp Thr Ala Thr Tyr Tyr Cys
                85                  90                  95 gca aga ctc tgg agt tgg tac ttc gat gtc tgg ggc gca ggg acc acg        336
Ala Arg Leu Trp Ser Trp Tyr Phe Asp Val Trp Gly Ala Gly Thr Thr
            100                 105                 110 gtc acc gtc tcc tca                                                    351
Val Thr Val Ser Ser
        115
```

<210> SEQ ID NO 29
<211> LENGTH: 117
<212> TYPE: PRT
<213> ORGANISM: Mus sp.

<400> SEQUENCE: 29

```
Asp Val Lys Leu Gln Glu Ser Gly Pro Asp Leu Val Lys Pro Ser Gln
 1               5                  10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Lys Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Leu Trp Ser Trp Tyr Phe Asp Val Trp Gly Ala Gly Thr Thr
            100                 105                 110

Val Thr Val Ser Ser
            115
```

<210> SEQ ID NO 30
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 30

```
aac att atg atg aca cag tcg cca tca tct ctg gct gtg tct gca gga       48
Asn Ile Met Met Thr Gln Ser Pro Ser Ser Leu Ala Val Ser Ala Gly
 1               5                  10                  15 gaa aag gtc act atg agc tgt aag tcc agt caa agt gtt tta tac agt       96
Glu Lys Val Thr Met Ser Cys Lys Ser Ser Gln Ser Val Leu Tyr Ser
            20                  25                  30 tca aat cag aag aac tac ttg gcc tgg tac cag cag aaa cca ggg cag      144
Ser Asn Gln Lys Asn Tyr Leu Ala Trp Tyr Gln Gln Lys Pro Gly Gln
        35                  40                  45 tct cct aaa ctg ctg atc tac tgg gca tcc act agg gaa tct ggt gtc      192
Ser Pro Lys Leu Leu Ile Tyr Trp Ala Ser Thr Arg Glu Ser Gly Val
    50                  55                  60 cct gat cgc ttc aca ggc agt gga tct ggg aca gat ttt act ctt acc      240
Pro Asp Arg Phe Thr Gly Ser Gly Ser Gly Thr Asp Phe Thr Leu Thr
65                  70                  75                  80 atc agc agt gta caa gct gaa gac ctg gca gtt tat tac tgt cat caa      288
Ile Ser Ser Val Gln Ala Glu Asp Leu Ala Val Tyr Tyr Cys His Gln
                85                  90                  95 tac ctc tcc tcg tac acg ttc gga ggg ggg acc aag ctg gaa ata aaa      336
Tyr Leu Ser Ser Tyr Thr Phe Gly Gly Gly Thr Lys Leu Glu Ile Lys
            100                 105                 110
```

<210> SEQ ID NO 31
<211> LENGTH: 112
<212> TYPE: PRT
<213> ORGANISM: Mus sp.

<400> SEQUENCE: 31

```
Asn Ile Met Met Thr Gln Ser Pro Ser Ser Leu Ala Val Ser Ala Gly
 1               5                  10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45
```

```
Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys His Gln
                 85                  90                  95

Tyr Leu Ser Ser Tyr Thr Phe Gly Gly Gly Thr Lys Leu Glu Ile Lys
            100                 105                 110

<210> SEQ ID NO 32
<211> LENGTH: 57
<212> TYPE: DNA
<213> ORGANISM: Unknown
<220> FEATURE:
<223> OTHER INFORMATION: Signal sequence peptide
<220> FEATURE:
<221> NAME/KEY: CDS
<222> LOCATION: (1)..(57)

<400> SEQUENCE: 32 atg gct tgg gtg tgg acc ttg cta ttc ctg atg gca gct gcc caa agt        48
Met Ala Trp Val Trp Thr Leu Leu Phe Leu Met Ala Ala Ala Gln Ser
 1               5                  10                  15 gcc caa gca                                                            57
Ala Gln Ala <210> SEQ ID NO 33
<211> LENGTH: 19
<212> TYPE: PRT
<213> ORGANISM: Unknown
<220> FEATURE:
<223> OTHER INFORMATION: Synthetic Construct

<400> SEQUENCE: 33

Met Ala Trp Val Trp Thr Leu Leu Phe Leu Met Ala Ala Ala Gln Ser
 1               5                  10                  15

Ala Gln Ala

<210> SEQ ID NO 34
<211> LENGTH: 60
<212> TYPE: DNA
<213> ORGANISM: Unknown
<220> FEATURE:
<223> OTHER INFORMATION: Signal sequence peptide
<220> FEATURE:
<221> NAME/KEY: CDS
<222> LOCATION: (1)..(60)

<400> SEQUENCE: 34 atg gaa tca cag act cag gtc ttc ctc tcc ctg ctg ctc tgg ata tct        48
Met Glu Ser Gln Thr Gln Val Phe Leu Ser Leu Leu Leu Trp Ile Ser
 1               5                  10                  15 ggt acc tgt ggg                                                        60
Gly Thr Cys Gly
            20

<210> SEQ ID NO 35
<211> LENGTH: 20
<212> TYPE: PRT
<213> ORGANISM: Unknown
<220> FEATURE:
<223> OTHER INFORMATION: Synthetic Construct

<400> SEQUENCE: 35
```

-continued

```
Met Glu Ser Gln Thr Gln Val Phe Leu Ser Leu Leu Leu Trp Ile Ser
1               5                   10                  15

Gly Thr Cys Gly
            20
```